United States Patent [19]

Banville et al.

[11] Patent Number: 5,565,433

[45] Date of Patent: Oct. 15, 1996

[54] SULFATED β-GLYCOLIPID DERIVATIVES AS CELL ADHESION INHIBITORS

[75] Inventors: Jacques Banville, St. Hubert; Alain Martel, Delson, both of Canada; Alejandro A. Aruffo, Edmonds, Wash.

[73] Assignee: Bristol-Myers Squibb Company, Princeton, N.J.

[21] Appl. No.: 600,558

[22] Filed: Feb. 12, 1996

Related U.S. Application Data

[63] Continuation of Ser. No. 206,067, Mar. 4, 1994, abandoned.

[51] Int. Cl.[6] .................. A61K 31/70; C07H 11/00
[52] U.S. Cl. .................. 514/25; 536/17.5; 536/17.6; 536/17.9
[58] Field of Search .................. 536/17.5, 17.6, 536/17.9; 514/25

[56] References Cited

U.S. PATENT DOCUMENTS

| | | | |
|---|---|---|---|
| 4,937,328 | 6/1990 | Schmidt et al. | 536/18.6 |
| 4,952,683 | 8/1990 | Tschannen et al. | 536/18.6 |
| 5,211,937 | 5/1993 | Brandley et al. | 424/1.73 |

FOREIGN PATENT DOCUMENTS

| | | |
|---|---|---|
| WO92/01718 | 2/1992 | WIPO . |
| WO92/19633 | 11/1992 | WIPO . |
| WO93/05803 | 4/1993 | WIPO . |
| WO93/10796 | 6/1993 | WIPO . |

OTHER PUBLICATIONS

Springer *Nature* 1990, 346, 425–434.
Green et al. *Biochem. Biophys. Res. Commun.* 1992, 188(1), 244–251.
PNAS vol. 90 No. 4 (1993) Meedhaur et al.
Biotechnology vol. 9 (1991) Hodgson.
Hsu–Lin, S., et al., *J. Biol. Chem.*, 259, 9121–9126 (1984).
Stenberg, P. E., *J. Cell Biol.*, 101, 880–886 (1985).
McEver, R. P., et al., *J. Clin. Invest.*, 84, 92–99 (1989).
Bonfanti, R., et al., *Blood*, 73, 1109–1112 (1989).
Hattori, R., et al., *J. Biol. Chem.*, 264, 7768–7771 (1989).
Hattori, R., et al., *J. Biol. Chem.*, 264, 9053–9060 (1989).
Patel, K. D., et al., *J. Cell Biol.*, 112, 749–759 (1991).
Larsen, E., et al., *Cell*, 63, 467–474 (1990).
Erbe, V. E., et al., *J. Cell Biol.*, 119, 215–217 (1992).
Skinner, M. P., et al., *Biochem. Biophys. Res. Commun.*, 164, 1373–1379 (1989).

Skinner, M. P., et al., *J. Biol. Chem.*, 266, 5371–5374 (1991).
Aruffo, A., et al., *Cell*, 67, 35–44 (1991).
Y. Suzuki, et al., *Biochem. Biophys. Res. Commun.*, 190, 426–434 (1993).
M. S. Mulligan, et al., *Nature*, 364, 149–151 (1993).
Radin, N. S., *Handbook of Neurochemistry*, 3, 415–424 (1969).
Sweeley, C. C., *Pure and Appl. Chem.*, 61(7) 1307–1312 (1989).

*Primary Examiner*—Gary L. Kunz
*Assistant Examiner*—Kathleen Kahler Fonda
*Attorney, Agent, or Firm*—Aldo A. Algieri

[57] ABSTRACT

There is provided novel sulfated p-glycolipid compounds of the formula

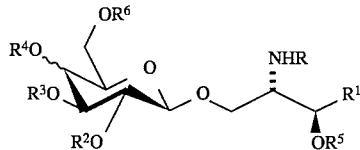

wherein

R is an acyl residue of a fatty acid;

$R^1$ is —(CH=CH)$_m$—(CH$_2$)$_n$—CH$_3$;

$R^2$, $R^3$, $R^4$ and $R^6$ each are independently —SO$_3$H, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or $R_4$ and $R_6$, taken together are isopropylidene; provided at least two of $R^2$, $R^3$, $R^4$ and $R^6$ are —SO$_3$H;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive;

or a non-toxic pharmaceutically acceptable salt, solvate or hydrate thereof which are inhibitors of selectin-mediated cellular adhesion and are useful in the treatment or prevention of inflammatory diseases and other pathological conditions in mammals.

38 Claims, No Drawings

SULFATED β-GLYCOLIPID DERIVATIVES AS CELL ADHESION INHIBITORS

CROSS-REFERENCE TO RELATED APPLICATION

This is a continuation of application U.S. Ser. No. 08/206,067 filed Mar. 4, 1994 now abandoned.

FIELD OF THE INVENTION

The present invention provides a novel series of sulfated β-glycolipid compounds, pharmaceutically acceptable salts and pharmaceutical compositions thereof as inhibitors of selectin-mediated cellular adhesion which are useful in the treatment or prevention of inflammatory disease processes and other pathological conditions mediated by the binding of selectins involved in intercellular adhesion.

BACKGROUND OF THE INVENTION

P-selectin (CD62, GMP140, PADGEM) is a membrane glycoprotein of ~140 kDa expressed by activated platelets and vascular endothelial cells. In resting platelets and vascular endothelial cells P-selectin is sequestered in p granules [Hsu-Lin, S., et al., *J. Biol. Chem.*, 259, 9121–9126 (1984); and Stenberg, P. E., *J. Cell Biol.*, 101, 880–886 (1985)] and Weibel-Palade bodies [McEver, R. P., et al., *J. Clin. Invest.*, 84, 92–99 (1989); and Bonfanti, R., et al., *Blood*, 73, 1109–1112 (1989)], respectively. In response to inflammatory mediators such as thrombin [Hsu-Lin, S., et al., *J. Biol. Chem.*, 259, 9121–9126 (1984); and Stenberg, P. E., *J. Cell Biol.*, 101, 880–886 (1985)], histamine [Hattori, R., et al., *J. Biol. Chem.*, 264, 7768–7771 (1989)], complement components [Hattori, R., et al., *J. Biol. Chem.*, 264, 9053–9060 (1989)], or peroxides [Patel, K. D., et al., *J. Cell Biol.*, 112, 749–759 (1991)] and cytokines such as interleukin-1 and tumor necrosis factor, P-selectin is rapidly mobilized from these intracellular stores to the cell surface where it mediates the initial binding interactions of activated platelets with leukocytes and the vascular wall, and of leukocytes with activated vascular endothelial cells. P-selectin is a member of a family of adhesion molecules which includes E-selectin (ELAM-1), which is expressed by activated vascular endothelial cells, and L-selectin (Leu 8, LAM-1, LECAM), which is expressed by leukocytes. These proteins are type I membrane proteins and are composed of an amino terminal lectin domain followed by an epidermal growth factor (EGF) like domain, a variable number of complement receptor related repeats (CR), a hydrophobic membrane spanning region and a cytoplasmic domain. As indicated by high sequence homology, these proteins are not only structurally but also functionally related, modulating the trafficking of peripheral blood leukocyte by permitting adhesive interactions between leukocytes and endothelial cells. These binding interactions are predominately mediated by contacts between the lectin domain of the selectin and various carbohydrate ligands.

Although it is now widely accepted that a lectin domain/carbohydrate interaction is primarily responsible for mediating P-selectin/myeloid cell binding, the exact molecular nature of the P-selectin ligand is not knowns. Binding of P-selectin to myeloid cells is $Ca^{2+}$ dependent as well as neuraminidase and protease sensitive. The binding of P-selectin to myeloid cell lines can be inhibited by growing the cells in the presence of sodium selenate and inhibitor of sulfation. P-selectin has been shown to bind to the carbohydrate $Le^x$ (CD15) [Larsen, E., et al., *Cell*, 63, 467–474 (1990)] and its sialylated form, sialyl-$Le^x$ ($sLe^x$) [Erbe, V. E., et al., *J. Cell Biol.*, 119, 215–217 (1992)], and there is evidence that these carbohydrates and/or others like them are presented to P-selectin by a discrete number of cell surface proteins including L-selectin. Various anionic polymers, including heparin, fucoidan, and dextran sulfate have also been shown to inhibit P-selectin mediated adhesion [Skinner, M. P., et al., *Biochem. Biophys. Res. Commun.*, 164, 1373–1379 (1989); and *J. Biol. Chem.*, 266, 5371–5374 (1991)]. In addition, P-selectin has been shown to bind 3-sulfated galactosyl ceramides (sulfatides) [Aruffo, A., et al., *Cell*, 67, 35–44 (1991)]. Although the physiological relevance of this interaction remains to be elucidated, it is known that myeloid cells can excrete large quantities of sulfatides on activation. This suggests that sulfatides might participate in leukocyte extravasation at sites of inflammation by displacing the adhesion-mediating leukocyte surface ligand(s), thereby permitting the efficient exit of leukocytes from the blood stream at sites of inflammation.

A number of publications have appeared which describe new agents as inhibitors of cellular adhesion. Some of these publications, but not limited to, include the use of peptides and carbohydrate structures in International patent application WO 92/01718 published Feb. 6, 1992; the use of substituted lactose and lactosamine derivatives in International patent application WO 93/10796 published Jun. 10, 1993; the use of glycoconjugates in International patent application WO 93/05803 published April 1, 1993; the use of sulfated glycolipid derivatives by Y. Suzuki, et al., *Biochem. Biophys. Res. Commun.*, 190, 426–434 (1993) and the use of oligosaccharides by M. S. Mulligan, et al., *Nature*, 364, 149–151 (1993).

However, there are many situations in which the recruitment of leukocytes by adhesion to the endothelial cells is abnormal or in excess, and the end result is tissue damage instead of repair. Thus, there is a need to develop specific and potent compounds which can inhibit the initial cellular adhesion process. It is the object of the present invention to provide new sulfated glycolipids which are inhibitors of cell adhesion and, therefore, useful in man for the treatment and/or prevention of acute or chronic inflammatory diseases such as rheumatoid arthritis, asthma, allergy conditions, psoriasis, septic shock and other indications such as reperfusion injury, adult respiratory distress syndrome, ischemia, ulcerative colitis, vasculitides, atherosclerosis and inflammatory bowel disease, multiple sclerosis and tumor metastases.

SUMMARY OF THE INVENTION

The present invention provides novel sulfated β-glycolipids having the formula

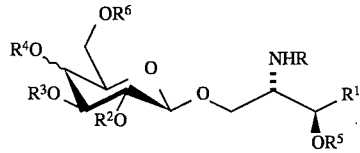

I wherein R, $R^1$, $R^2$, $R^3$, $R^4$, $R^5$ and $R^6$ are as defined below, or a non-toxic pharmaceutically acceptable salt, solvate or hydrate thereof which are inhibitors of selectin-mediated cellular adhesion. The present invention also provides pharmaceutical compositions comprising said sulfated β-glycolipids and to the method of treatment or prevention of conditions characterized by selectin-mediated cellular adhesion such as inflammatory diseases and other pathological conditions in mammals.

DESCRIPTION OF THE INVENTION

The present invention provides novel sulfated β-glycolipid compounds which are inhibitors of P-selectin mediated cellular adhesion and which have the formula

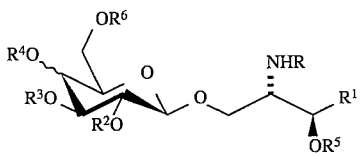

wherein

R is an acyl residue of a fatty acid;

$R^1$ is —(CH=CH)$_m$—(CH$_2$)$_n$—CH$_3$;

$R^2$, $R^3$, $R^4$ and $R^6$ are independently at least two —SO$_3$H;

$R^2$, $R^3$, $R^4$ $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; or $R^4$ and $R^6$, taken together is benzylidene or $R^3$ and $R^4$, taken together is isopropylidene;

m is an integer of 0 or 1;

n is an integer of from 5 to 14, inclusive;

or a non-toxic pharmaceutically acceptable salt, solvate or hydrate thereof.

The present invention also provides a method for the treatment or prevention of inflammatory diseases and other pathological conditions characterized by selectin-mediated cellular adhesion, which comprises administering a therapeutically effective amount of a compound of formula I or a non-toxic pharmaceutically acceptable salt, solvate or hydrate thereof.

The terms "$C_{1-4}$ alkyl", and "$C_{1-4}$ alkoxy" as used herein and in the claims (unless the context indicates otherwise) mean straight or branched chain alkyl or alkoxy groups such as methyl, ethyl, propyl, isopropyl, butyl, isobutyl, t-butyl. Preferably, these groups contain from 1 to 2 carbon atoms. The term "arylalkyl" as used herein and in the claims means a phenyl group attached via an alkyl moiety containing from 1 to 4 carbon atoms such as methyl, ethyl, propyl, butyl and the like, and most preferably means benzyl or phenylethyl. Unless otherwise specified, the term "halogen" as used herein and in the claims is intended to include bromine, chlorine, iodine and fluorine while the term "halide" is intended to include bromide, chloride and iodide anion. Preferably, halogen is chlorine or fluorine. The term "alkanoyl" as used herein and in the claims means acetyl, propionyl and the like.

The term "independently at least two —SO$_3$H" as used herein and in the claims means than a minimum of any two substituents selected from $R^2$, $R^3$, $R^4$ and $R^6$ must be —SO$_3$H as well as any three substituents and including all four substituents to provide a disulfated, trisulfated or tetrasulfated glycolipid. The wavy bond "∿" in the structural formula to which $R^4$O is attached as used herein and in the claims means that the bond may be either in the axial or equatorial configuration as occurs in the monosaccharides selected from galactose and glucose.

The term "non-toxic pharmaceutically acceptable salt" as used herein and in the claims is intended to include non-toxic base addition salts with inorganic and organic bases. Suitable inorganic bases such as alkali and alkaline earth metal bases include metallic cations such as sodium, potassium, magnesium, calcium and the like. Suitable organic bases include amines such as ammonium, trialkyl amines, pyridine, ethanolamine, N-methylglucamine, N-methylmorpholine, lysine, arginine and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

The compounds of the present invention contain a monosaccharide selected from galactose and glucose. The natural occurring sulfatides from brain tissue are part of a class of compounds known as sulfated cerebrosides [N. S. Radin *Handbook of Neurochemistry*, Vol. 3 415–424 (1969)]. The commercially available sulfatides are a mixture of compounds in which the hexose moiety is mainly galactose and the configuration of the hexose in the natural sulfatides is in the β-anomeric form. [C. C. Sweeley, *Pure and Appl. Chem.*, 61(7) 1307–1312 (1989)].

In the method of the present invention, the term "therapeutically effective amount" means the total amount of each active component of the method that is sufficient to show a meaningful patient benefit, i.e., healing of chronic conditions characterized by selectin-mediated cellular adhesion or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with selectin-mediated cellular adhesion.

The term "acyl residue of a fatty acid" as used herein and in the claims means the acyl residue of a naturally occurring saturated or unsaturated fatty acid or a fatty acid derived therefrom. Suitable saturated fatty acids are those described herein and other known fatty acids such as butyric, isovaleric, caproic, caprylic, capric, lauric, myristic, palmitic, stearic, arachidic, behenic, lignoceric, cerotic and the like. Suitable unsaturated fatty acids include the cis and trans isomers of fatty acids such as $\Delta^9$-decylenic, stillingic, $\Delta^9$-dodecylenic, palmitoleic, oleic, ricinoleic, petroselinic, vaccenic, linoleic, linolenic, eleostearic, punicic, licanic, parinaric, gadoleic, arachidonic, 5-eicosenic, 5-docosenic, cetoleic, erucic, 5,13-docosadienic, nervonic and the like.

Hydroxy-protecting groups which can be employed in the present invention to block or protect the hydroxyl group are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Hydroxy-protecting (blocking) groups which are advantageously used are those which are common in carbohydrate chemistry especially for primary alcohols, secondary alcohols and vicinal cis and trans diols.

Suitable hydroxy-protecting groups may be, for example, acyl groups such as acetyl, trichloroacetyl, phenoxycarbonyl, benzyloxycarbonyl, benzhydryloxycarbonyl, trityloxycarbonyl and 2,2,2-trichloroethoxycarbonyl, ether groups such as methoxymethyl, benzyloxymethyl, allyl, benzyl, p-methoxybenzyl, p-nitrobenzyl, benzhydryl, trityl or triorganosilyl groups such as tri($C_1$–$C_6$) alkylsilyl (e.g., trimethylsilyl, triethylsilyl, triisopropylsilyl, isopropyldimethylsilyl, t-butydimethylsilyl, methyldiisopropylsilyl or methyldi-t-butylsilyl), t-butyl-diphenylsilyl, triarylsilyl (e.g. triphenylsilyl, tri-p-xylylsilyl) or triaralkylsilyl (e.g. tribenzylsilyl). Examples of these and other suitable hydroxyprotecing groups and methods for their formation and removal are known in the art, e.g., see *Protective Groups in Organic Synthesis,* second ed., T. W. Greene and P. G. M. Wuts, John Wiley & Sons, New York, 1991, Chapter 2 and references therein.

The compounds of Formula I may be prepared by various procedures such as those illustrated herein in the examples, in the reaction schemes and variations thereof which would be evident to those skilled in the art. The various sulfate substituted glycolipid compounds of Formula I wherein the carbohydrate moiety is galactose and glucose are advantageously prepared from the intermediates of Formula Va or Vb as generally illustrated in Reaction Schemes 3, 4, 5, 6 and 7.

The preparation of a generic azido diol lipid of Formula II (occasionally referred to as azidosphingosine) wherein $R^1$ is as previously defined is illustrated in the process shown in Reaction Scheme 1. Thus, 2,4-O-benzylidene-D-threose is advantageously reacted with the desired phosphonium salt in a Wittig reaction by the general procedures described by P. Zimmerman, et al., *Liebigs Ann. Chem.,* 663–667 (1988) to produce the desired trans olefin wherein n=5–14. The olefin moiety may be retained in the process to provide compounds of Formula I wherein m=1 in the definition of $R^1$ or, if desired, the olefin may be reduced by conventional hydrogenation procedures to eventually provide compounds of Formula I wherein m=0 in the definition of $R^1$. The hydroxy function of the intermediate is treated with triflic anhydride and sodium azide to produce the cyclic azido intermediate with inversion of configuration followed by acid treatment to remove the benzylidene blocking group to produce the desired azido diol intermediate of Formula II wherein $R^1$ is —$(CH=CH)_m$—$(CH_2)_n$—$CH_3$. It is advantageous in the present process to block (protect) the secondary alcohol or allylic alcohol as the case may be in the compound of Formula II by first readily blocking the primary alcohol by conventional blocking (protecting) groups with an organosilyl group such as t-butyldimethylsilyl followed by the reaction with the desired $R^s$ substitutent, as previously defined and wherein X is a conventional leaving group well-known in the art such as chloro, bromo, iodo, fluorosulfonyl and the like. After the displacement is completed, the silyl blocking group may readily be removed such as with tetrabutylammonium fluoride to give the desired compound of Formula III which is now suitable for use in the coupling reaction with a carbohydrate moiety, as illustrated in Reaction Scheme 2.

Reaction Scheme 1

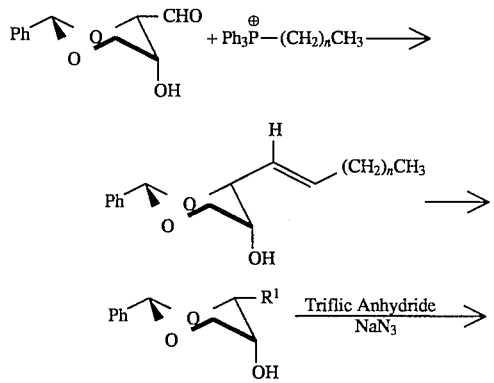

Reaction Scheme 1 -continued

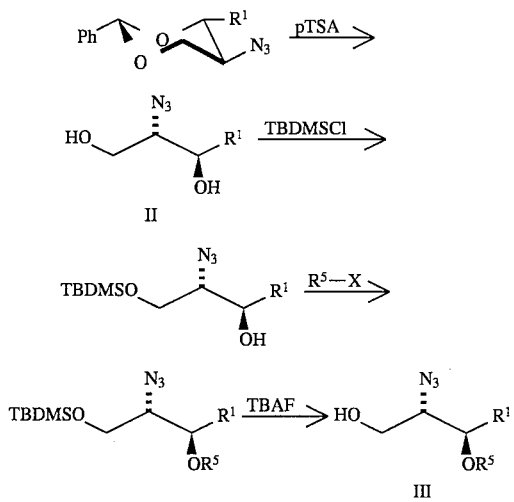

There are various processes which are useful for the preparation of compounds of Formula Va and Vb having the galactose and glucose, respectively with the β-anomeric configuration in the 1-position and these are exemplified in the examples. However, the preferred process for the preparation of the β-anomeric glycolipids of the present invention are illustrated in Reaction Scheme 2.

Reaction Scheme 2

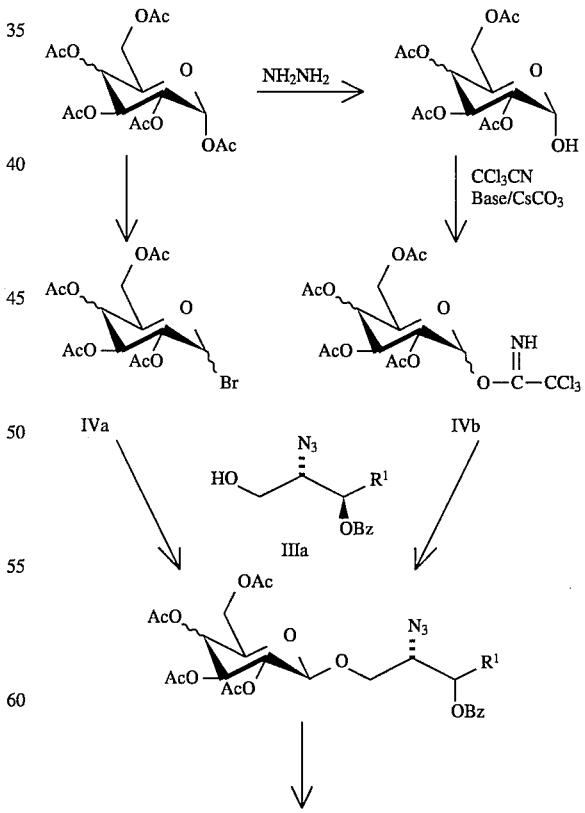

-continued
Reaction Scheme 2

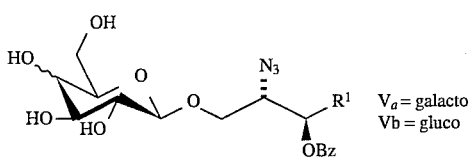

$V_a$ = galacto
$V_b$ = gluco

The preparation of either the β-galacto or β-gluco intermediate of Formula Va or Vb, respectively is advantageously carried out by the coupling of the galactopyranoside or glucopyranoside of Formula IVa or Formula IVb, respectively with the azido alcohol of Formula IIIa and removal of the acetyl blocking groups with sodium methoxide as shown in Reaction Scheme 2. In a preferred embodiment, the azido alcohol of Formula III wherein $R^5$ is benzoyl is illustrated in Reaction Scheme 2 and in subsequent Reaction Schemes 3, 4, 5, 6 and 7. The use of $R^5$ being benzoyl is for illustration purposes only and is not intended to be limiting. The fully protected (blocked) pyranoside of Formula IVa and IVb are readily prepared from the corresponding penta-O-acetyl of galacto- or glucopyranoside as illustrated in Reaction Scheme 2.

The process for the preparation of sulfated β-glycolipids of Formula I are conveniently illustrated and summarized in Reaction Schemes 3, 4, 5, 6 and 7. When it is desired to prepare a disulfated carbohydrate glycolipid of Formula I, the possible combinations of the instant invention are set forth in Reaction Schemes 3, 4 and 5. It should be appreciated by those skilled in the art that selective blocking and deblocking of carbohydrates which are used to prepare the various positional sulfated isomers as well-known in the art such as those illustrated herein and in *Protective Groups in Organic Synthesis,* second ed., T. W. Greene and P. G. M. Wuts, John Wiley & Sons, New York, 1991, Chapter 2 and references therein. It should further be appreciated by those skilled in the art that the specific blocking group to be used will vary with the axial or equatorial position of the hydroxyl groups in the preferred carbohydrate moiety of the instant invention. Thus, Reaction Scheme 3 exemplifies the preparation of the 2,4-disulfate, 2,3-disulfate and 4,6-disulfate glycolipids of galacto and gluco pyranosides of Formula I, respectively. The sequence in Reaction Scheme 4 exemplifies the preparation of 3,4-disulfate, 2,6-disulfate and 3,6-disulfate glycolipids of galacto pyranosides of Formula I and Reaction Scheme 5 exemplifies the preparation of 3,4-disulfate, 3,6-disulfate and 2,6-disulfate glycolipids of gluco pyranosides of Formula I, respectively. Moreover, the preparation of the trisulfated glycolipids of Formula I are illustrated in Reaction Scheme 6 for the preparation of 3,4,6-trisulfate and 2,4,6-trisulfate glycolipids of galacto and gluco pyranosides of Formula I and Reaction Scheme 7 exemplifies the preparation of 2,3,4-trisulfate and 2,3,6-trisulfate glycolipids of galacto and gluco pyranosides of Formula I. The fully tetrasulfated glycolipids of Formula I may be prepared by the general procedures described herein and variations thereof.

In the process for the preparation of sulfated β-glycolipids of Formula I several known procedures are contemplated which generally follow the sequence of reaction steps as illustrated in Reaction Schemes 3, 4, 5, 6 and 7. Each reaction step is generally well-known to those skilled in the art and, advantageously, the appropriate use of protecting (blocking) groups are used when necessary to effect the desired results. In the compounds of Formula I, the $R^2$, $R^3$, $R^4$, $R^5$ and $R^6$ substituents may also be changed by standard well-known procedures to achieve a different but desirable modification of the compounds of Formula I. This is conveniently illustrated in the reaction scheme by the double arrows indicating that the chemical structures may be interchanged by well-known hydrolysis and esterification or etherification procedures. It should be understood by those skilled in the art that the selection and therefore the result will depend on the nature, number and position of the substituents. It should also be understood that the illustration in the schemes is not intended to be limiting since slight modifications are often deemed desirable or necessary to achieve a particular result.

As used herein and in the reaction schemes the term "reduction" is intended to include well-known reduction procedures for the azido group such as hydrogenolysis with hydrogen and palladium; hydrogen transfer reactions with cyclohexane/formic acid/palladium, and preferably with hydrogen sulfide in aqueous pyridine.

As used herein and in the reaction schemes the term "acylation" is intended to include conventional and well-known acylation procedures for the preparation of amides such as the use of leaving groups and activating groups on the acyl portion of the fatty acid. For example, the use of acid chlorides and carbodiimide as activating groups in an organic solvent such as tetrahydrofuran, dichloromethane or mixture of aqueous-organic solvents in the presence of a base such as triethylamine, pyridine, dimethylaminopyridine and 50% sodium acetate.

As used herein and in the reaction schemes the term "sulfation" is intended to include conventional sulfation procedures with sulfur trioxide and usually as a complex with trimethylamine or pyridine in a solvent such as dimethylformamide, pyridine and the like. Advantageously, an excess of sulfur trioxide is utilized to sulfate the desired hydroxy groups while the hydroxy groups to be retained are blocked (protected).

As used herein and in the reaction schemes the terms "blocking" and "protecting" are intended to include conventional and well-known protecting groups in the art such as those illustrated herein and in *Protective Groups In Organic Synthesis,* second ed., T. W. Greene and P. G. M. Wuts, John Wiley and Sons, New York, 1991, Chapter 2 and references therein. For example, the use of acetals and ketals with an acid catalyst; the use of trisubstituted organosilyl reagents such as tert-butyldimethylsilyl chloride and triethylsilyl chloride; methoxymethyl bromide; benzyl bromide; benzoyl chloride and the like. The reaction may be carried out in tetrahydrofuran, dichloromethane, dimethyl formamide and the like in the presence of a base such as triethylamine, dimethylaminopyridine, pyridine, sodium hydride and the like, and optionally with imidazole as a catalyst.

As used herein and in the reaction schemes, the term "hydrolysis" is intended to include conventional hydrolysis procedures well-known to those skilled in the art. For example, the hydrolysis of benzylidene, isopropylidene, p-methoxybenzyl (PMB), methoxymethyl (MOM) and the like may be carried out under acidic conditions such as 90% trifluoroacetic acid, 3N hydrochloric acid, p-toluene sulfonic acid and the like in solvents such as dichloromethane and tetrahydrofuran. Also, p-methoxybenzyl may be removed with the use of dichlorodihydroxyquinone. Furthermore, organosilyl blocking groups such as tert-butyldimethylsilyl and triethylsilyl may advantageously be removed by the use of tetrabutylammonium fluoride (TBAF) in tetrahydrofuran and acetic acid. Still further, benzoate and acetate blocking groups may also be removed by the use of sodium or potassium alkoxides.

The compounds of Formula Ia to If wherein R, $R^1$, $R^2$, $R^3$, $R^4$, $R^5$ and $R^6$ are as previously defined may be prepared from the β-pyranosides of Formula Va or Vb following the sequence of reactions illustrated in Reaction Scheme 3. It should be appreciated by those skilled in the art that the choice of reaction route will depend on the desired compounds of Formula I to be prepared and the appropriate selection of the corresponding starting material. To elaborate on the processes of Reaction Scheme 3, the β-galacto compound of Formula Va is treated with benzaldehyde dimethylacetal and an acid catalyst to block and protect the 4 and 6-position hydroxy moieties to give the corresponding β-galacto pyranoside of Formula VI.

When it is desired to prepare the 2,3-disulfate galacto compound of Formula Ib, the intermediate of Formula VI is subjected to reduction of the azido group and then the acylation of the resulting amino group with the desired activated acyl residue of a fatty acid having the definitions of R as defined herein. The resulting pyranoside is then sulfated in the 2 and 3-position of the carbohydrate moiety by treatment with an excess of sulfur trioxide trimethylamine complex and then basified with an inorganic base such as sodium bicarbonate, potassium bicarbonate, calcium carbonate and the like. The resulting sodium salt of the sulfated and protected intermediate is subjected to conventional hydrolysis to remove the benzylidene protecting group and, if desired, the benzoyl protecting group. It should be appreciated by those skilled in the art that the removal and insertion of the desired $R^4$, $R^5$ and $R^6$ moieties in the compound of Formula Ib can be interchanged, or left untouched depending on the particular substituent which is desired in the preparation of compounds having the sulfate moiety in the 2 and 3-position of the β-galacto compounds of Formula Ib. It should be understood that by following the general sequence steps outlined above the 2,3-disulfated gluco compounds of Formula Ie can be prepared from the corresponding β-gluco pyranoside of Formula Vb.

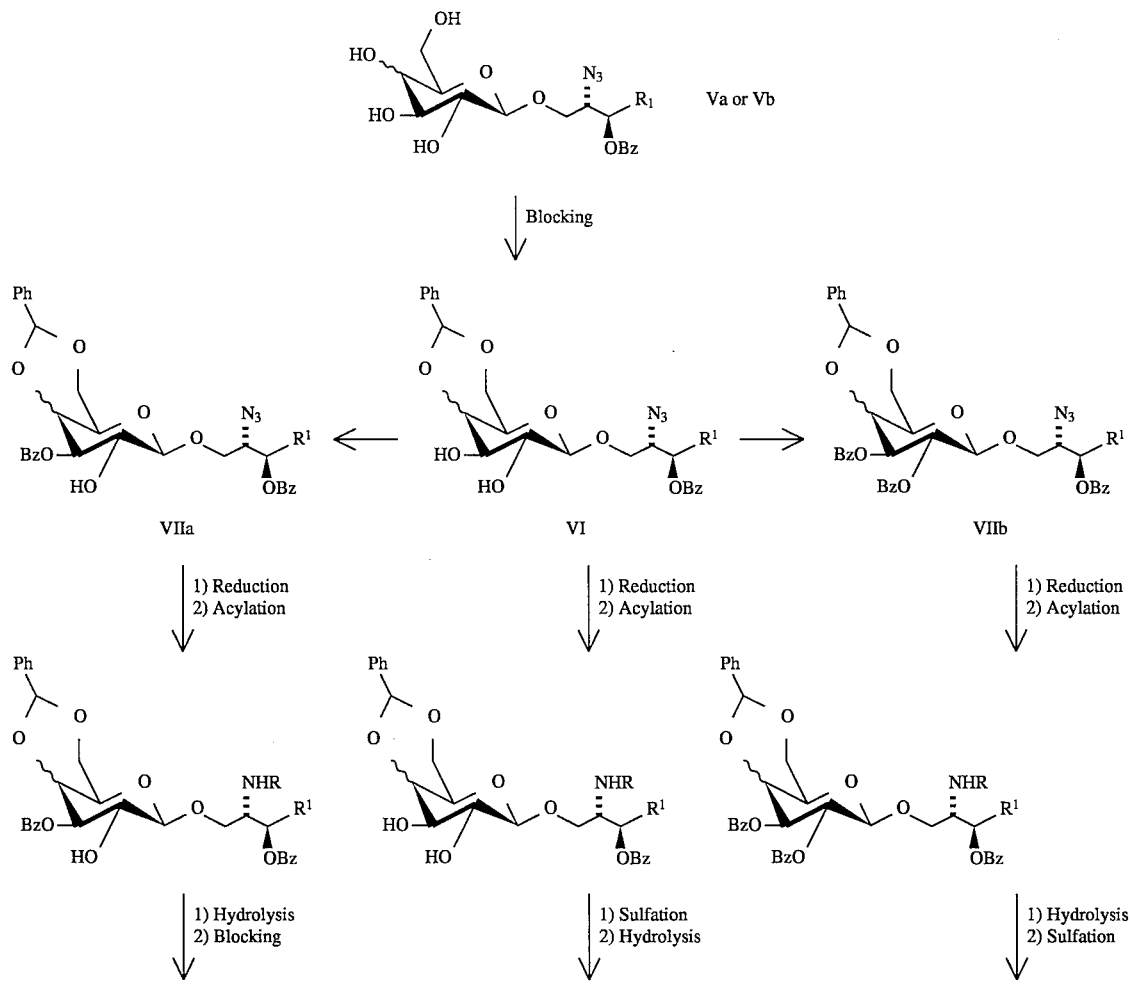

Reaction Scheme 3

-continued
Reaction Scheme 3

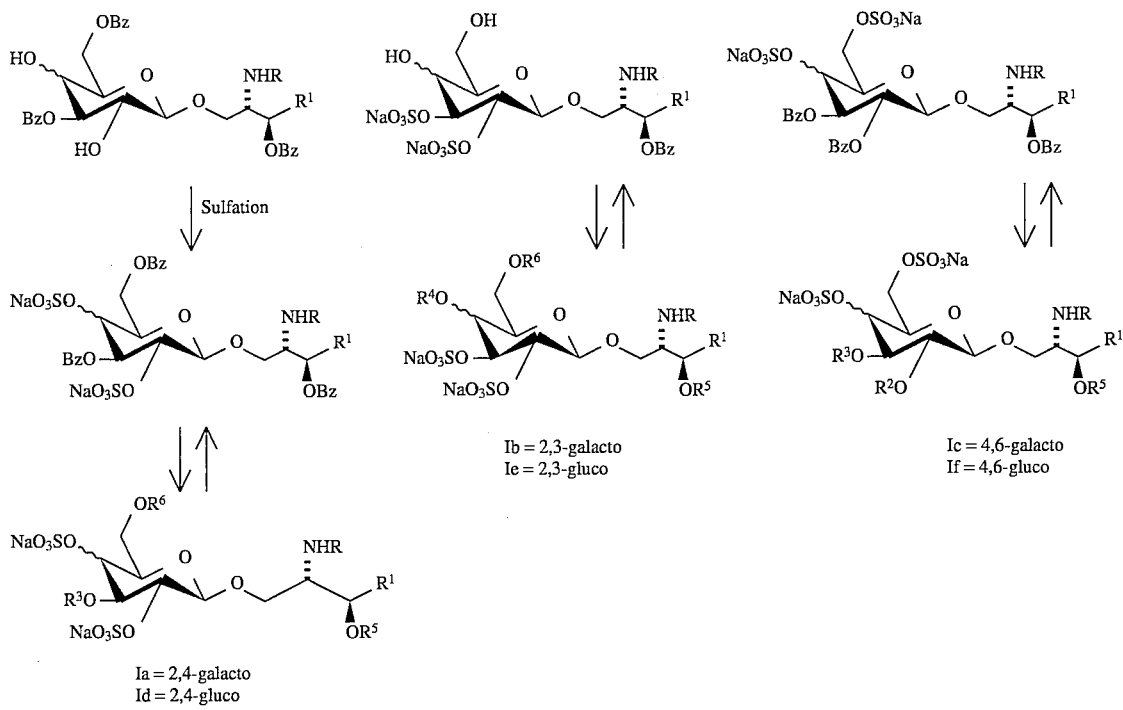

Ia = 2,4-galacto
Id = 2,4-gluco

Ib = 2,3-galacto
Ie = 2,3-gluco

Ic = 4,6-galacto
If = 4,6-gluco

To prepare the 2,4-disulfated compounds of Formula Ia and Id, the corresponding pyranoside of Formula VI is selectively blocked with a protecting group and preferably with a benzoyl moiety by known methods and methods described by K. Jansson et al in *J. Org. Chem.*, 53, 5629–5647 (1988) to give compounds of Formula VIIa. The azido group of compound VIIa is reduced and then acylated with the desired fatty acid residue as described herein. The benzylidene moiety of the resulting intermediate is hydrolyzed and the resulting primary alcohol is blocked by esterification with a benzoyl group. The 3,6-blocked pyranoside is then subjected to sulfation of the remaining 2,4-dihydroxy groups and then, if desired, hydrolyzed to remove one or more of the blocking groups to produce the corresponding 2,4-disulfated galacto and gluco compounds of Formula Ia and Id, respectively.

To prepare the 4,6-disulfated compounds of Formula Ic and If, the corresponding pyranoside of Formula VI is blocked with a protecting group and preferably with a benzoyl moiety to produce a compound of Formula VIIb. The azido group of the protected pyranoside of Formula VIIb is reduced and the resulting amino group acylated with the desired activated acyl residue of a fatty acid. The resulting pyranoside is subjected to conventional hydrolysis to remove the benzylidene protecting group and the 4 and 6-position hydroxy groups are then sulfated as described herein to produce the desired inhibitor of selectin-mediated cell adhesion. The resulting sodium salt of the sulfated and blocked β-glycolipid may, if desired, be hydrolyzed to selectively remove the $R^2$, $R^3$ and $R^5$ blocking groups and then replaced with other substituents by methods known in the art in the preparation of compounds having the sulfate moiety in the 4 and 6-position of the β-galacto compounds of Formula Ic. Similarly, by following the general sequence steps outlined above, the compounds of Formula If can be prepared from the corresponding β-gluco pyranoside of Formula Vb.

To elaborate on the process of Reaction Scheme 4, the β-galacto compound of Formula Va is treated with 2,2-dimethoxypropane and an acid catalyst to protect and block the 3 and 4-position hydroxy moieties to give the corresponding β-galacto pyranoside of Formula VIII.

Reaction Scheme 4

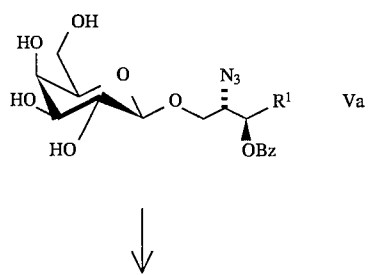

Va

↓

-continued
Reaction Scheme 4

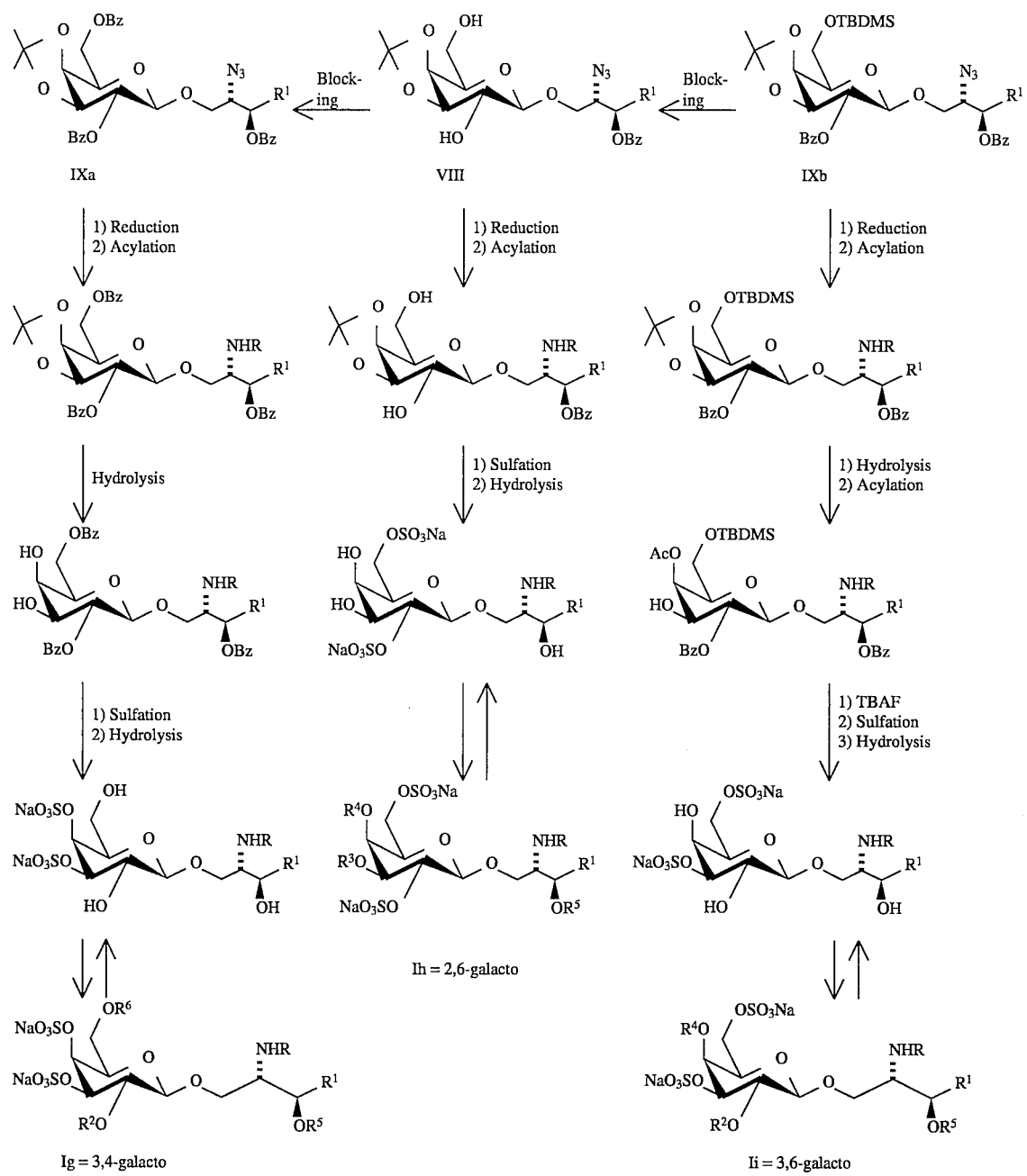

Ih = 2,6-galacto

Ig = 3,4-galacto

Ii = 3,6-galacto

When it is desired to prepare the 2,6-disulfate galacto compound of Formula Ih, the intermediate of Formula VIII is subjected to reduction of the azido group and then acylation to incorporate the desired acyl residue of a fatty acid wherein R is as defined above. The β-glycolipid is sulfated in the 2 and 6-position of the carbohydrate moiety by treatment with excess sulfur trioxide pyridine complex and the resulting salt is subjected to conventional hydrolysis to remove the isopropylidene protecting group. It should be appreciated by those skilled in the art that the desired $R^3$, $R^4$ and $R^5$ substituents may then be inserted in the compounds having the sulfate moiety in the 2 and 6-position to produce the β-galacto compounds of Formula Ih.

To prepare the 3,4-disulfate galacto compounds of Formula Ig, the intermediate of Formula VIII is treated with a blocking group and preferably with a benzoyl moiety by known methods to give compounds of Formula IXa. The azido group is reduced and then acylated as previously described and the resulting pyranoside is subjected to selective hydrolysis to remove the isopropylidene group. The resulting unblocked 3 and 4-position hydroxy groups are sulfated and the remaining blocked hydroxy groups may, if desired, be removed or exchanged for other $R^2$, $R^5$ and $R^6$ substituents which is desired in the compounds having a sulfate moiety in the 3 and 4-position to produce the β-galacto compounds of Formula Ig.

To prepare the 3,6-disulfated galacto compounds of Formula Ii, the intermediate of Formula VIII is selectively treated with two different blocking groups. It is advantageous to first block the primary alcohol group in the 6-position with a triorganosilyl group such as tri ($C_1$–$C_6$) alkylsilyl and triarylsilyl and, preferably, with a t-butyldimethylsilyl group. The secondary hydroxy group may then be advantageously blocked with other conventional groups such as a benzoyl group to produce the compound of Formula IXb. The azido group is reduced and then acylated with the desired acyl residue of a fatty acid and the resulting fully protected glycolipid is selectively hydrolyzed to remove the isopropylidene protecting group. The 4-position hydroxy group is selectively blocked by acetylation and the 6-position silyl protecting group is then removed by standard procedures such as with tetrabutylammonium fluoride. The available 3,6-dihydroxy moieties are now advantageously sulfated by the general procedures described herein and the resulting 3,6-disulfated galacto compound may, if desired, be hydrolyzed to produce a compound wherein $R^2$, $R^4$ and $R^5$ are hydrogen or $R^2$, $R^4$ and $R^5$ may be acylated to produce the 3,6-disulfated galacto compounds of Formula Ii.

Alternatively, the preparation of gluco compounds of 3,4-disulfate, 3,6-disulfate and 2,6-disulfate of Formula I may be carried out from the corresponding β-gluco pyranoside of Formula Vb following the reaction sequences outlined in Reaction Scheme 5. To elaborate on the processes of Reaction Scheme 5, the β-gluco compound of Formula Vb is treated with a blocking group and advantageously with benzaldehyde dimethylacetal to block the 4 and 6-position hydroxy groups and give the corresponding pyranoside intermediate of Formula X. The partially blocked intermediate of Formula X is then selectively blocked with a protecting group and preferably with a benzoyl moiety by methods similar to the procedure described by K. Jansson et al in *J. Org. Chem.*, 53, 5629–5647 (1988) to give compounds of Formula XIa and XIb.

When it is desired to prepare the 2,6-disulfated gluco compound of Formula Il, the corresponding gluco intermediate of Formula XIb is first blocked with a different blocking group such as a methoxymethyl group before the benzylidene moiety is hydrolyzed. The resulting intermediate is then sequentially treated with blocking groups wherein the primary alcohol is first blocked with an organosilyl group such as t-butyldimethylsilyl and then the secondary alcohols are blocked by esterification with a benzoyl group. The azido group of the fully protected pyranoside is reduced and then acylated with the desired fatty acid residue as described herein. The resulting protected glycolipid is subjected to selective hydrolysis to remove both the silyl and methoxymethyl protecting groups by known procedures. The 3,4-blocked pyranoside is then sulfated in the 2 and 6-position as described previously and then, if desired, hydrolyzed to remove one or more of the blocking groups to produce the corresponding 2,6-disulfated gluco compounds of Formula II.

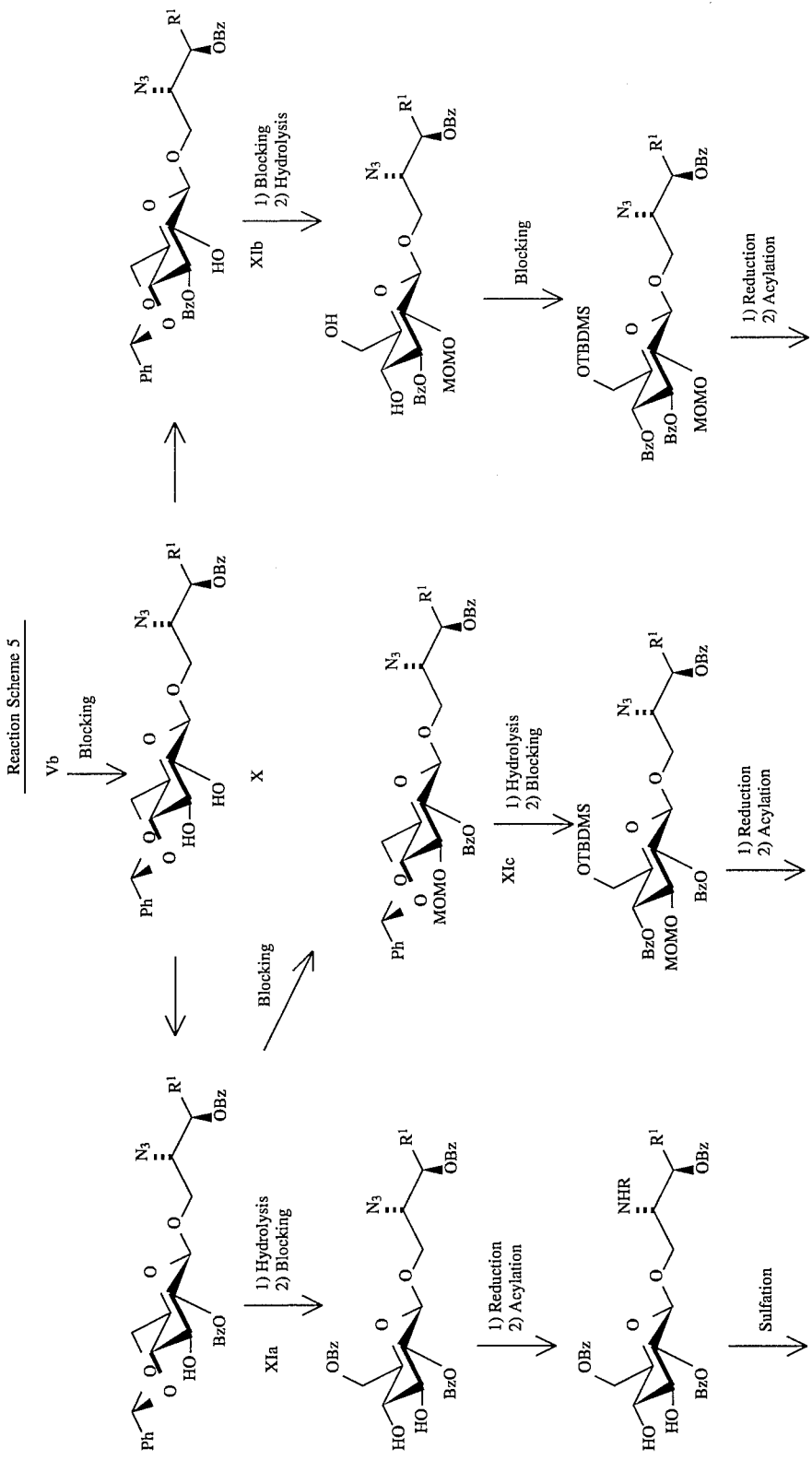

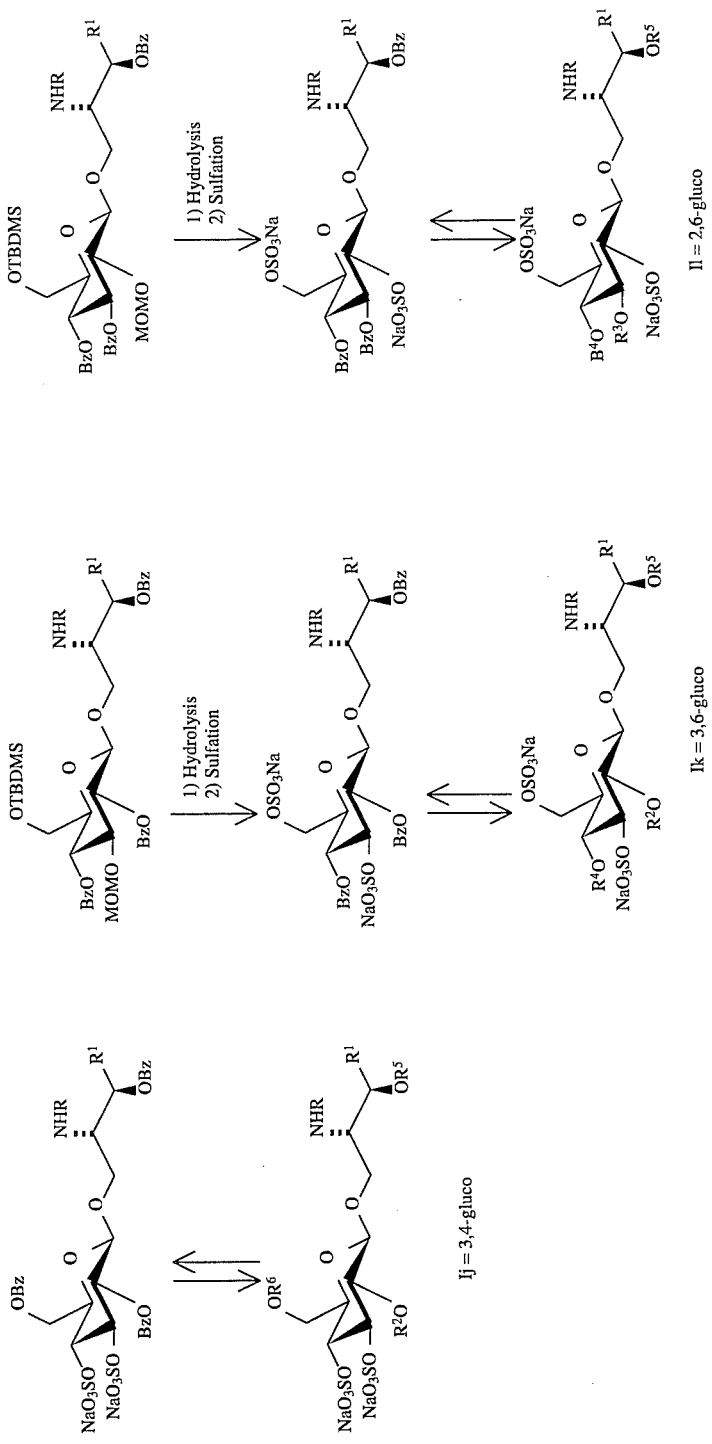

To prepare the 3,4-disulfated gluco compounds of Formula Ij, the corresponding gluco intermediate of Formula XIa is hydrolyzed to remove the benzylidene blocking group and then the resulting primary alcohol in the 6-position is blocked by selective esterification with a benzoyl group. The azido group is reduced and then acylated with the desired fatty acid residue and the resulting intermediate is subjected to treatment with sulfur trioxide complex to sulfate the 3 and 4-position and, if desired, optionally hydrolyzed to remove one or more of the blocking groups to produce the 3,4-disulfated gluco compounds of Formula Ij.

To prepare the 3,6-disulfated gluco compounds of Formula Ik, the corresponding gluco intermediate of Formula XIa is further blocked with a different blocking group such as a methoxymethyl group to produce the compound of Formula XIc. Hydrolysis of the benzylidine group followed by the sequential protection of the primary and secondary alcohol groups with an organosilyl and then a benzoyl group as described above and illustrated in Reaction Scheme 5 will produce a fully protected pyranoside compound in which the azido group is reduced and then acylated with the desired fatty acid residue. The fully protected glycolipid is subjected to selective hydrolysis to remove both the silyl and methoxymethyl groups by known procedures and the resulting 3 and 4-position hydroxy groups are sulfated with sulfur trioxide complex as generally described herein. The 3,6-disulfated gluco is optionally hydrolyzed to give the 3,6-disulfated gluco compounds of Formula Ik.

The general processes for the preparation of trisulfated galacto and gluco compounds of Formula Im to Ip and Formula Iq to It from the appropriate starting materials are illustrated in Reaction Schemes 6 and 7. In Reaction Scheme 6, the preparation of 3,4,6-trisulfate and 2,4,6-trisulfate compounds for the galacto and gluco glycolipids of Formula Im to Ip wherein R, $R^1$, $R^2$, $R^3$ and $R^5$ are as previously defined may be prepared from the compound of Formula XII following the general sequence of reactions outlined in Reaction Scheme 6. The preparation of the 3,4,6-trisulfate galacto and gluco compounds of Formula Im and Io, respectively may be prepared from the corresponding galacto and gluco intermediates of Formula XII by the general procedures illustrated in Reaction Scheme 6.

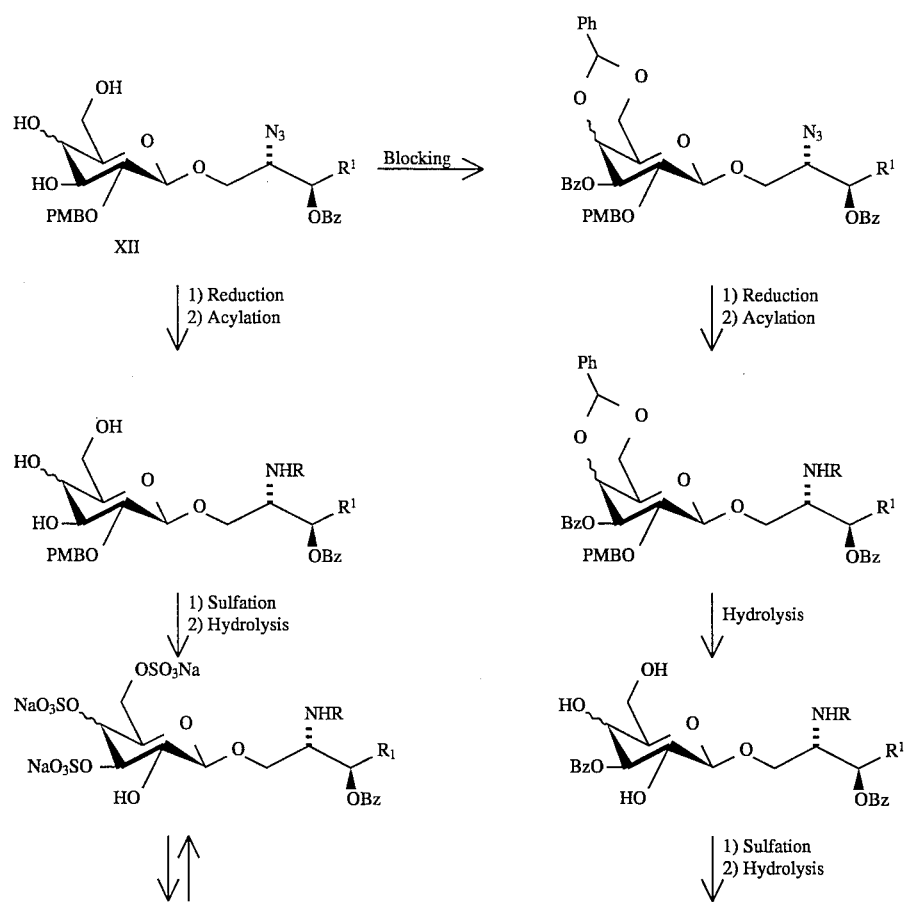

-continued
Reaction Scheme 6

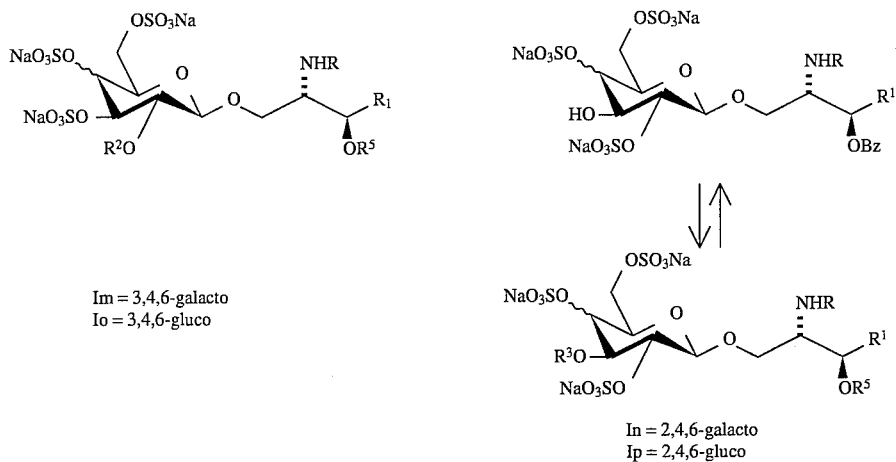

Im = 3,4,6-galacto
Io = 3,4,6-gluco

In = 2,4,6-galacto
Ip = 2,4,6-gluco

To prepare the 2,4,6-trisulfate compounds of Formula In and Ip, the corresponding galacto and gluco compound of Formula XII is selectively treated with two different blocking groups. It is advantageous to first treat the compound of Formula XII with a blocking group such as benzaldehyde dimethylacetal to block the 4 and 6-position hydroxy groups and then with a second blocking group such as benzoyl group by methods previously described. The azido group of the protected pyranoside is reduced and then acylated with the desired fatty acid residue as described herein. The resulting pyranoside is subjected to hydrolysis to remove both the benzylidene and p-methoxybenzyl blocking groups by procedures known in the art. The unblocked pyranoside is then treated with an excess of sulfur trioxide pyridine complex and then basified with an inorganic base such as sodium bicarbonate. The resulting 2,4,6-trisulfate compound may, if desired, be subjected to conventional hydrolysis to remove the blocking groups to produce compounds of the Formula In or Ip.

In Reaction Scheme 7, the preparation of 2,3,4-trisulfate and 2,3,6-trisulfate compounds for the galacto and gluco glycolipids of Formula Iq to It wherein R, $R^1$, $R^4$, $R^5$ and $R^6$ are as previously defined may be prepared from the corresponding compounds of Formula Va or Vb, respectively by the general procedures outlined in Reaction Scheme 7.

When it is desired to prepare the 2,3,4-trisulfate compounds of Formula Iq or Is, the primary alcohol of the compound of Formula Va or Vb is first esterified with a blocking group such as benzoyl and then the azido group is reduced and acylated with a fatty acid. The resulting pyranoside which is blocked in the 6-position is treated with sulfur trioxide pyridine complex and then basified with sodium bicarbonate to give a 2,3,4-trisulfate pyranoside which is then optionally hydrolyzed to produce 2,3,4-trisulfate compounds of Formula Iq or Is.

Reaction Scheme 7

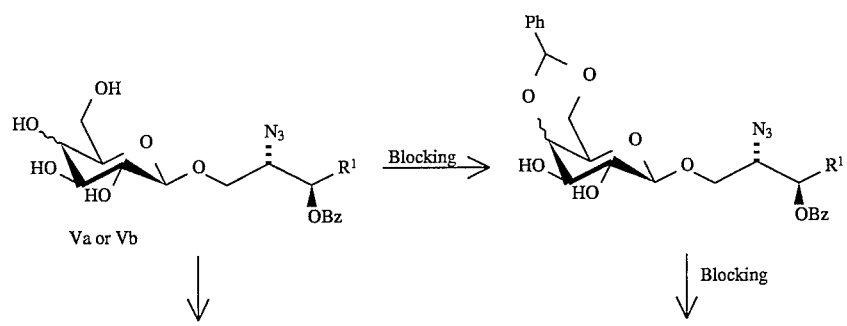

-continued
Reaction Scheme 7

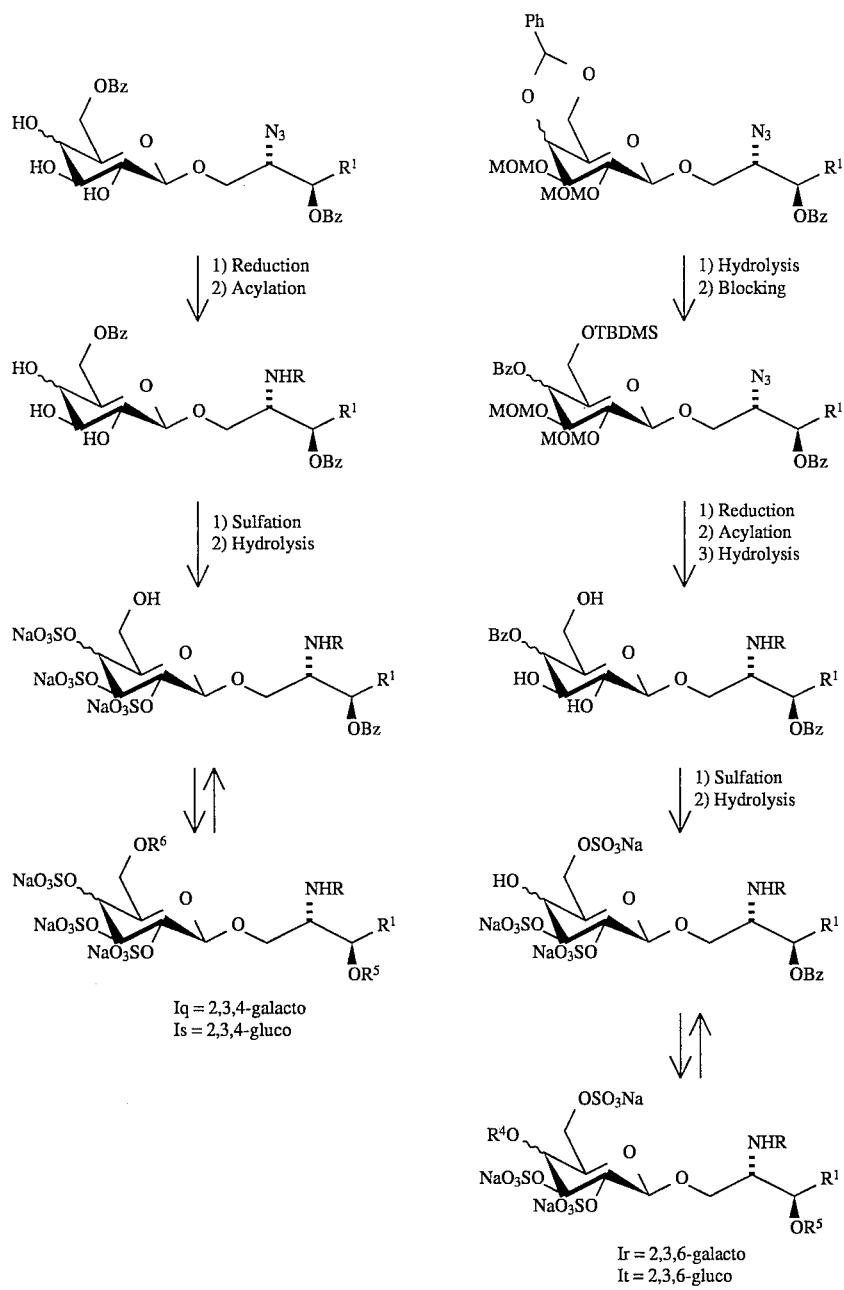

To prepare the 2,3,6-trisulfate compounds of Formula Ir or It, the corresponding galacto or gluco intermediates of Formula Va or Vb is selectively treated with two different blocking groups such as with benzylidene and then methoxymethyl blocking moieties. The resulting protected pyranoside is selectively hydrolyzed to remove the benzylidene blocking group and then the primary alcohol is protected with an organosilyl protecting group while the hydroxy in the 4-position is blocked with a benzoyl moiety. The azido group is then reduced and acylated with the desired fatty acid residue as previously described. Once the hydroxy group in the 4-position is selectively blocked by a group which is different from the other hydroxy blocking groups, the blocking groups such as the t-butyldimethylsilyl and the methoxymethyl groups are removed by known procedures.

The resulting pyranoside is treated with excess sulfur trioxide complex and then optionally hydrolyzed as shown in Reaction Scheme 7 to produce compounds of the Formula Ir or It.

The process for the preparation of tetrasulfate galacto and gluco compounds of Formula I wherein R, $R^1$ and $R^5$ are as previously described may be prepared from the corresponding intermediates of Formula Va or Vb by the general procedures described and illustrated herein.

In a preferred embodiment of the invention the compounds of Formula I have the formula

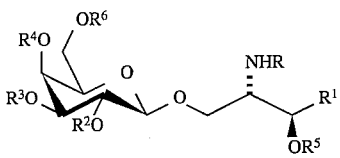

wherein R is an acyl residue of a fatty acid; $R^1$ is —(CH=CH)$_m$—(CH$_2$)$_n$—CH$_3$; $R^2$, $R^3$, $R^4$ and $R^6$ are independently at least two —SO$_3$H; $R^2$, $R^3$, $R^4$, $R^5$ and $R^6$ each are independently hydrogen, unsubstituted or substituted alkanoyl, arylalkyl or arylcarbonyl wherein said substitutent is selected from halogen, $C_{1-4}$ alkyl, trifluoromethyl, hydroxy and $C_{1-4}$ alkoxy; or $R^4$ and $R^6$, taken together is benzylidene or $R^3$ and $R^4$, taken together is isopropylidene; m is an integer of 0 or 1; n is an integer of from 5 to 14, inclusive; or a nontoxic pharmaceutically acceptable salt, solvate or hydrate thereof. In a particularly preferred embodiment, $R^2$, $R^3$, $R^4$ and $R^6$ are independently two —SO$_3$H. In a further particularly preferred embodiment, $R^2$, $R^3$, $R^4$, $R^5$ and $R^6$ each are independently hydrogen or benzoyl.

In another preferred embodiment of the invention the compounds of Formula I have the formula

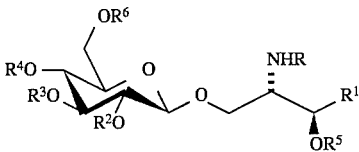

wherein R is an acyl residue of a fatty acid; $R^1$ is —(CH=CH)$_m$—(CH$_2$)$_n$—CH$_3$; $R^2$, $R^3$, $R^4$ and $R^6$ are independently at least two —SO$_3$H; $R^2$, $R^3$, $R^4$, $R^5$ and $R^6$ each are independently hydrogen, unsubstituted or substituted alkanoyl, arylalkyl or arylcarbonyl wherein said substitutent is selected from halogen, $C_{1-4}$ alkyl, trifluoromethyl, hydroxy and $C_{1-4}$ alkoxy; or $R^4$ and $R^6$, taken together is benzylidene or $R^3$ and $R^4$, taken together is isopropylidene; m is an integer of 0 or 1; n is an integer of from 5 to 14, inclusive; or a non-toxic pharmaceutically acceptable salt, solvate or hydrate thereof. In a particularly preferred embodiment, $R^2$, $R^3$, $R^4$ and $R^6$ are independently two —SO$_3$H. In a further particularly preferred embodiment, $R^2$, $R^3$, $R^4$, $R^5$ and $R^6$ each are independently hydrogen or benzoyl.

In another aspect, this invention provides a method for the treatment or prevention of diseases mediated by the inhibition of selectin-mediated cellular adhesion in a mammal in need thereof, which comprises administering to said mammal a therapeutically effective amount of a compound of Formula I or a non-toxic pharmaceutically acceptable salt, solvate or hydrate thereof. In a particularly preferred embodiment, this invention provides a method for the treatment of inflammatory related diseases or other pathological conditions in a mammal in need thereof, which comprises administering to said mammal a therapeutically effective amount of a compound of Formula I or a non-toxic pharmaceutically acceptable salt, solvate or hydrate thereof.

In still another aspect, this invention provides pharmaceutical compositions comprising at least one compound of Formula I in combination with a pharmaceutical carrier or diluent.

CELL ADHESION ACTIVITY

1. P-Selectin Adhesion Receptor Binding

P-selectin (GMP140, granule membrane protein-140, PADGEM, or CD62) is a calcium-dependent transmembrane protein found in alpha granules of endothelial cells and platelets. It is an inducible selectin produced on activated endothelium and platelets which recognize alpha(2–3)sialylated and alpha(1–3)fucosylated lactosaminoglycans which include the sequence, Lewis x (Zhou et al., *J. Cell. Biol.,* (1991) 115 (2): 557–564) and sulfatides (3-sulfated galactosyl ceramides, Aruffo, et al., *Cell* (1991) 67: 35–44). P-selectin may be responsible for the initial adhesion events between endothelium and neutrophils as evidenced by leukocyte rolling induced by P-selectin in flow cells (Lawrence, M., and T. Springer, *Cell* (1991) 65: 859–873).

Based on the availability of soluble forms of P-selectin prepared as described by Aruffo, A., et al., *Cell,* 67, 35–44 (1991), a binding ELISA based assay modified from Foxall, et al., *J., Cell Biol.,* 117, 895–902 (1992) was developed to measure inhibitors of P-selectin binding to immobilized sulfatides. Such inhibitors were tested in the assay described below.

0.1 ml of sulfatide (SIGMA) or lysosulfatide (SIGMA) each at 1 µg/ml in MeOH were added to the wells of a 96-well ELISA plate (ProBind, Falcon) and allowed to dry overnight at room temperature. The next day the antigen coated plates were blocked for 1.5 hours at room temperature with 5% BSA (ICN) in buffer containing 20mM Hepes and 0.15 M NaCl, pH 8.0. Wild type P-selectin and mutants thereof were first mixed with HRP-conjugated goat anti-human IgG (Fisher Scientific), serially diluted and then incubated for 30 minutes at 37° C. in buffer containing 20 mM Hepes, 0.15 M NaCl, 1% BSA and 0.8 mM CaCl$_2$, pH 8.0 prior to addition to the BSA blocked plates. Following the 30 minute preincubation, the fusion protein-HRP conjugate immunocomplexes were incubated on the blocked antigen coated plates for 45 minutes at 37° C. in the presence or absence of the test compounds and then washed to remove any unbound proteins. Bound complexes were detected by addition of substrate buffer (95 mM NaOAc.3H$_2$O, 5 mM citric acid monohydrate, 1.4 mM urea/H$_2$O$_2$) containing 3, 3', 5, 5' Tetramethylbenzidine (SIGMA). Reactions were stopped by the addition of 3N sulfuric acid and the absorbance read on an ELISA reader at dual wavelengths 450 and 630 nm. The efficacy of these compounds was compared to that of sulfatide (positive control) or to lysosulfatide (negative control). The data is obtained as percent inhibition of specific binding $$\% \text{ Inhibition} = \left[ 1 - \left( \frac{\text{Specific binding: Test Compound}}{\text{Specific binding: Vehicle}} \right) \right] \times 100$$

and a plot of dose vs. percent inhibition of Rg binding is generated in which IC$_{50}$(µM) is calculated and reported as cell free data in Table 1.

2. HL-60 Cell Binding to P- and E-Selectin RG Receptor globulin (Rg) Construction The chimeric P-and E-selectin receptor globulin (Rg) consists of the human lectin domain, the EGF domain, and two complement repeats of the human selectins fused to the hinge, CH1 and CH2 domains of human IgG1. These proteins were prepared as described by Aruffo, et al., *Cell* (1991) 67: 35–44; Walz, et al., *Science* (1990) 250, 1132–1135.

Cell binding assay for Rg

The HL-60 cell line, obtained from the American Type Culture Collection, ATCC No. CCL240, was employed to investigate P-selectin Rg binding. Assays were done in 96-well tissue culture dishes. The wells were first coated with 0.5 ug goat anti-human Fc antiserum overnight, and nonspecific binding sites were blocked by incubation of the wells with 1% nonfat dry milk in phosphate buffered saline (PBS containing 0.9 mM $CaCl_2$ and 0.8 mM $MgSO_4$) for 30 minutes. The Rg was then bound to the anti Fc-coated wells by incubating 50 ng in 50 ul of PBS for two hours. Cells, washed twice and resuspended in PBS to remove traces of medium components, were labeled with 10 uM calcein acetoxy methyl ester for 30 minutes at $3 \times 10^7$ cells per ml at room temperature. Serum-containing medium (RPMI with 20% fetal calf serum) was added, and the cells washed, followed by resuspension in PBS and a further spin. The labeled cells, resuspended in PBS, were added to twice washed Rg-containing wells at 200,000 per well. Following a 30 minute incubation with slow shaking, the wells were aspirated and washed three times with PBS to remove unbound cells. To certain wells were added known numbers of cells for determination of a standard curve of fluorescent units per cell. The fluorescence on the plate was quantitated using a fluorescent plate reader. Following subtraction of a blank representing the binding of cells to non-Rg containing wells (<5000 cells), the specific binding to P- or E- selectin was determined.

Inhibitors of cell binding

Test compounds were prepared by dissolution to a final concentration of 20 mg/ml in dimethyl sulfoxide (DMSO), diluted in PBS to 2 mg/ml, and briefly sonicated prior to use. The Rg coated wells were preincubated at room temperature for 15 minutes with the inhibitor, and 200,000 cells were added to yield the final indicated inhibitor concentration in 160 ul of PBS. The data is obtained as percent inhibition of specific binding:

$$\% \text{ Inhibition} = \left[ 1 - \left( \frac{\text{Specific binding: Test Compound}}{\text{Specific binding: Vehicle}} \right) \right] \times 100$$

and a plot of dose vs. percent inhibition of Rg binding is generated in which $IC_{50}$ (µM) is calculated and reported in Table 1.

3. Reverse Passive Arthus Reaction in Rats

The reverse passive Arthus reaction in rats is a modification of the method by Mulligan et al., as described in *J. Clin. Invest.*, (1991) 88:1396–1406. This is an experimental model in which the interaction of antigen-antibody complexes and complement leads to a severe vasculitis that is associated with edema, induration, erythema and hemorrhage. The interaction between the antigen-antibody complexes and complement leads to a localized influx of neutrophils. These neutrophils release a variety of mediators that are associated with tissue damage and vascular permeability. The localized inflammatory reaction is measured using different techniques i.e., vascular permeability and neutrophil influx which is evaluated both biochemically and microscopically.

Male Sprague Dawley specific pathogen-free rats with jugular vein cannulae (280–320 g, Hill Top Labs, Pa.) are used in these studies. Animals are acclimated for at least 1 day and individually housed in stainless steel cages. The dorsal region of the rats is closely clipped 2 days prior to the experiments and divided into 4 sites on each side of the midline. Prior to all injections the rats are sedated with 0.4 ml per 300 gm rat of ketamine/rompun [1000 mg (10 ml) of ketamine HCL is mixed with 40 mg (2.0 ml) Rompun] administered IP and or inhalation anesthesia with metafane (methoxyflurane).

Bovin Serum Albumin (BSA) and rabbit polyclonal IgG rich in anti-BSA are purchased from Sigma Chemical Co. (St. Louis, Mo.). Radiolabelled $^{125}$I-BSA (spAct 1–5 µCi/µg) is purchased from Dupont NEN (Boston, Mass.).

Each rat is administered intradermal (ID) injection of (0.4 mg, 0.6 mg and 0.8 mg) anti-BSA in a volume of 100 µl per injection in normal saline. The ID injections are randomized near the mid dorsal region on both sides of the back bone. Immediately after the ID injections of the anti-BSA, the rats are administered intravenous (IV) injections of BSA (10 mg in 1.0 ml) in normal saline containing $^{125}$I labeled BSA (1 µCi/ml BSA or 5.0 µCi/kg body wt) for quantification of dermal vascular injury. Anti-inflammatory agents such as inhibitors of adhesion molecules of the present invention are administered IV at a single dose of 3 mg immediately after BSA. Four (4) hours after the IV injection of BSA, the rats are anesthetized with metafane and 2 to 3 ml of blood is withdrawn via the cannula into an anticoagulant containing (EDTA or Heparin) tube and plasma separated and saved for neutrophil and albumin quantitation. The rats are killed and the skin surrounding the injection site (15 mm diameter) is punched out and weighed. The skin samples and a fixed volume of plasma (0.1 to 1.0 ml) is analyzed in a gamma-counter for $^{125}$I content. Skin samples from the contralateral side are processed and analyzed for myeloperoxidase activity (MPO) as a measure of neutrophil accumulation. As needed, samples are also processed for histological evaluation of the reacted sites.

Vascular Permeability (VP)

The calculation of the plasma protein exudation into skin is made by determining the radioactivity in the tissue and relating this to the level of radioactive albumin in the blood at the time of sacrifice. The equation below shows the calculation for microliter plasma extravasated (Issekutz and Issekutz, Pharmacological methods in the control of inflammation, (1989) 129–150).

$$\mu l \text{ plasma extravasated} = \frac{\text{CPM in tissue}}{\text{CPM}/\mu l \text{ plasma}}$$

Percent inhibition of the test compound at 3 mg was determined as follows:

$$\% \text{ Inhibition} = \left[ 1 - \left( \frac{\mu l \text{ plasma extravasated with test compound}}{\mu l \text{ plasma extravasated with vehicle}} \right) \right] \times 100$$

Myeloperoxidase (MPO)

MPO is located in the azurephil granules of polymorphonuclear leukocytes (PMN). Because of its abundance in these cells (5% dry weight), this enzyme is used as a marker for tissue neutrophil content. For tissue MPO content, the method of Bradley, et al., was used as described in *J. Invest. Dermatol.* (1982) 78: 206–209. Biopsies from each treatment group were placed in plastic tubes (15×100 mm) containing 10 ml of 0.5% hexadecyltrimethylammonium bromide (HTAB) in 0.05 M potassium phosphate buffer pH 6.0. The tissue was then homogenized with a Brinkmann Polytron homogenizer (10s). The supernatant (0.05 ml) was assayed by mixing with 0.150 ml o-dianisidine (0.334 mg/ml) and 0.0005% hydrogen peroxide in 0.05 M potassium phosphate buffer pH 6.0 in a 96-well microtiler plate. Change in absorbance at 450 nm was measured at room temperature using a Vmax kinetic plate reader (Molecular Devices, Pale Alto, Calif., USA). Percent inhibition of the test compound at 3 mg dose was determined as follows:

% Inhibition =

$$\left[1 - \left(\frac{\text{Absorbance of test compound treated Biopsies}}{\text{Absorbance of vehicle treated Biopsies}}\right)\right] \times 100$$

The in vive experimental results as measured by vascular permeability (VP) and myeloperoxidase (MPO) at a single dose of the test compound are shown in Table 1.

TABLE 1

| | P-Selectin | | RPA | |
|---|---|---|---|---|
| Example No. | Cell Free $IC_{50}$ (µM) | HL-60 $IC_{50}$ (µM) | VP % Inhib.* | MPO % Inhib.* |
| 1 | 0.1 | NV** | 42 | 24 |
| 2 | 1.7 | 39 | 63 | 33.5 |
| 3 | 0.2 | NV | 34 | 14 |
| 7 | 1 | 11 | 56 | 46 |
| 8 | 1.3 | 15 | NA*** | NA |
| 10 | 0.1 | 10 | 0 | 56 |
| 19 | 0.6–4 | 45 | NA | NA |
| 25 | 2.7 | NV | NA | NA |

*% Inhibition at 3 mg
**not valid
***not available

The biological results of representative compounds according to this invention are shown in Table 1. Both the cell and cell-free in vitro assays and the in vivo tests carried out in the RPA rat model show that the compounds of Formula I are inhibitors of P-selectin mediated binding and, more importantly, confirm that the compounds of the instant invention are selectin inhibitors useful to treat inflammatory conditions in a mammal.

Therefore, the compounds of Formula I or pharmaceutical compositions thereof are useful in the treatment and/or prevention of diseases or other pathological conditions which are mediated by the binding of selectins in cellular adhesion. Such diseases and conditions include acute or chronic inflammatory diseases such as rheumatoid arthritis, asthma, allergy conditions, psoriasis, septic shock, adult respiratory distress syndrome, inflammatory bowel disease and opthalmic inflammatory diseases; autoimmune diseases; thrombosis or inappropriate platelet aggregation conditions, and cardiovascular disease; reperfusion injury; multiple sclerosis and neoplastic disease including metastasis conditions.

In another embodiment, this invention includes pharmaceutical compositions comprising at least one compound of Formula I in combination with a pharmaceutical carrier or diluent.

In still another embodiment, this invention relates to a method of treatment or prevention of diseases or other pathological conditions characterized by selectin-mediated cellular adhesion in a mammal in need thereof, which comprises administering to said mammal a therapeutically effective amount of a compound of Formula I or a non-toxic pharmaceutically acceptable salt, solvate or hydrate thereof.

In yet another embodiment, this invention relates to a method for inhibiting or reducing inflammatory disease processes in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, bronchial, rectal, topical, ophthalmic, intraarticular or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in transdermal formulations with permeation enhancers such as DMSO and iontophoresis. Other topical compositions well-known in the art can be administered to treat dermal inflammation. The pharmaceutical compositions are prepared by conventional techniques appropriate to the desired preparation containing appropriate amounts of the active ingredient, that is, the compound of Formula I according to the invention. See, for example, Remington's Pharmaceutical Sciences, Mack Publishing Company, Easton, Pa. 17th edition, 1985.

The dosage of the compounds of Formula I to achieve a therapeutic effect will depend not only on such factors as the age, weight and sex of the patient and mode of administration, but also on the degree of cell adhesion inhibition desired and the potency of the particular compound being utilized for the particular disorder of disease concerned. It is also contemplated that the treatment and dosage of the particular compound may be similar to the treatment and dosage used with dexamethasone phosphate and that the dosage would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention for the satisfactory inhibition or reduction of selectin-mediated cell adhesion.

A suitable dose of a compound of Formula I or pharmaceutical composition thereof for a mammal suffering from, or likely to suffer from any condition as described herein is an amount of active ingredient from 0.1 µg/kg to 100 mg/kg body weight. For systemic administration, the dose may be in the range of 0.1 to 100 mg/kg body weight to the active ingredient, and preferably, in the range of 0.1 to 50 mg/kg body weight. For topical administration, for example to the skin or eye, a suitable dose of active ingredient may be in the range of 0.1 µg to about 100 mg/ml of liquid carrier or excipient, and preferably, about 0.1 mg to 10 mg/ml. For oral dosing including the treatment of prophylaxis of inflammatory diseases or conditions, a suitable dose may be in the range of about 1 mg to 100 mg/kg of mammal body weight, and preferably, from about 1 mg to about 50 mg/kg body weight. The active ingredient will preferably be administered in equal doses from one to four times a day. However, usually a small dosage is administered, and the dosage is gradually increased until the optimal dosage for the host under treatment is determined.

The following examples are given by way of illustration and are not to be construed as limiting the invention in any way inasmuch as many variations of the invention are possible within the spirit of the invention.

DESCRIPTION OF SPECIFIC EMBODIMENTS

EXAMPLE 1

(2S,3R,4E)-3-Benzoyloxy-2-hexadecanoylamino-1-[2,3di-O-benzoyl-4,6-di-O-(sodium oxysulfonyl)-β-D-galactopyranosyloxy]-4-octadecene A. (2S,3R,4E)-2-Azido-3-benzoyloxy-1-(2,3,4,6-tetra-O-acetyl-α-D-galactopyranosyloxy)-4-octadecene and (2S,3R,4E)-2-azido- 3-benzoyloxy-1-(2,3,4,6-tetra-O-acetyl-β-D-galactopyranosyloxy)-4-octadece

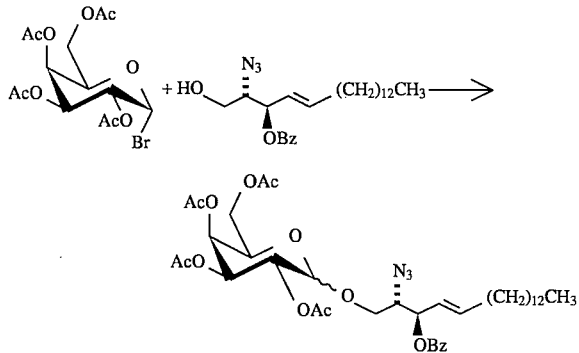

A solution of (2S,3R,4E)-2-azido-3-benzoyloxy-4-octadecen-1-ol (2.9 g, 6.75 mmol) in dry benzene (100 mL) and nitromethane (100 mL) was heated under reflux. Benzene was distillated and the solution was concentrated under vacuum to 50–60 mL. To this solution was added 2,3,4,6-tetra-O-acetyl-α-D-galactosyl bromide [as described in *Methods in Carbohydrate Chemistry*, vol. 1, p. 224–225] (5.0 g, 12.16 mmol) and mercury(11) cyanide (3.0 g, 12.16 mmol) at 22° C. and under argon and the resulting mixture was heated up to 80°–85° C. for 15–20 minutes. The reaction was then cooled down to 5° C. and diluted with ethyl ether/water (1:1,100 mL). Hydrogen sulfide was bubbled in and the resulting black precipitate was filtered on Celite and washed with ethyl ether (3×25 mL). The organic phases were washed with cold aqueous sodium bicarbonate solution (1 M, 4×25 mL), water (25 mL) and brine (25 mL), dried over anhydrous magnesium sulfate, filtered and concentrated. The black resulting residue was purified by chromatography on silica gel (250 g, 0% to 30% ethyl acetate/hexane) and afforded the p-anomer (3.90 g, 76%) and the anomer of the title compound (0.49 g, 9.5%) as colorless oils.

IR (CH$_2$Cl$_2$) $\upsilon_{max}$ (cm$^{-1}$) α-anomer: 3050, 2930 (C-H), 2100 (N$_3$), 1750 (C=O), 1228 (C—O).

IR (CH$_2$Cl$_2$) $\upsilon_{max}$ (cm$^{-1}$) β-anomer: 3050, 2930, 2955 (C—H), 2130 (N$_3$), 1750 (C=O), 1220 (C—O).

$^1$H NMR 400 MHz (CDCl$_3$) δ (ppm) β-anomer: 0.89 (3H, t, J=7.0 Hz, —CH$_3$), 1.25 (20H, br s, —(CH$_2$)$_{10}$—), 1.39 (2H, m, —CH$_2$—), 2.00, 2.01, 2.09, 2.15 (4×3H, 4s, 4×—OCOCH$_3$), 2.09 (2H, m, =CH—CH$_2$—), 3.52 (1H, dd, J=10.7 and 7.7 Hz, H-1), 3.88 (1H, dd, J=10.7 and 3.5 Hz, H-1), 3.91–3.95 (1H, m, H-2), 4.09–4.10 (2H, m, H-6'), 4.24 (1H, td, J=6.5 and 1.1 Hz, H-5'), 5.14–5.17 (2H, m, H-1' and H-2'), 5.34–5.39 (1H, m, H-3'), 5.49 (1H, dd, J=3.3 and 1.1 Hz, H-4'), 5.53–5.60 (2H, m, H-3 and H-4), 5.93–5.99 (1H, m, H-5), 7.45–8.06 (5H, 3m, —C$_6$H$_5$).

$^1$H NMR 400 MHz (CDCl$_3$) δ (ppm) β5-anomer: 0.89 (3H, t, J=7.0 Hz, —CH$_3$), 1.25 (20H, br s, —(CH$_2$)$_{10}$—), 1.39 (2H, m, —CH$_2$—), 2.00, 2.03, 2.11, 2.16 (4×3H, 4s, 4×—OCOCH$_3$), 2.09 (2H, m, =CH—CH$_2$), 3.58–3.63 (1H, m, H-1), 3.89–3.97 (3H, m, H-1, H-5' and H-2), 4.11 (1H, dd, J$_{AB}$=11.2 and J$_{AX}$=6.7 Hz, H-6'), 4.14 (1H, dd, J$_{AB}$=11.2 and J$_{BX}$=6.7 Hz, H-6'), 4.51 (1H, d, J=7.9 Hz, H-1'), 5.02 (1H, dd, J=10.5 and 3.4 Hz, H-3'), 5.42 (1H, dd, J=10.5 and 7.9 Hz, H-2'), 5.39 (1H, d, J=3.4 Hz, H-4'), 5.53–5.62 (2H, m, H-3 and H-4), 5.94 (1H, dt, J=14.3 and 6.9 Hz, H-5), 7.45–8.08 (5H, 3m, —C$_6$H$_5$).

B. (2S,3R,4E)-2-Azido-3-benzoyloxy-1-(β-D-galactopyranosyloxy)-4-octadecene

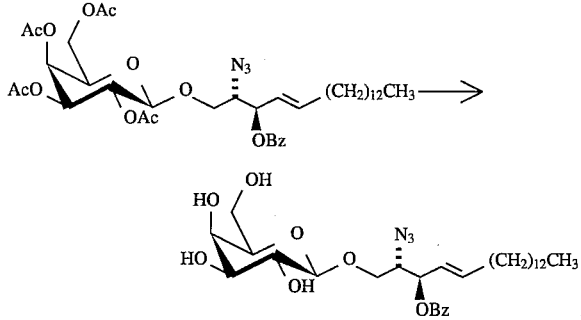

A solution of (2S,3R,4E)-2-azido-3-benzoyloxy-1-(2,3,4,6-tetra-O-acetyl-β-D-galactopyranosyl-oxy)-4-octadecene (4.0 g, 5.26 mmol) in dichloromethane (20 mL) was added slowly to a freshly prepared solution of sodium (2.44 g, 106 mmol) in methanol (120 mL) at −70° C. and under argon. The temperature of the cooling bath was allowed to reach −50° C. during 3 hours. The reaction mixture was cooled down to −70° C. and neutralized with a solution of acetic acid (6.0 mL, 106 mmol) in dichloromethane (10 mL). The mixture was concentrated under vacuum, giving a residue which was dissolved in dichloromethane (50 mL). The residual solid (sodium acetate) was filtered on Celite and washed with dichloromethane (5×10 mL) The combined filtrate and washings were evaporated and the residue was purified by silica gel chromotagraphy (200 g, 0% to 12% methanol/dichloromethane) and afforded the title compound (2.77 g, 89%) as a white solid.

IR (CH$_2$Cl$_2$) $\upsilon_{max}$ (cm$^{-1}$): 3700–3200 (O—H), 3060, 2930,2860 (C—H), 2110 (—N$_3$), 720 (C=O).

$^1$H NMR 400 MHz (DMSO-d$_6$) δ (ppm): 0.85 (3H, t, J=6.8 Hz, —CH$_3$), 1.20–1.65 (22H, m, —(CH$_2$)$_{11}$—), 2.04 (2H, m, =CH—CH$_2$—), 3.23–3.33 (3H, m, H-5', H-3' and H-2'), 3.44 (1H, dd, J=10.6 and 5.7 Hz, H-6'), 3.51 (1H, dd, J=10.6 and 6.1 Hz, H-6'), 3.59 (1H, dd, J=10.5 Hz and 5.3 Hz, H-1), 3.61 (1H, d, J=2.1 Hz, H-4'), 3.78 (1H, dd, J=10.5 and 7.5 Hz, H-1), 4.13 (1H, d, J=7.5 Hz, H-1'), 4.16–4.20 (1H, m, —CHN$_3$—), 4.91 (1H, br d, J=3.8 Hz, —OH), 4.55 (1H, ap t, —OH), 4.75 (1H, br s, —OH), 4.91 (1H, br d, J=3.6 Hz, —OH), 5.56 (1H, dd, J=15.3 and 7.6 Hz, H-4), 5.65 (1H, dd, J=7.6 Hz and 3.7 Hz, H-3), 5.88 (1H, dt, J=15.3 and 6.8 Hz, H-5), 7.53–8.00 (5H, 3m, —C$_6$H$_5$).

C. (2S,3R,4E)-2-Azido-3-benzoyloxy-1-(4,6-O-benzylidene-β-D-galactopyranosyloxy)-4-octadecene

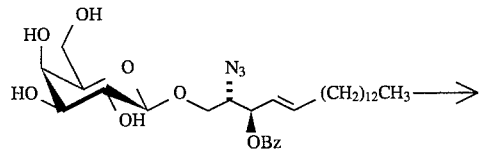

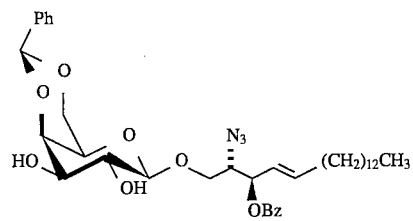

Benzaldehyde (5 mL, large excess) was added to a solution of (2S,3R,4E)- 2-azido-3-benzoyloxy-1-(β-D-galactopyranosyloxy)-4-octadecene (450 mg, 0.76 mmol) in formic acid (5 mL) at 22° C. and under argon. This mixture was stirred for 0.75 hour, then cooled down to 5° C. and diluted with ethyl acetate (25 mL) and water (10 mL). The two-phase solution was neutralized by adding solid sodium bicarbonate and a solution of sodium bicarbonate 1M. The aqueous phase was then extracted with ethyl acetate (2×25 mL). The combined organic layers were washed with a cold solution of sodium bicarbonate (1M, 25 mL), water (25 mL) and brine (25 mL), dried over anhydrous magnesium sulfate, filtered and concentrated.

The residue was purified by silica gel chromatography (20 g, 0% to 90% ethyl acetate/hexane, pure ethyl acetate and 10% acetone/ethyl acetate) and afforded the title compound (233 mg, 45%) as a pale yellow oil.

IR (CH$_2$Cl$_2$) $\upsilon_{max}$ (cm$^{-1}$): 3580 (O—H), 3060, 2930, 2860 (C—H), 2110 (—N$_3$), 1720 (C=O), 1265 (C—O).

$^1$H NMR 400 MHz (CDCl$_3$) δ (ppm): 0.89 (3H, t, J=6.9 Hz, —CH$_3$), 1.25 (20H, br s, —(CH$_2$)$_{10}$—), 1.39 (2H, qi, J=6.9 Hz, —CH$_2$—CH$_3$), 2.09 (2H, m, =CH—CH$_2$—), 3.49 (1H, d, J=0.9 Hz, H-5'), 3.69–3.74 (2H, m, —CHN$_3$— and H-1), 3.80 (1H, dd, J=9.6 Hz and 7.6 Hz, H-1), 3.99–4.05 (2H, m, H-2' and H-3'), 4.08 (1H, dd, J=12.5 and 1.8 Hz, H-6'), 4.23 (1H, dd, J=3.5 and 0.9 Hz, H- 4'), 4.33 (1H, dd overlapping H-1', J=12.5 and 1.3 Hz, H-6'), 4.35 (1H, d, J=7.5 Hz, H-1'), 5.56 (1H, s, —O—CH—O—), 5.61 (1H, ddt, J=15.2, 8.0 and 1.2 Hz, H-4), 5.69 (1H, dd, J=8.0 and 4.0 Hz, H-3), 5.97 (1H, dt, J=15.2 and 6.8 Hz, H-5), 7.34–8.12 (10H, 4m, 2×—C$_6$H$_5$).

D. (2S,3R,4E)-2-Azido-3-benzoyloxy-1-(2,3-di-O-benzoyl-4,6 -O-benzylidene-β-D-galactopyranosyloxy)-4-octadecene

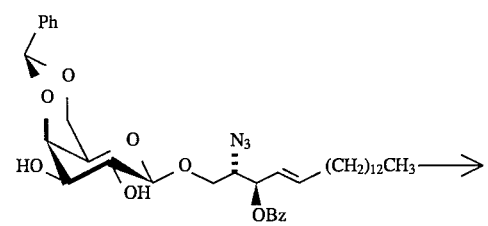

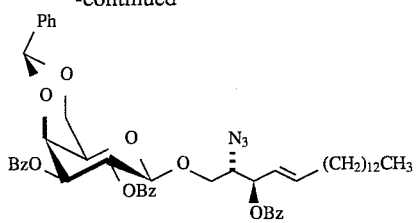

A solution of (2S,3R,4E)-2-azido-3-benzoyloxy-1-(4,6-O-benzylidene-β-D-galactopyranosyloxy)-4-octadecene (223 mg, 0.32 mmol) in pyridine (5 mL) was cooled down to 5° C. under argon. Benzoyl chloride (0.11 mL, 0.96 mmol) was added dropwise to this solution followed by 4-dimethylaminopyridine (≈5 mg) and this mixture was stirred at 5° C. for 18 hours. The mixture was treated with methanol (5 mL) at 5° C. and stirred for 0.5 hour. This reaction mixture was diluted with ethyl acetate (300 mL), washed with a 1M cold aqueous solution of sodium bicarbonate, water and brine. The organic layer was dried over anhydrous magnesium sulfate, filtered and concentrated. The residue was purified by silica gel chromatography (80g, 0% to 2% ethyl acetate/ toluene) and afforded the title compound (254 mg, 89%) as a pale yellow oil.

IR (CH$_2$Cl$_2$) $\upsilon_{max}$ (cm$^{-1}$): 3050, 2930, 2860 (C—H), 2110 (—N$_3$), 1730 (C=O), 1265 (C—O).

$^1$H NMR 400 MHz (CDCl$_3$) δ (ppm): 0.89 (3H, t, J=6.8 Hz, —CH$_3$), 1.23–1.33 (22H, m, —(CH$_2$)$_{11}$—), 1.93 (2H, m, =CH—CH$_2$—), 3.69–3.74 (2H, m, H-1 and —CHN$_3$—), 3.97–4.02 (2H, m, H-1 and H-5'), 4.15 (1H, dd, J=12.4 and 1.5 Hz, H-6'), 4.42 (1H, dd, J=12.4 and 1.3 Hz, H-6'), 4.61 (1H, d, J=3.4 Hz, H-4'), 4.83 (1H, d, J=8.0 Hz, H-1'), 5.40 (1H, dd, J=10.4 and 3.4 Hz, H-3'), 5.46–5.56 (2H, m overlapping —O—CH—O—, H-4 and H-3), 5.56 (1H, s, —O—CH—O—), 5.73 (1H, dt, J=15.2 and 6.7 Hz, H-5), 5.91 (1H, dd, J=10.4 and 8.0 Hz, H- 2'), 7.27–8.04 (20 H, 2m, 4×—C$_6$H$_5$).

E. (2S,3R,4E)-3-Benzoyloxy-2-hexadecanoylamino-1-(2,3-di-O-benzoyl-4,6-O-benzylidene-β-D-galactopyranosyloxy)-4-octadecene

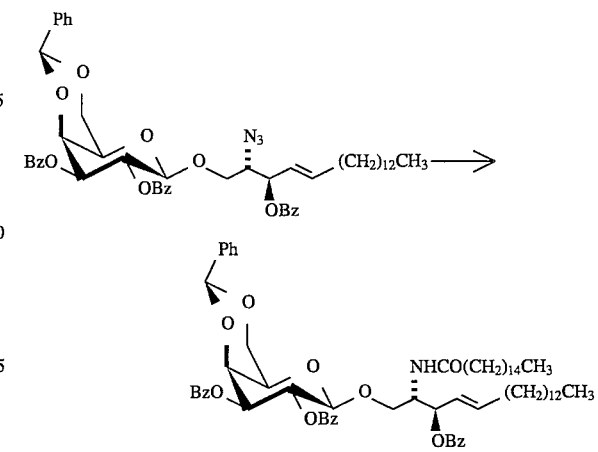

Hydrogen sulfide was bubbled in a solution of (2S,3R,4E)-2-azido-3-benzoyloxy-1-(2,3-di-O-benzoyl-4,6-O-benzylidene-β-D-galactopyranosyloxy)- 4-octadecene (250 mg, 0.28 mmol) in pyridine (10 mL) and water (3 mL) at 22° C. for 15 minutes. The mixture was then tightly closed and stirred for 6 hours. Hydrogen sulfide was again bubbled in for 15 minutes and the mixture was stirred at 22° C. overnight. The next day, the same procedure is repeated with a stirring of 7 hours. The solvents were then evaporated and the residue was dissolved in toluene. This solution was evaporated and the residue was dissolved in tetrahydrofuran (15 mL). To this stirred solution was added an aqueous solution of sodium acetate (50%, 1.5 mL) followed by the dropwise addition of a solution of hexadecanoyl chloride (0.086 mL, 0.28 mmol) in tetrahydrofuran (0.5 mL) at room temperature. The mixture was stirred at 22° C. for 2.5 hours, then diluted with ethyl acetate (45 mL) and washed with a cold aqueous solution of sodium bicarbonate (1 M, 2×15 mL), water (2×15 mL) and brine (2×15 mL). The organic layer was dried over anhydrous magnesium sulfate, filtered and concentrated. The residue was purified by silica gel chromotagraphy (20g, 0% to 35% ethyl acetate/hexane) and afforded the title compound (266 mg, 86%) as a white solid.

IR (CH$_2$Cl$_2$) $\upsilon_{max}$ (cm$^{-1}$): 3060, 2930, 2860 (C-H), 1725 (C=O esters), 1675 (C=O amide), 1265 (C—O).

$^1$H NMR 400 MHz (CDCl$_3$) δ (ppm): 0.89 (6H, t, J=6.8 Hz, 2×—CH$_3$), 1.14–1.43 (48H, m, —(CH$_2$)$_{11}$— and —(CH$_2$)$_{13}$—), 1.83 (2H, t, J=7.6 Hz, —NHCOC$\underline{H}_2$—), 1.99 (2H, m, =CH—C$\underline{H}_2$—), 3.67 (1H, br s, H-5'), 3.81 (1H, dd, J=10.4 and 4.1 Hz, H-1), 4.11 (1H, d, J=12.4 and 1.4 Hz, H-6'), 4.17 (1H, dd, J=10.4 and 4.0 Hz, H-1), 4.30 (1H, dd, J=12.4 and 1.1 Hz, H-6'), 4.42–4.47 (1H, m, H-2), 4.58 (1H, d, J=3.5 Hz, H-4'), 4.74 (1H, d, J=8.0 Hz, H-1'), 5.38 (1H, dd, J=10.4 and 3.5 Hz, H-3'), 5.50 (1H, dd, J=15.3 and 7.0 Hz, H-4), 5.55 (1H, s, —O—CH—O—), 5.60 (1H, dd, J=7.0 Hz, H-3), 5.77–5.87 (1H, m, overlapping H-2', H-5), 5.85 (1H, dd, J=10.4 and 8.0 Hz, H-2'), 7.35–7.99 (20 H, 4m, 4×—C$_6$H$_5$), 8.04 (1H, d, J=8.5 Hz, —NH—).

F. (2S,3R,4E)-3-Benzoyloxy-2-hexadecanoylamino-1-(2, 3-di-O-benzoyl- 6-D-galactopyranosyloxy)-4-octadecene

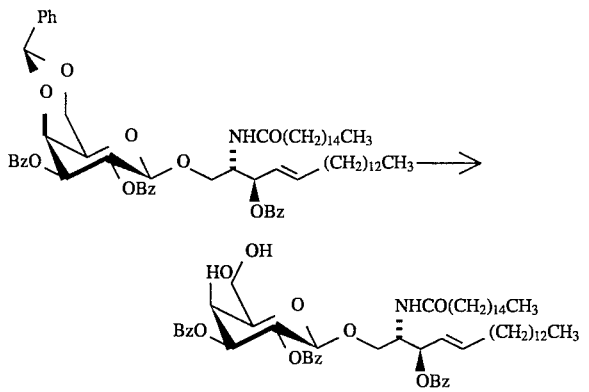

Trifluoroacetic acid (90%, 0.5 mL) was added to a stirred solution of (2S,3R,4E)-3-benzoyloxy-2-hexadecanoylamino-1-(2,3-di-O-benzoyl- 4,6-O-benzylidene-β-D-galactopyranosyloxy)-4-octadecene (258 mg, 0.23 mmol) in dichloromethane (15 mL) at 5° C. The mixture was stirred for 0.5 hour at 5° C. and at 22° C. for 1 hour. Trifluoroacetic acid (same quantity) was added again and the reaction mixture was stirred for one more hour at 22° C. The mixture was diluted with ethyl acetate (30 mL) and washed with a cold aqueous solution of sodium bicarbonate (1M, 2×15 mL), water (2×15 mL) and brine (15 mL). The organic layer was dried over anhydrous magnesium sulfate, filtered and concentrated. The residue was purified by silica gel chromatography (15 g, 0% to 60% ethyl acetate/hexane) and afforded the title compound (193 mg, 83%) as a white solid.

IR (CH$_2$Cl$_2$) $\upsilon_{max}$ (cm$^{-1}$): 3060, 2930, 2860 (C-H), 1730 (C=O esters), 1670 (C=O amide), 1265 (C13 O).

$^1$H NMR 400 MHz (CDCl$_3$) δ (ppm): 0.89 (6H, t, J=6.8 Hz, 2×—CH$_3$), 1.25–1.57 (48H, m, —(CH$_2$)$_{11}$— and —(CH$_2$)$_{13}$—),1.97–2.04 (4H, m, —NHCOC$\underline{H}_2$— and =CH—C$\underline{H}_2$—), 3.53 (1H, t overlapping —OH—6', J=3.0 Hz, H-5'), 3.53–3.58 (1H, m, —OH-6'), 3.67–3.71 (2H, m, H-1 and H-6'), 3.86 (1H, dd, J=12.6 and 3.5 Hz, H-6'), 4.01 (1H, dd, J=9.7 and 1.8 Hz, H-1), 4.25 (1H, br s, H-4'), 4.49–4.54 (1H, m, H-2), 4.66 (1H, d, J=7.8 Hz, H-1'), 5.27 (1H, dd, J=10.4 and 2.9 Hz, H-3'), 5.51 (1H, dd, J=15.4 and 8.2 Hz, H-4), 5.73–5.86 (2H, m, H-3 and H-2'), 5.96 (1H, dt, J=15.3 and 7.0 Hz, H-5), 7.36–8.07 (15H, 5m, 3×—C$_6$H$_5$), 8.06 (1H, d, J=8.4 Hz, —NH—).

G. (2S,3R,4E)-3-Benzoyloxy-2-hexadecanoylamino-1-[2,3 -di-O-benzoyl-4,6-di-O-(sodium oxysulfonyl)-β-D-galactopyranosyloxy]-4-octadecene

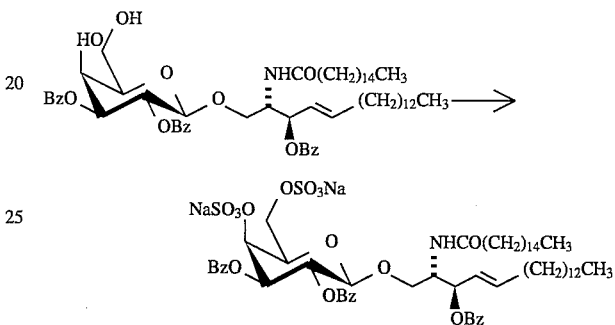

Sulfur trioxide trimethylamine complex (250 mg, 1.8 mmol) was added to a stirred solution of (2S,3R,4E)-3-benzoyloxy-2-hexadecanoylamino-1-(2,3-di-O-benzoyl-β-D-galactopyranosyloxy)-4-octadecene (182 mg, 0.18 mmol) in dry dimethylformamide (12 mL) at 22° C. and under argon. This mixture was heated up to 80°–85° C. for one hour, then sulfur trioxide trimethylamine complex (125 mg, 0.9 mmol) was added again. The reaction was pursued for one more hour. The reaction mixture was then cooled down to 5° C. and treated with an aqueous solution of sodium bicarbonate (1M, until the pH raises 8–9) and this solution was stirred for 0.75 hour. The solvents were evaporated under vacuum and the residue was dissolved in dichloromethane/methanol (8:2). Sodium bicarbonate was filtered on Celite and the filtrate was evaporated. The residue was purified by silica gel column chromatography (25 g, 0% to 30% methanol/chloroform) and further on silica gel plate (chloroform/methanol, 8:2) and afforded the title compound (117 mg, 54%) as a white solid.

IR (nujol) $\upsilon_{max}$ (cm$^{-1}$): 3700–3200 (O-H), 2930, 2860 (C-H), 1725 (C=O esters), 1650 (C=O amide), 1460 (S=O).

$^1$H NMR 400 MHz (DMSO-d$_6$) δ (ppm): 0.83 (6H, 2t, J=6.9 Hz, 2×—CH$_3$), 1.14–1.50 (48H, m, —(CH$_2$)$_{11}$— and —(CH$_2$)$_{13}$—), 1.75–2.00 (4H, m, —NHCOC$\underline{H}_2$— and =CH—C$\underline{H}_2$—), 3.57–3.61 (1H, m, H-5'), 3.82–3.88 and 4.08–4.12 (2×2H, 2m, H-6' and H-1), 4.07–4.13 (1H, m, H-2), 4.66 (1H, d, J=3.3 Hz. H-4'), 4.80 (1H, d, J=7.7 Hz, H-1'), 5.27–5.54 (5H, m, H-3, H-3', H-2', H-5 and H-4), 7.35–7.88 (15H, 3m, 3×—C$_6$H$_5$), 7.76 (1H, d, J=8.9 Hz, —NH—).

EXAMPLE 2

(2S,3R,4E)-3-Hydroxy-2-hexadecanoylamino-1-[4,6-di-O-(sodium oxysulfonyl)-β-D-galactopyranosyloxy]-4-octadecene.

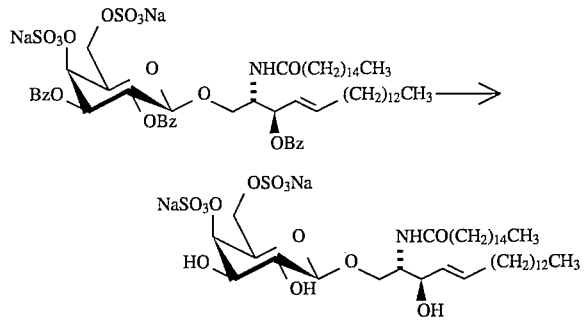

A freshly prepared solution of sodium methoxide in methanol (0.2 M, 60 mL) was added to a stirred solution of (2S,3R,4E)-3-benzoyloxy- 2-hexadecanoylamino-1-[2,3-di-O-benzoyl-4,6-di-O-(sodium oxysulfonyl)-β-D-galactopyranosyloxy]-4-octadecene (1.0 g, 0.82 mmol)in dichloromethane/methanol (1:1, 50 mL) at room temperature. The reaction mixture was stirred for 1 hour then the same quantity of sodium methoxide was added again and this mixture was stirred for one more hour. After neutralization with Dowex 50W8 (H+) resin, water was added (5 mL) and the mixture was filtered. The resin was washed with a mixture of dichloromethane/methanol/water (5:5:1, 55 mL). This solution was treated with Rexyn 102 (Na+) resin, then filtered and the solvents were evaporated under vacuum. The same procedure previously described was applied two more times on the residue obtained. Finally, the residue was purified by silica gel chromatography (30 g, 20% to 30% methanol/chloroform and then methanol/water/chloroform 35:5:60 to 40:10:50) and afforded the title compound (212 mg, 20%), as an off-white solid.

IR (nujol) $\upsilon_{max}$ (cm$^{-1}$): 3700–3100 (O-H and N-H), 2930, 2860 (C-H), 1640 (C=O amide).

$^1$H NMR 400 MHz (DMSO-d$_6$) δ (ppm): 0.84 (6H, t, J=6.7 Hz, 2×—CH$_3$), 1.05–1.26 (46H, br s, —(CH$_2$)$_{10}$— and —(CH$_2$)$_{13}$—), 1.43 (2H, m, —CH$_2$—), 1.91 (2H, m, =CH—CH$_2$—), 2.02 (2H, t, J=7.4 Hz, —CH$_2$CONH—), 3.21 (1H, dd, J=9.6 and 7.7 Hz, H-2'), 3.36–3.41 (2H, m, H-3' and H-5'), 3.67–3.78 (3H, m, H-6', H-1 and H-2), 3.83–3.95 (2H, m, H-1 and H-3), 4.00 (1H, dd, J=9.8 and 4.9 Hz, H-6'), 4.05 (1H, d, J=7.7 Hz, H-1'), 4.33 (1H, d, J=3.0 Hz, H-4'), 5.30 (1H, dd, J=15.3 and 7.2 Hz, H-4), 5.51 (1H, dt, J=15.3 and 6.6 Hz, H-5), 7.54 (1H, d, J=9.1Hz, —NH—).

EXAMPLE 3

(2S,3R,4E)-2-Hexadecanoylamino-3-benzoyloxy-1-(2,3-di-O-benzoyl-4,6 -di-O-(sodium oxysulfonyl)-β-D-glucopyranosyloxy)-4-octadecene A. (2S,3R,4E)-2-Azido-3-benzoyloxy-1-(2,3,4,6-tetra-O-acetyl-α-D-glucopyranosyloxy)-4-octade-cene and (2S,3R, 4E)-2-azido- 3-benzoyloxy-1-(2,3,4,6-tetra-O-acetyl-β-D-glucopyranosyloxy)-4-octadecene

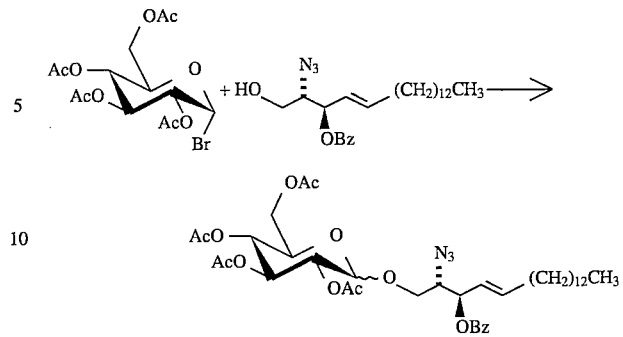

(2S,3R,4E)-2-Azido-3-benzoyloxy-4-octadecen-1-ol (4.3 g, 10.0 mmol) and 2,3,4,6-tetra-O-acetyl-α-D-glucosyl bromide [as described by C. E. Redemann and C. Niemann. *Org. Synth. Coll.* vol. III, p. 11 (1955)] (6.2 g, 15 mmol) were reacted by the general procedure as described in Example 1-A and afforded the β-anomer (2.82 g, 37%) as a white gummy solid and the α-anomer (520 mg, 7%) as a yellow oil.

IR (CH$_2$Cl$_2$) $\upsilon_{max}$ (cm$^{-1}$) α-anomer: 3060, 2930 (C-H), 2100 (N$_3$), 1750 (C=O), 225 (C13 O).

IR (CH$_2$Cl$_2$) $\upsilon_{max}$ (cm$^{-1}$) β-anomer: 3060, 2930 (C-H), 2110 (N$_3$), 1760 (C=O), 1220 (C13 O).

$^1$H NMR 400 MHz (CDCl$_3$) δ (ppm) α-anomer: 0.89 (3H, t, J=6.9 Hz, —CH$_3$), 1.25 (20H, br s, —(CH$_2$)$_{10}$—), 1.40 (2H, m, —CH$_2$—), 2.03, 2.05, 2.07, 2.09 (4×3H, 4s overlapping =CH—CH$_2$—, 4×—OCOCH$_3$—), 2.03–2.14 (2H, m, =CH—CH$_2$—), 3.52 (1H, dd, J=10.8 and 8.0 Hz, H-1), 3.87 (1H, dd, J=10.8 and 3.6 Hz, H-1), 3.96 (1H, dt, J=8.0 and 3.6 Hz, H-2), 4.04 (1H, ddd, J=10.2, 4.5 and 2.3 Hz, H-5'), 4.11 (1H, dd, J=12.4 and 2.3 Hz, H-6'), 4.27 (1H, dd, J=12.4 and 4.5 Hz, H-6'), 4.91 (1H, dd, J=10.2 and 3.7 Hz, H-2'), 5.08 (1H, t, J=10.2 Hz, H-4' or H-3'), 5.12 (1H, d, J=3.7 Hz, H-1'), 5.51 (1H, t, J=10.2 Hz H-3' or H-4'), 5.54–5.61 (2H, m, H-3 and H-4), 5.92–6.00 (1H, m, H-5), 7.46–8.06 (5H, 3m, —C$_6$H$_5$).

$^1$H NMR 400 MHz (CDCl$_3$) δ (ppm) β-anomer: 0.89 (3H, t, J=6.9 Hz, —CH$_3$), 1.26–1.41 (22H, m, —(CH$_2$)$_{11}$—), 2.02, 2.04, 2.06, 2.10 (4×3H, 4s overlapping =CH—CH$_2$—, 4×—OCOCH$_3$), 2.02–2.16 (2H, m, =CH—CH$_2$), 3.61 (1H, dd, J=9.5 and 4.9 Hz, H-1), 3.70 (1H, ddd, J=9.5, 2.4 and 4.7 Hz, H-5'), 3.89–3.97(2H, m, H-1 and H-2), 4.13 (1H, dd, J=12.3 and 2.4 Hz, H-6'), 4.23 (1H, dd, J=12.3 anc 4.7 Hz, H-6'), 4.56 (1H, d, J=8.0 Hz, H-1'), 5.04 (1H, dd, J=9.5 and 8.0 Hz, H-2'), 5.11 (1H, t, J=9.5 Hz, H-4' or H-3'), 5.22 (1H, t, J=9.5 Hz, H-3' or H-4' ), 5.54–5.62 (2H, m, H-3 and H-4), 5.94 (1H, dt, J=14.3 and 6.8 Hz, H-5), 7.45–8.07 (5H, 3m, —C$_6$H$_5$).

B. (2S,3R,4E)-2-Azido-3-benzoyloxy-1-(β-D-glucopyranosyloxy)-4-octadecene

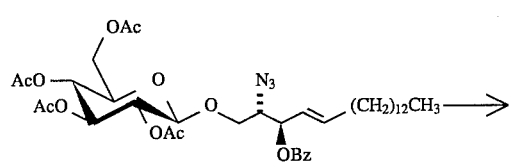

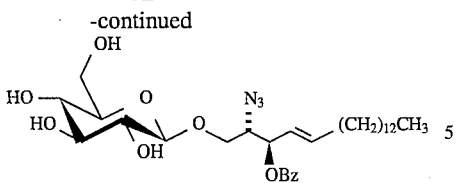

A solution of 2-azido-3-benzoyloxy-1-(2,3,4,6-tetra-O-acetyl-β-D-glucopyranosyloxy)-4-octadecene (2.6 g, 3.42 mmol) in dichloromethane (30 mL) was added slowly to a freshly prepared solution of sodium (1.56 g, 68 mmol) in methanol (60 mL) at −70° C. and under argon. The temperature of the cooling bath was allowed to reach −50° C. over a period of 3 hours. The reaction mixture was cooled down to −70° C. and neutralized with a solution of acetic acid (3.9 mL, 68 mmol) in dichloromethane (10 mL). The mixture was concentrated under vacuum, giving a residue which was dissolved in dichloromethane (50 mL). The residual solid (sodium acetate) was filtered on Celite and washed with dichloromethane (5×10 mL). The combined filtrate and washings were evaporated and the residue was purified by silica gel chromatography (125 g, 0% to 12% methanol/dichloromethane) and afforded the title compound (1.65 g, 82%) as an oil.

IR (CH$_2$Cl$_2$) $\upsilon_{max}$ (cm$^{-1}$): 3600–3200 (O-H), 3060, 2930, 2860 (C-H), 2110 (—N$_3$), 1730 (C=O).

$^1$H NMR 400 MHz (DMSO-d$_6$) δ (ppm): 0.85 (3H, t, J=6.8 Hz, —CH$_3$), 1.20–1.33 (22H, m, —(CH$_2$)$_{11}$—), 2.03 (2H, m, =CH—C$\underline{H}_2$—), 2.95–3.16 (4H, m, H-2', H-3', H-4' and H-5'), 3.40–3.44 (1H, m, H-6'), 3.60 (1H, dd, J=10.5 and 5.2 Hz, H-1), 3.65 (1H, br dd, J=11.5 and 3.3 Hz, H-6'), 3.81 (1H, dd, J=10.5 and 7.8 Hz, H-1), 4.18 (1H, d overlapping H-2, J=7.8 Hz, H-1'), 4.17–4.22 (1H, m, H-2), 4.34 (1H, br t, —OH-6'), 4.90–4.93 (2H, m, 2×—OH), 5.04 (1H, d, J=4.4 Hz, —OH), 5.57 (1H, dd, J=15.2 and 7.6 Hz, H-4), 5.65 (1H, dd, J=7.6 and 3.7 Hz, H-3), 5.88 (1H, dt, J=15.2 and 6.8 Hz, H-5), 7.53–8.00 (5H, 3m, —C$_6$H$_5$).

C. (2S,3R,4E)-2-Azido-3-benzoyloxy-1-(4,6-O-benzylidene-β-D-glucopyranosyloxy)-4-octadecene

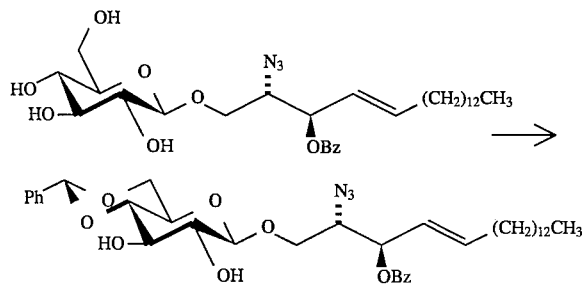

Benzaldehyde dimethyl acetal (0.19 mL, 1.26 mmol) followed by paratoluenesulfonic acid (≈10 mg) were added to a stirred solution of (2S,3R,4E)-2-azido-3-benzoyloxy-1-(β-D-glucopyranosyloxy)-4-octadecene (500 mg, 0.84 mmol) in tetrahydrofuran (10 mL) at 22° C. and under argon. The mixture was stirred for 16 hours then benzaldehyde dimethyl acetal and para-toluenesulfonic acid (same quantities) were added again and the mixture was stirred for 3 more hours. The reaction mixture was cooled down to 5° C., neutralized with pyridine and diluted with ethyl acetate (50 mL). The organic layer was washed with a 1M aqueous solution of sodium bicarbonate (2×50 mL), water (2×50 mL) and brine (50 mL), dried over anhydrous magnesium sulfate, filtered and concentrated. The residue was purified on silica gel plates (60% ethyl acetate/hexane) and afforded the title compound (493 mg, 86%) as an oil.

IR (CH$_2$Cl$_2$) $\upsilon_{max}$ (cm$^{-1}$): 3600 (O-H), 3060, 2930, 2860 (C-H), 2110 (—N$_3$), 1720 (C=O).

$^1$H NMR 400 MHz (CDCl$_3$) δ (ppm): 0.89 (3H, t, J=6.9 Hz, —CH$_3$), 1.26 (20H, br s, —(CH$_2$)$_{10}$—), 1.33–1.42 (2H, m, —CH$_2$—), 2.10 (2H, m, =CH—C$\underline{H}_2$—), 2.78 and 2.98 (2×1H, 2 br s, 2×—OH), 3.45 (1H, td, J=9.7 and 4.9 Hz, H-5'), 3.53–3.59 (2H, m, H-2' and H-3' or H-4'), 3.69–3.73 (2H, m, H-1 and H-6'), 3.83 (1H, t, J=9.1 Hz, H-4' or H-3'), 3.95–4.00 (2H, m, H-1 and H-2), 4.26 (1H, dd, J=10.5 and 4.9 Hz, H-6'), 4.44 (1H, d, J=7.7 Hz, H-1'), 5.53 (1H, s, —O—CH—O—), 5.60 (1H, dd, J=15.2 and 8.1 Hz, H-4), 5.69 (1H, dd, J=8.1 and 4.2 Hz, H-3), 5.99 (1H, dt, J=15.2 and 6.9 Hz, H-5), 7.37–8.08 (10H, 4m, 2×—C$_6$H$_5$).

D. (2S,3R,4E)-2-Azido-3-benzoyloxy-1-(4,6-O-benzylidene-2,3-di-O-benzoyl-β-D-glucopyranosyloxy)-4-octadecene

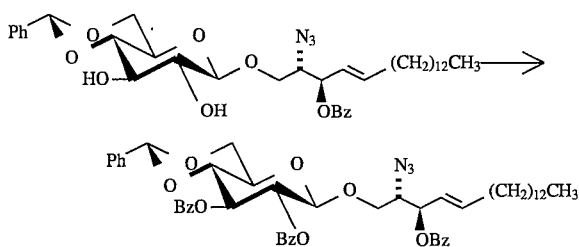

(2S,3R,4E)-2-Azido-3-benzoyloxy-1-(4,6-O-benzylidene-β-D-glucopyranosyloxy)-4-octadecene (300 mg, 0.44 mmol) was reacted by the general procedure as described in Example 1-D and afforded the title compound (400 mg, 100%) as a colorless oil.

IR (CH$_2$Cl$_2$) $\upsilon_{max}$ (cm$^{-1}$): 3060, 2930, 2860 (C-H), 2110 (-N3), 1730 (C=O).

$^1$H NMR 400 MHz (CDCl$_3$) δ (ppm): 0.89 (3H, t, J=6.8 Hz, —CH$_3$), 1.24–1.33 (22H, m, —(CH$_2$)$_{11}$—), 1.96 (2H, m, =CH—C$\underline{H}_2$), 3.66 (1H, dd, J=9.4 and 4.3 Hz, H-1), 3.72 (1H, dd, J=9.4 and 4.8 Hz, H-1), 3.81–4.00 (4H, m, H-2, H-4', H-5' and H-6'), 4.38 (1H, dd, J=10.5 and 4.9 Hz, H-6'), 4.84 (1H, d, J=7.6 Hz, H-1'), 5.46'5.58 (4H, m, H-2', H-3, H-4 and —O—CH—O—), 5.74–5.81 (2H, m, H-5 and H-3'), 7.31–8.05 (20H, 2m, 4×—C$_6$H$_5$).

E. (2S,3R,4E)-2-Hexadecanoylamino-3-benzoyloxy-1-(4,6-O-benzylidene-2,3-di-O-benzoyl-β-D-glucopyranosyloxy)-4-octadecene

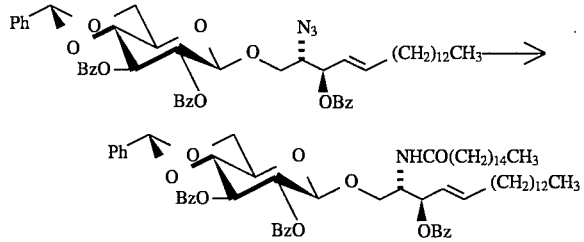

(2S,3R,4E)-2-Azido-3-benzoyloxy-1-(4,6-O-benzylidene-2,3-di-O-benzoyl-β-D-glucopyranosyloxy)-4-octadecene (250 mg, 0.28 mmol) was reacted by the general procedure as described in Example 1-E and afforded the title compound (208 mg, 68%) as a white solid.

IR (CH$_2$Cl$_2$) $\upsilon_{max}$ (cm$^{-1}$): 3060, 2930, 2860 (C-H), 1730 (C=O ester), 1675 (C=O amide).

$^1$H NMR 400 MHz (CDCl$_3$) δ (ppm): 0.89 (6H, t, J=6.8 Hz, 2×—CH$_3$), 1.25–1.48 (48H, m, —(CH$_2$)$_{11}$— and —(CH$_2$)$_{13}$—), 1.84 (2H, t, J=7.6 Hz, —NHCOC$\underline{H}_2$—), 2.01 (2H, m, =CH—C$\underline{H}_2$—), 3.57–3.64 (3H, m, H-1, H-5' and H- 6'), 3.90 (1H, t, J=9.3 Hz, H-4'), 4.04 (1H, dd, J=9.4 and 3.7 Hz, H-1), 4.18 (1H, dd, J=9.5 and 2.3 Hz, H-6'), 4.46 (1H, m, H-2), 4.72 (1H, d, J=7.6 Hz, H- 1'), 5.43 (1H, dd, J=9.3 and 7.6 Hz, H-2'), 5.47–5.53 (3H, m, H-3, H-4 and —O—CH—O—), 5.66 (1H, d, J=9.5 Hz, —NH—), 5.77 (1H, t, J=9.3 Hz, H-3'), 5.88 (1H, dt, J=14.6 and 6.9 Hz, H-5), 7.30–8.07 (20H, 2m, 4×—$C_6H_5$).

F. (2S,3R,4E)-2-Hexadecanoylamino-3-benzoyloxy,1-(2,3 -di-O-benzoyl-β-D-glucopyranosyloxy)-4-octadecene

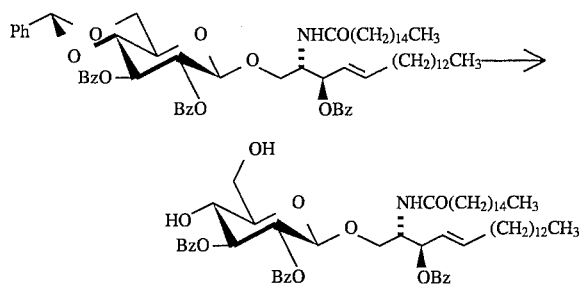

(2S,3R,4E)-2-Hexadecanoylamino-3-benzoyloxy-1-(4,6-O-benzylidene- 2,3-di-O-benzoyl-β-D-glucopyranosyloxy)-4-octadecene (300 mg, 0.27 mmol) was reacted by the general procedure as described in Example 1-F and afforded the title compound (228 mg, 83%) as a white solid.

IR ($CH_2Cl_2$) $\upsilon_{max}$ (cm$^{-1}$): 3060, 2930, 2860 (C-H), 1730 (C=O ester), 1650 (C=O amide).

$^1$H NMR 400 MHz ($CDCl_3$) δ (ppm): 0.89 (6H, t, J=6.8 Hz, 2×—$CH_3$), 1.22–1.48 (48H, m, —$(CH_2)_{11}$— and —$(CH_2)_{13}$—), 1.65 (1H, br s, —OH), 1.65–2.05 (4H, m, —NHCO$CH_2$— and =CH—$CH_2$—), 2.84 (1H, br s, —OH), 3.40 (1H, dt, J=9.6 Hz, H-5'), 3.59 (1H, dd, J=12.5 and 2.5 Hz, H-6'), 3.63 (1H, dd, J=9.5 and 3.7 Hz, H-1), 3.75 (1H, dd, J=12.5 and 3.5 Hz, H-6'), 4.01 (1H, dd, J=9.5 and 1.6 Hz, H-1), 4.09 (1H, t, J=9.6 Hz, H-4'), 4.48 (1H, m, H-2), 4.66 (1H, d, J=7.4 Hz, H-1'), 5.40 (1H, dd, J=9.6 and 7.4 Hz, H-2'), 5.47 (1H, dd, H-3'), 5.50 (1H, dd, J=15.3 and 8.3 Hz, H-4), 5.67 (1H, t, J=8.3 Hz, H-3), 5.77 (1H, d, J=9.6 Hz, —NH—), 5.93 (1H, dt, J=15.3 and 6.8 Hz, H-5), 7.38–8.09 (15H, 4m, 3×—$C_6H_5$).

G. (2S,3R,4E)-2-Hexadecanoylamino-3-benzoyloxy-1-(2,3 -di-O-benzoyl-4,6-di-O-(sodium oxysulfonyl)-β-D-glucopyranosyloxy)-4-octadecene

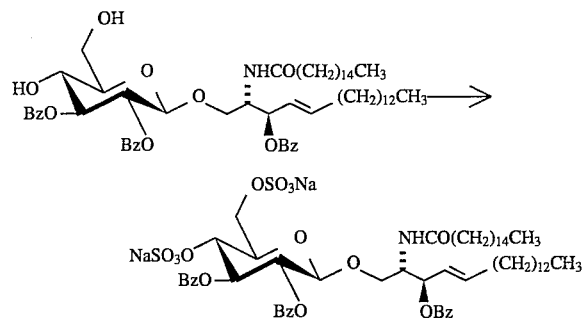

(2S,3R,4E)-2-Hexadecanoylamino-3-benzoyloxy-1-(2,3-di-O-benzoyl-β-D-glucopyranosyloxy)-4-octadecene (226 mg, 0.22 mmol) was reacted by the general procedure as described in Example 1-G and afforded the title compound (261 mg, 97%) as an off-white solid.

IR (nujol) $\upsilon_{max}$ (cm$^{-1}$): 3700–3150 (N-H), 2930, 2860 (C-H), 1730 (C=O ester), 1655 (C=O amide).

$^1$H NMR 400 MHz (DMSO-$d_6$) δ (ppm): 0.84 (6H, t, J=6.7 Hz, 2×—$CH_3$), 1.13–1.38 (48H, m, —$(CH_2)_{11}$— and —$(CH_2)_{13}$—), 1.79 (2H, m, =CH—$CH_2$—), 1.88–2.04 (2H, m, —NHCO$CH_2$—), 3.16–3.31 (1H, m, H-5'), 3.59 (1H, dd, J=9.6 and 7.1 Hz, H-5'), 3.68 (1H, dd, J=11.1 and 9.5 Hz, H-1), 3.81'3.85 (2H, m, H-1 and H-6'), 4.15 (1H, t, J=9.6 Hz, H-4'), 4.23–4.38 (1H, m, H-2), 4.38 (1H, d, J=10.2 Hz, H-6'), 4.89 (1H, d, J=7.9 Hz, H-1'), 5.07 (1H, dd, J=9.5 and 7.9 Hz, H-2'), 5.28 (1H, dd, J=7.1 and 4.1 Hz, H-3), 5.38–5.51 (2H, m, H-4 and H-5), 5.55 (1H, t, J=9.5 Hz, H-3'), 7.35–7.88 (15H, 2m, 3×—$C_6H_5$).

EXAMPLE 4

(2S,3R,4E)-2-Hexadecanoylamino-3-hydroxy-1-(4,6-di-O-(sodium oxysulfonyl)-β-D-glucopyranosyloxy)-4-octadecene

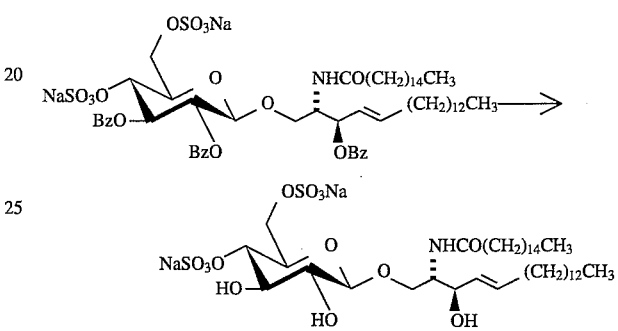

(2S,3R,4E)-2-Hexadecanoylamino-3-benzoyloxy-1-(2,3-di-O-benzoyl-4,6 -di-O-(sodium oxysulfonyl)-β-D-glucopyranosyloxy)-4-octadecene (160 mg, 0.13 mmol) was reacted by the general procedure as described in Example 2-A and afforded the title compound (31 mg, 26%).

IR (nujol) $\upsilon_{max}$ (cm$^{-1}$): 3650–3100 (N-H), 2920, 2855 (C-H), 1645 (C=O amide).

$^1$H NMR 400 MHz (DMSO-$d_6$) δ (ppm): 0.85 (6H, t, J=6.9 Hz, 2×—$CH_3$), 1.24–1.45 (48H, m, —$(CH_2)_{11}$— and —$(CH_2)_{13}$—), 1.93 (1H, m, =CH—$CH_2$—), 2.03 (2H, t, J=7.4 Hz, —NHCO$CH_2$—), 3.04 (1H, t, J=7.4 Hz, H-2'), 3.41–3.45 (3H, m, H-1, H-3' and H-5'), 3.53 (1H, dd, J=10.9 and 9.1 Hz, H-6'), 3.63 (1H, dd, J=9.6 and 8.9 Hz, H-4'), 3.78–3.85 (2H, m, H-2 and H-3), 3.98 (1H, dd, J=10.1 and 5.3 Hz, H-1), 4.13 (2H, m, H-1' and H-6'), 4.91 (1H, d, J=5.4 Hz, —OH), 5.14 (1H, d, J=4.1 Hz, —OH), 5.34 (1H, dd, J=15.4 and 6.9 Hz, H-4), 5.38 (1H, s, —OH), 5.52 (1H, dt, J=15.4 and 6.7 Hz, H-5), 7.53 (1H, d, J=8.9 Hz, —NH—).

EXAMPLE 5

(2S,3R,4E)-3-Benzoyloxy-1-[2,6-di-O-(sodium oxysulfonyl)-β-D-galactopyranosyloxy]-2-(cis-15-tetracosenoylamino)-4-octadecene A. (2S,3R,4E),3-Benzoyloxy-2-(cis-15-tetracosenoylamino)-1-(2,3,4,6 -tetra-O-acetyl-β-D-galactopyranosyloxy)-4-octadecene

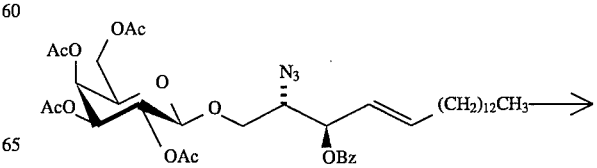

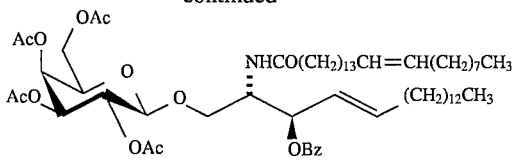

A solution of (2S,3R,4E)-2-azido-3-benzoyloxy-1-(2,3,4,6-tetra-O-acetyl-β-D-galactopyranosyloxy)-4-octadecene prepared as described in Example 3-A (0.35 g, 0.461 mmol) in pyridine (20 mL) and water (4 mL) was saturated with hydrogen sulfide and stirred at 22° C. for 24 hours. The solvents were evaporated under vacuum and the residue dried by co-evaporation with toluene. The residue obtained was dissolved in dichloromethane (40 mL) under argon and treated with nervonic acid (0.338 g, 0.922 mmol) and 1-ethyl- 3-(3-dimethylaminopropyl)-carbodiimide hydrochloride (0.270 g, 1.41 mmol) at room temperature. The resulting mixture was stirred for 18 hours, then diluted with dichloromethane (≈300 mL) and washed with water and brine. The organic phase was dried over anhydrous magnesium sulfate, filtered and concentrated. The residue was purified by silica gel chromatography (75 g, 0% to 30% ethyl acetate/toluene) and afforded the title compound (0.36 g, 72%).

$[\alpha]^{22}_D$: +1.4° (c=1.0, CHCl$_3$).

IR (neat) $\upsilon_{max}$ (cm$^{-1}$: 3500–3150 (O-H and N-H), 2930, 2860 (C-H), 1750 (C=O esters), 1660 (C=O amide), 1250 (C13 O).

$^1$H NMR 400 MHz (CDCl$_3$) δ (ppm): 0.89 (6H, t, J=6.8 Hz, —CH$_3$), 1.24–1.35 (54H, m, —(CH$_2$)$_{10}$—, —(CH$_2$)$_{11}$— and —(CH$_2$)$_6$—), 1.58–1.62 (2H, m, —CH$_2$—), 1.96, 1.99, 2.04 and 2.17 (4×3H, 4s, 4×—OCOCH$_3$), 1.99–2.06 (6H, m overlapping —OCOCH$_3$, 3×=CH—CH$_2$—), 2.1414 2.21 (2H, m overlapping —OCOCH$_3$, —NHCOCH$_2$—), 3.68 (1H, dd, J=10.0 and 4.3 Hz, H-1), 3.85 (1H, br t, H-5'), 3.96 (1H, dd, J=11.2 and 6.2 Hz, H-6'), 4.04 (1H, dd, J=11.2 and 7.2 Hz, H-6'), 4.06 (1H, dd, J=1 0.0 and 4.0 Hz, H-1), 4.45 (1H, d, J=7.8 Hz, H-1'), 4.50 (1H, m, H-2), 5.00 (1H, dd, J=10.5 and 3.4 Hz, H-3'), 5.17 (1H, dd, J=10.5 and 7.8, H-2'), 5.36 (3H, m, H-4' and cis-CH=CH—), 5.49 (1H, dd overlaping H-3, J=14.9 and 7.5 Hz, H-4), 5.54 (1H, m, H-3), 5.76 (1H, d, J=5.8 Hz, —NH—), 5.89 (1H, dt, J=14.9 and 6.8 Hz, H-5), 7.43–8.06 (5H, 3m, —C$_6$H$_5$).

B. (2S,3R,4E)-3-Benzoyloxy-1-(β-D-galactopyranosyloxy)-2-(cis- 15-tetracosenoylamino)-4-octadecene

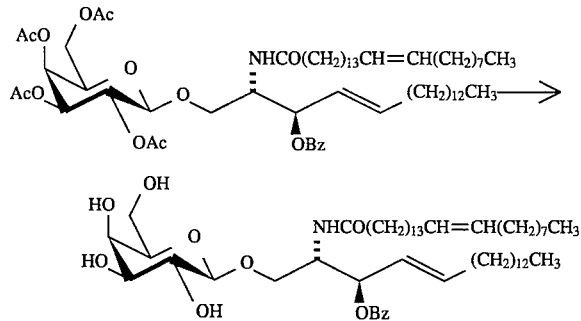

A solution of sodium methoxide in methanol (0.2M, 0.1 mL) was added to a stirred solution of (2S,3R,4E)-3-benzoyloxy-2-(cis-15-tetracosenoyl-amino)- 1-(2,3,4,6-tetra-O-acetyl-β-D-galactopyranosyloxy)-4-octadecene (0.22 g, 0.203 mmol) in methanol (5 mL) at 5° C. and under argon. The solution was stirred for 1.5 hours at 5° C. Dowex 50WX8 (H$^+$) resin was added to this mixture and the stirring was continued until the pH of the solution became neutral. The reaction mixture was filtered and concentrated under vacuum. The residue was purified by silica gel chromatography (50 g, 0% to 20% methanol/chloroform) and afforded the title compound (0.16 g, 84%) as a white glassy solid.

$[\alpha]^{22}_D$:+7.2° (c=1.0, CHCl$_3$).

IR (neat) $\upsilon_{max}$ (cm$^{-1}$): 3700–3100 (O-H and N-H), 2925, 2860 (C-H), 1720 (C=O esters), 1645 (C=O amide).

$^1$H NMR 400 MHz (CDCl$_3$) δ (ppm): 0.89 (6H, m, 2×—CH$_3$), 1.24–1.35 (52H, m, —(CH$_2$)$_{10}$—, —(CH$_2$)$_{11}$— and —(CH$_2$)$_5$—), 1.57–1.63 (4H, m, 2×—CH$_2$—), 2.00–2.07 (6H, m, 3×=CH—CH$_2$—), 2.19 (2H, m, —NHCOCH$_2$—), 2.99 (2H, br s, —OH), 3.43 (1H, dd, J=4.4 and 4.4 Hz, H-5'), 3.50–3.65 (3H, m, H-6' and H- 3'), 3.68 (1H, dd, J=9.4 and 7.6 Hz, H-2'), 3.74 (1H, br s, —OH), 3.81 (1H, dd overlapping —OH, J=10.9 and 4.2 Hz, H-1), 3.85 (1H, br s, —OH), 3.99–4.03 (2H, m, H-1 and H-4'), 4.29 (1H, d, J=7.6 Hz, H-1'), 4.59 (1H, m, H-2), 5.36 (2H, m, cis—CH=CH—), 5.51 (1H, dd, J=15.4 and 7.5 Hz, H-4), 5.66 (1H, br t, H-3), 5.92 (1H, dt, J=15.4 and 6.8 Hz, H-5), 6.12 (1H, d, J=9.5 Hz, —NH—), 7.45–8.05 (5H, 3m, —C$_6$H$_5$).

C. (2S,3R,4E)-3-Benzoyloxy-1-(3,4-O-isopropylidene-β-D-galactopyranosyloxy)-2-(cis-15-tetracosenoylamino)-4-octadecene

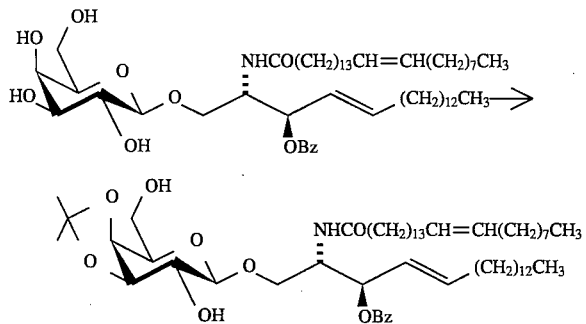

p-Toluenesulfonic acid (55 mg) was added to a solution of (2S,3R,4E)- 3-benzoyloxy-1-(β-D-galactopyranosyloxy)-2-(cis-15-tetracosenoylamino)-4-octadecene (0.88 g, 0.962 mmol) in 2,2-dimethoxypropane (40 mL) at 22° C. and under argon and the resulting mixture was stirred for 17 hours at room temperature. Water (25 mL) was added to the mixture followed by p-toluenesulfonic acid (55 mg) and this was stirred at room temperature for 2 more hours. The reaction mixture was then diluted with ethyl acetate (400 mL) and washed with a saturated solution of sodium bicarbonate and brine. The organic layer was dried over anhydrous magnesium sulfate, filtered and concentrated. The residue was purified by silica gel chromatography (60 g, 50% ethyl acetate/toluene to pure ethyl acetate) and afforded the title compound (0.80 g, 87%).

IR (neat) $\upsilon_{max}$ (cm$^{-1}$): 3700–3110 (O-H and N-H), 2925, 2860 (C-H), 1720 (C=O esters), 1645 (C=O amide).

$^1$H NMR 400 MHz (CDCl$_3$) δ (ppm): 0.89 (6H, t, J=6.8 Hz, 2×—CH$_3$), 1.25–1.34 (54H, m, —(CH$_2$)$_{10}$—, —(CH$_2$)$_{11}$— and —(CH$_2$)$_6$—), 1.34 and 1.51(2×3H, 2s, —C(CH$_3$)$_2$), 1.58–1.63 (2H, m, —CH$_2$—), 2.00—2.07 (6H, m, 3×=CH—CH$_2$—), 2.19 (2H, m, —NHCOCH$_2$—), 2.54 (1H, dd, J=9.2 and 3.3 Hz, —OH), 3.09 (1H, s, —OH), 3.50 (1H, t, J=7.6 Hz, H-5'), 3.75–3.86 (3H, m, H-1, H-2' and H-6'), 3.92–4.00 (1H, m overlapping H-1, H-6'), 3.98 (1H, dd, J=11.1 and 5.5 Hz, H-1), 4.08 (1H, dd, J=7.1 and 5.6 Hz, H-3'), 4.12 (1H, dd, J=5.5 and 2.1 Hz, H-4'), 4.20 (1H, d, J=8.2 Hz, H-1'), 4.55 (1H, m, H-2), 5.35 (2H, m, cis-CH=CH—), 5.51 (1H, dd, J=15.3 and 7.3 Hz, H-4), 5.62 (1H, dd, J=6.7 and 6.7 Hz, H-3), 5.90 (1H, dt, J=15.3 and 6.7

Hz, H-5), 5.98 (1H, d, J=9.2 Hz, —NH—), 7.44–8.05 (5H, 3m, —C₆H₅).

D. (2S,3R,4E)-3-Benzoyloxy-1-[3,4-O-isopropylidene-2,6-di-O-(sodium oxysulfonyl)-β-D-galactopyranosyloxy]-2-(cis-15-tetracosenoylamino)-4-octadecene

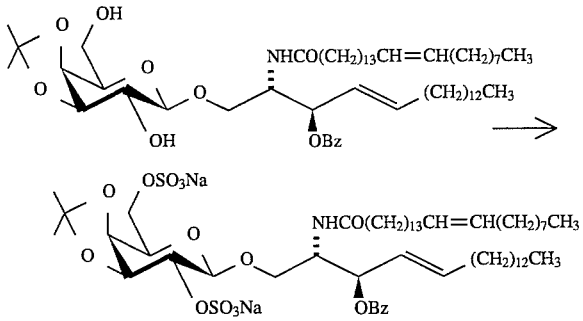

Sulfur trioxide pyridine complex (0.41 g, 2.58 mmol) was added in a solution of (2S,3R,4E)-3-benzoyloxy-1-(3,4-O-isopropylidene-δ-D-galactopyranosyloxy)-2-(cis-15-tetracosenoylamino)-4-octadecene (0.34 g, 0.356 mmol) in pyridine (10 mL) at room temperature and under argon. The reaction mixture was stirred for 5 hours at room temperature, then water (5 mL) was added followed by solid sodium bicarbonate (0.5 g). The solvents were evaporated under vacuum and the resulting residue was triturated with methanol (25 mL) and filtered. The filtrate was concentrated under vacuum and the residue was purified by silica gel chromatography (48 g, 10% to 30% methanol/chloroform) to give the title material (0.35 g, 85%).

IR (KBr) $\upsilon_{max}$ (cm⁻¹): 3700–3200 (N-H), 2915, 2860 (C-H), 1725 (C=O ester), 1635 (C=O amide), 1270 (C13 O and S=O).

¹H NMR 400 MHz (DMSO-d₆) δ (ppm): 0.83 (6H, t, J=6.6 Hz, 2x—CH₃), 1.19–1.49 (59H, m, —(CH₂)₁₁—, —(CH₂)₁₁—, —(CH₂)₆— and —C(CH₃)₂—), 1.35 (3H, s, —C(CH₃)₂—), 1.92—2.17 (8H, 2m, 3x=CH—CH₂— and —NHCOCH₂—), 3.37 (1H, dd, J=10.1 and 4.3 Hz, H-1), 3.72–3.80 (2H, m, H-6'), 3.85 (1H, td, J=6.0 and 1.7 Hz, H-5'), 3.94 (1H, dd, J=10.1 and 3.4 Hz, H-1), 4.09–4.12 and 4.22–4.27 (4H, 2m, H-2, H-2', H-3' and H-4'), 4.47 (1H, d, J=5.5 Hz, H- 1'), 5.30 (2H, m, cis—CH=CH—), 5.36 (1H, dd, J=7.6 and 7.6 Hz, H-3), 5.43 (1H, dd, J=15.1 and 7.6 Hz, H-4), 5.72 (1H, dt, J=15.1 and 6.7 Hz, H-5), 7.47–7.96 (5H, 3m, —C₆H₅), 8.06 (1H, d, J=9.1 Hz, —NH—).

E. (2S,3R,4E)-3-Benzoyloxy-1-[2,6-di-O-(sodium oxysulfonyl)-β-D-galactopyranosyloxy]-2-(cis-15-tetracosenoylamino)-4-octadecene

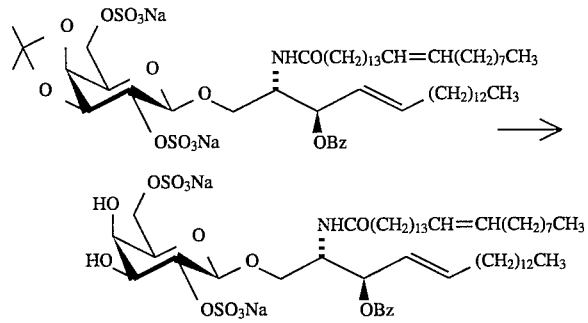

(2S,3R,4E)-3-benzoyloxy-1-[3,4-O-isopropylidene-2,6-di-O-(sodium oxysulfonyl)-β-D-galactopyranosyloxy]-2-(cis-15-tetracosenoylamino )-4-octadecene (0.40 g, 0.345 mmol) was treated with trifluoroacetic acid (90%, 10 mL) and this resulting suspension was stirred for 30 minutes at room temperature. The mixture was concentrated under vacuum and the residue was co-evaporated with toluene (2×25 mL). The residue was then dissolved in a mixture of methanol/chloroform (2:8, 25 mL) and treated with Rexyn 102 (Na⁺) resin. The mixture was stirred for ≈15 minutes. The resin was filtered and washed with a mixture methanol/chloroform (2:8). The filtrate was finally concentrated under vacuum. The residue obtained was purified by silica gel chromatography (30 g, 10% to 30% methanol/chloroform) and afforded the title compound (0.36 g, 92%) as a white amorphous solid.

$[\alpha]^{22}_D$ 0° (c=1.0, CHCl₃).

IR (KBr) $\upsilon_{max}$ (cm⁻¹): 3700–3100 (N-H), 2920, 2860 (C-H), 1725 (C=O ester), 1635 (C=O amide), 1270 (C13 O and S=O).

¹H NMR 400 MHz (DMSO-d₆) δ (ppm): 0.83 (6H, m, 2x—CH₃), 1.19–1.44 (56H, m, —(CH₂)₁₁—, —(CH₂)₁₁— and —(CH₂)₆—), 1.95–2.22 (8H, 2m, 3x=CH—CH₂— and —NHCOCH₂—), 3.44–3.50 (2H, m, H-3' and H-1), 3.57 (1H, br t, H- 5'), 3.62 (1H, dd, J=3.6 and 3.6 Hz, H-4'), 3.74 (1H, dd, J=10.6 and 6.4 Hz, H-6'), 3.82 (1H, dd, J=10.6 and 5.7 Hz, H-6'), 3.95 (1H, dd, J=9.7 and 4.3 Hz, H-1), 4.14 (1H, dd, J=9.4 and 7.7 Hz, H-2'), 4.24–4.29 (1H, m overlapping H-1', H-2), 4.27 (1H, d, J=7.7 Hz, H-1'), 4.69 (1H, d, J=4.2 Hz, —OH), 5.09 (1H, d, J=0.9 Hz, —OH), 5.30 (2H, m, cis—CH=CH—), 5.38 (1H, m overlapping H-4, H-3), 5.44 (1H, dd, J=14.9 and 7.6 Hz, H-4), 5.75 (1H, dt, J=14.9 and 6.6 Hz, H-5), 7.46–7.96 (5H, 3m, —C₆H₅), 7.72 (1H, d, J=9.0 Hz, —NH—).

EXAMPLE 6

(2S,3R,4E)-3-Hydroxy-1-[2,6-di-O-(sodium oxysulfonyl)-β-D-galactopyranosyloxy]-2-(cis-15-tetracosenoylamino)-4-octadecene

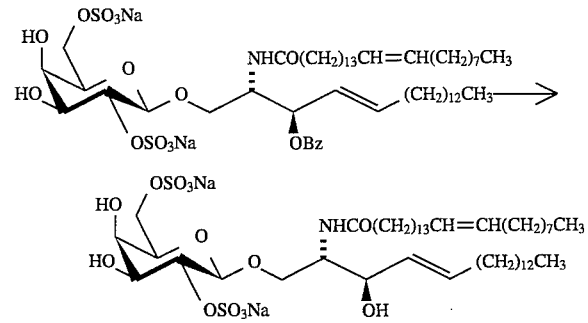

A freshly prepared solution of sodium methoxide in methanol (0.2M, 0.5 mL, 0.1 mmol) was added to a stirred solution of (2S,3R,4E)-3-benzoyloxy-1-[2,6-di-O-(sodium oxysulfonyl)-β-D-galactopyranosyloxy]-2-(cis- 15-tetracosenoylamino)-4-octadecene (0.26 g, 0.232 mmol) in methanol (10 mL) and dichloromethane (5 mL) at 22° C. and under argon. After 3 hours at 22° C., more sodium methoxide (same quantity) was added and the mixture was stirred for another 20 hours. Dowex-50W 8% XL 100–200 mesh resin was then added until the pH of the mixture reached ≈7. The resin was filtered and washed with a mixture chloroform/methanol (7:3). The filtrate was then treated with Rexyn 102 (Na⁺) resin and stirred for ≈15 minutes. The resin was filtered and washed again with a mixture chloroform/methanol (7:3). The filtrate was finally concentrated under vacuum. The residue obtained was purified by silica gel chromatography (28 g, 10% to 40% methanol/chloroform) and afforded the title compound (0.13 g, 30%) as a white amorphous solid.

IR (KBr) $\upsilon_{max}$ (cm$^{-1}$): 3600–3100 (N-H), 2920, 2850 (C-H), 1630 (C=O amide), 1210 (C13 O and S=O).

$^1$H NMR 400 MHz (DMSO-d$_6$) δ (ppm): 0.84 (6H, t, J=6.7 Hz, 2×—CH$_3$), 1.22–1.48 (56H, m, —(CH$_2$)$_{11}$—, —(CH$_2$)$_{11}$— and —(CH$_2$)$_6$—), 1.87–2.18 (8H, 3m, 3×=CH—CH$_2$— and —NHCOCH$_2$—), 3.24–3.29 (1H, m, H-1), 3.47 (1H, ddd, J=9.9, 3.0 and 1.6 Hz, H-3'), 3.57 (1H, ap t, H-5'), 3.62 (1H, dd, J=3.7 and 3.7 Hz, H-4'), 3.69 (1H, m, H-3), 3.75–3.87 (3H, m, H-6' and H-1), 4.09 (1H, dd, J=9.9 and 7.7 Hz, H-2'), 4.14 (1H, dd, 9.1 and 2.5 Hz, H-2), 4.23 (1H, d, J=7.7 Hz, H-1'), 4.68 (1H, d, J=4.1 Hz, —OH), 4.86 (1H, d, J=5.6 Hz, —OH), 4.93 (1H, d, J=1.6 Hz, —OH), 5.26–5.34 (3H, m, cis—CH=CH— and H-4), 5.47 (1H, dt, J=15.3 and 6.5 Hz, H-5), 7.40 (1H, d, J=9.2 Hz, —NH—).

EXAMPLE 7

(2S,3R,4E)-3-Benzoyloxy-1-[3,4-di-O-benzoyl-2,6-di-O-(sodium oxysulfonyl)-β-D-galactopyranosyloxy]-2-(cis-15-tetracosenoylamino)-4-octadecene

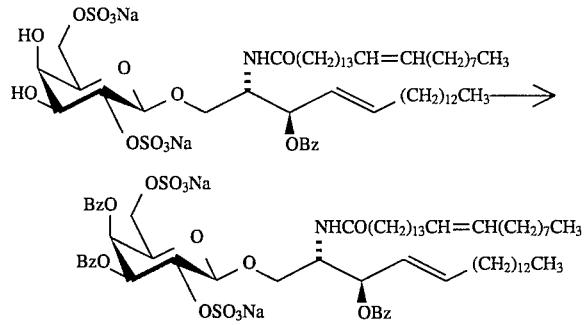

To a stirred solution of (2S,3R,4E)-3-benzoyloxy-1-[2,6-di-O-(sodium oxysulfonyl)-β-D-galactopyranosyloxy]-2-(cis-15-tetracosenoylamino)-4-octadecene (160 mg, 0.14 mmol) in pyridine (1.6 mL) at 0° C. was added benzoyl chloride (45 mL, 0.42 mmol) followed by dimethylaminopyridine (1 crystal). The mixture was stirred for 2 hours at 22° C. and benzoyl chloride was added again (33 mL, 0.28 mmol). The mixture was stirred overnight at 22° C. then methanol (0.4 mL) was added and the stirring was continued for 15 minutes. The mixture was evaporated under vacuum and the resulting residue was co-evaporated with toluene, dissolved in chloroform (≈10 mL) and filtered on microfibre paper. The filtrate was treated with Rexyn 102 (Na$^+$) resin and methanol (4 mL), and the resulting mixture was stirred for 1 hour, filtered on microfibre paper and evaporated under vacuum. The residue was co-evaporated with toluene then purified by silica gel H column chromatography (≈80 g, 25% methanol/chloroform) and then on silica gel plates (25% methanol/chloroform) and afforded the title compound (87 mg, 47%) as a white solid.

[α]$^{22}_D$: +8.3° (c=1.0, CHCl$_3$).

IR (KBr) $\upsilon_{max}$ (cm$^{-1}$): 3700–3150 (N-H), 2925, 2860 (C-H), 1725 (C=O esters), 1645 (C=O areida), 1270 (C13 O and S=O).

$^1$H NMR 400 MHz (DMSO-d$_6$) δ (ppm): 0.82–0.85 (6H, m, 2×—CH$_3$), 1.19–1.70 (56H, m, —(CH$_2$)$_{11}$—, —(CH$_2$)$_{11}$— and —(CH$_2$)$_6$—), 1.95–2.20 (BH, 2m, 3×=CH—CH$_2$— and —NHCOCH$_2$—), 3.37–3.52 (2H, m, H-1 and H-6'), 3.66 (1H, dd, J=10.6 and 6.0 Hz, H-6') 4.18–4.20 (2H, m, H-5' and H-1), 4.31 (1H, m, H-2), 4.49 (1H, dd, J=9.9 and 7.9 Hz, H-2') 4.64 (1H, d, J=7.9 Hz, H-1'), 5.22 (1H, dd, J=9.9 and 3.3 Hz, H-3'), 5.26–4.47 (4H, m, cis—CH=CH—, H-3 and H- 4), 5.57 (1H, d, J=3.3 Hz, H-4'), 5.75 (1H, dt, J=14.3 and 6.9 Hz, H-5), 7.26–8.01 (15H, 4m, 3×—C$_6$H$_5$), 8.16 (1H, d, J=9.2 Hz, —NH—).

EXAMPLE 8

(2S,3R,4E)-3-Benzoyloxy-2-hexadecanoylamino-1-[2-O-benzoyl-4-O-acetyl- 3,6-di-O-(sodium oxysulfonyl)-β-D-galactopyranosyloxy]-4-octadecene A. (2S,3R,4E)-2-Azido-3-hydroxy-1-(3,4-O-isopropylidene-β-D-galactopyranosyloxy)-4-octadecene

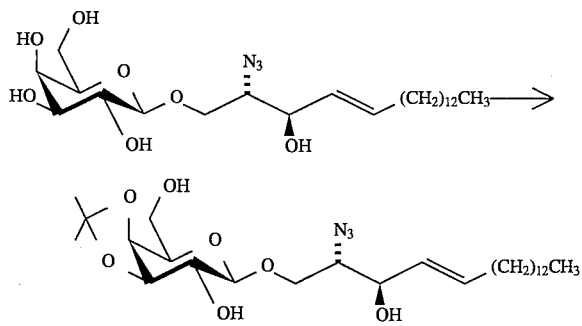

p-Toluenesulfonic acid (90 mg) was added to a solution of (2S,3R,4E)-2 -azido-3-hydroxy-1-(β-D-galactopyranosyloxy)-4-octadecene [as described by P. Zimmermann, R. Bommer, T. Bar and R. R. Schmidt. *J. Carbohydrate Chem.* 7, 435–452 (1988)] (0.50 g, 1.07 mmol) in 2,2-dimethoxypropane (50 mL) at 22° C. and under argon and the resulting mixture was stirred for 2 days at room temperature. Water (10 mL) was added to the mixture and this was stirred at room temperature for 40 minutes. The reaction mixture was then diluted with ethyl acetate and washed with a saturated solution of sodium bicarbonate and brine. The organic layer was dried over anhydrous magnesium sulfate, filtered and concentrated. The residue was purified on silica gel plates (ethyl acetate) and afforded the title compound (0.425 g, 75%).

$^1$H NMR 200 MHz (CDCl$_3$) δ (ppm): 0.88 (3H, t, J=6.8 Hz, —CH$_3$), 1.25 (22H, m, —(CH$_2$)$_{11}$—), 1.35 and 1.53 (2×3H, 2s, (CH$_3$)$_2$—CH—), 1.64–2.13 (5H, m =CH—CH$_2$— and 3×—OH), 3.44 (1H, m, H-2), 3.59 (1H, t, J=7.4 Hz, H-1), 3.81–4.35 (9H, m, H-1', H-2', H-3', H-4', H-5', H-6', H-1 and H-3), 5.53 (1H, m, H- 4), 5.86 (1H, m, H-5).

B. (2S,3R,4E)-2-Azido-3-hydroxy-1-(3,4-O-isopropylidene-6 -O-tert-butyldimethylsilyl-β-D-galactopyranosyloxy)-4-octadecene

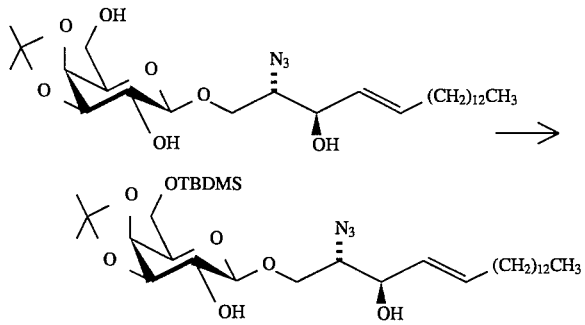

tert-Butyldimethylsilyl chloride (425 mg, 2.82 mmol) was added to a stirred solution of (2S,3R,4E)-2-azido-3-hydroxy-1-(3,4-O-isopropylidene-β-D-galactopyranosyloxy)-

4-octadecene (425 mg, 0.805 mmol) in pyridine (20 mL) at −20° C. and under argon. The reaction mixture was stirred at −20° C. overnight, then methanol was added. The mixture was stirred again for 2 more hours at 22° C. The reaction was then poured into water and diluted with ethyl acetate (150 mL). The organic layer was washed with water (5x) and brine, dried over anhydrous magnesium sulfate, filtered and concentrated. The residue was purified by silica gel chromatography and afforded the title compound (537 mg, 100%).

$^1$H NMR 200 MHz (CDCl$_3$) δ (ppm): 0.08 (6H, s, —Si(CH$_3$)$_2$), 0.88 (3H, t, J=6.7 Hz, —CH$_2$—CH$_3$), 0.90 (9H, s, —C(CH$_3$)$_3$), 1.25 (29H, m, —(CH$_2$)$_{11}$—), 1.34 and 1.53 (2×3H, 2s, (CH$_3$)$_2$—C—), 1.66–2.11 (4H, m, =CH—C$\underline{H}_2$— and 2×—OH), 3.45 (1H, m, H-2), 3.57 (1H, t, H-1), 3.80–4.32 (9H, m, H-1', H-2', H-3', H-4', H-5', H-6', H-1 and H-3), 5.53 (1H, m, H-4), 5.84 (1H, m, H-5).

C. (2S,3R,4E)-2-Azido-3-benzoyloxy-1-(2-O-benzoyl-3,4 -O-isopropylidene-6-O-tert-butyldimethylsily-β-D-galactopyranosyloxy)- 4-octadecene

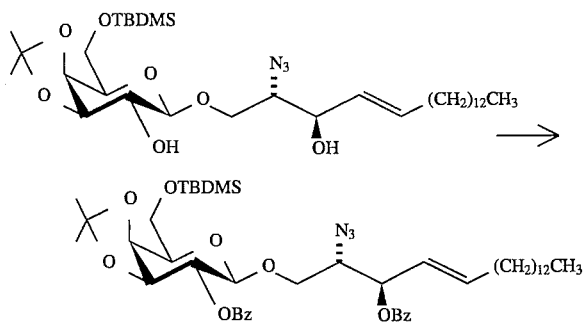

Benzoyl chloride (500 mg, 3.56 mmol) was added to a stirred solution of (2S,3R,4E)-2-azido-3-hydroxy-1-(3,4-O-isopropylidene-6 -O-tert-butlydimethylsilyl-β-D-galactopyranosyloxy)-4-octadecene (537 mg, 0.837 mmol) in pyridine (20 mL) at 0° C. and under argon. The reaction was stirred at 0° C. for 3 hours then benzoyl chloride (300 mg, 2.13 mmol) was added again. The mixture was stirred overnight at 0° C. Methanol (4 mL) was then added to the reaction mixture and this was stirred again for 1 hour at 5° C., then poured into a mixture of cold water and ethyl acetate. The organic layer was washed with water (4x) and brine, dried over anhydrous magnesium sulfate, filtered and concentrated. The residue was purified by silica gel chromatography (5% to 10% ethyl acetate/hexane) and afforded the title compound (572 mg, 80%).

$^1$H NMR 200 MHz (CDCl$_3$) δ(ppm): 0.09 (6H, s, —Si(CH$_3$)$_2$), 0.84–0.94 (3H, m overlapping —C(CH$_3$)$_3$, —CH$_2$—CH$_3$), 0.90 (9H, s, —C(CH$_3$)$_3$), 1.25 (22H, m, —(CH$_2$)$_{11}$—), 1.34 and 1.57 (2×3H, 2s, (CH$_3$)$_2$—C—), 1.92 (2H, m, =CH—C$\underline{H}_2$—), 3.54 (1 H, m, H-2), 3.86–3.95 and 4.26–4.38 (7H, 2m, H-3', H-4', H-5', H-6' and H-1), 4.51 (1 H, d, J=8.1 Hz, H-1'), 5.22–5.78 (4H, m, H-3, H-4, H-5 and H-2'), 7.30–8.08 (10H, 2m, 2 × —C$_6$H$_5$).

D. (2S,3R,4E)-3-Benzoyloxy-2-hexadecanoylamino-1-(2-O-benzoyl-3,4-O-isopropylidene-6-O-tertbutyl-dimethylsilyl-β-D-galactopyranosyloxy)- 4-octadecene

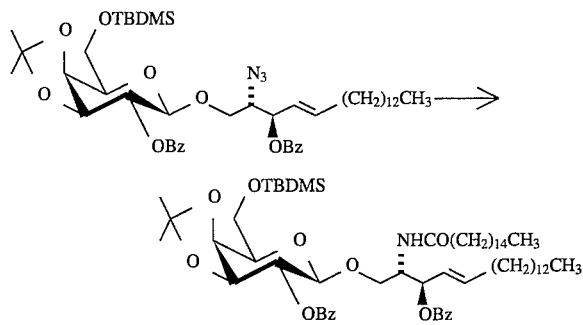

Hydrogen sulfide was bubbled in a solution of (2S,3R,4E)-2-azido-3-benzoyloxy- 1-(2-O-benzoyl-3,4-O-isopropylidene-6-O-tert-butyldimethylsilyl-β-D-galactopyranosyloxy)- 4-octadecene (572 mg, 0.673 mmol) in pyridine (16 mL) and water (4 mL) at room temperature and for ≈10 minutes. The mixture was then tightly closed and stirred at room temperature overnight. The next day, the same procedure was repeated. The solvents were then evaporated and the residue was co-evaporated with toluene and dissolved in tetrahydrofuran (40 mL). To this stirred solution was added an aqueous solution of sodium acetate (50%, 10 mL) followed by a solution of hexadecanoyl chloride (0.3 mL, 1.02 mmol) in tetrahydrofuran (0.5 mL) at room temperature. The reaction mixture was then diluted with ethyl acetate and washed with a 10% aqueous solution of sodium bicarbonate, water (4x) and brine. The organic layer was dried over anhydrous magnesium sulfate, filtered and concentrated. The residue was purified by silica gel chromatography (40 g, 0% to 18% ethyl acetate/hexane) and afforded the title compound (575 mg, 96%).

$^1$H NMR 200 MHz (CDCl$_3$) δ(ppm): 0.02 and 0.04 (2 - 3H, 2s, —Si(CH$_3$)$_2$), 0.85–0.91 (6H, m overlapping —C(CH$_3$)$_3$, 2 × —CH$_2$—CH$_3$), 0.86 (9H, s, —C(CH$_3$)$_3$), 1.13–1.38 (48H, m, —(CH$_2$)$_{11}$— and —(CH$_2$)$_{13}$—), 1.34 and 1.60 (2 x 3H, 2s, (CH$_3$)$_2$—C—), 1.74 (2H, ap t, J=7.5 Hz, =CH—C$\underline{H}_2$—), 1.98 (2H, m, —C$\underline{H}_2$CONH—), 3.57 (1 H, dd, J=3.9 and 9.9 Hz, H-1), 3.69–3.89 (3H, m, H-6' and H-5'), 4.11 (1 H, dd, J=3.1 and 9.9 Hz, H-1), 4.25–4.36 (3H, m, H-2, H-3' and H-4'), 4.41 (1 H, d, J=8.1 Hz, H-1'), 5.19 (1 H, dd, J=7.1 and 8.0 Hz, H-3), 5.40–5.52 (2H, m, H-2' and H-4), 5.71 (1 H, d overlapping H-5, J=9.3 Hz, —NH—), 5.77 (1 H, dt, J=14.3 and 6.9 Hz, H-5), 7.39 (10H, 3m, 2 x —C$_6$H$_5$).

E. (2S,3R,4E)-3-Benzoyloxy-2-hexadecanoylamino-1-(2-O-benzoyl- 6-O-tert-butyldimethylsilyl-β-D-galactopyranosyloxy)- 4-octadecene

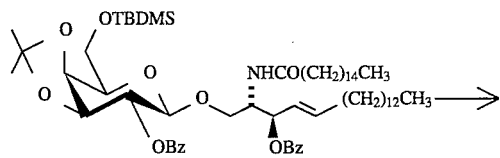

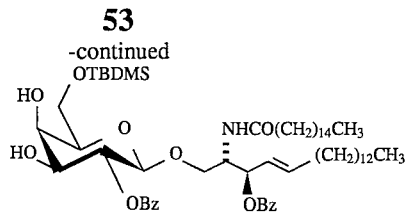

Trifluoroacetic acid (90%,~4 mL) was added to a stirred solution of (2S,3R,4E)-3-benzoyloxy-2-hexadecanoylamino-1-(2-O-benzoyl-3,4-O-isopropylidene- 6-O-tert-butyldimethylsilyl-β-D-galactopyranosyloxy)-4-octadecene (575 mg, 0.649 mmol) in dichloromethane (75 mL) at 22° C. The reaction was stirred at 22° C. and monitored by TLC. The solvents were evaporated and the residue was dissolved in ethyl acetate. The organic layer was washed with a 10% aqueous solution of sodium bicarbonate, water and brine, dried over anhydrous magnesium sulfate, filtered and concentrated.

The residue was dissolved in pyridine (25 mL) and treated with tert-butyldimethylsilylchloride (425 mg, 2.82 mmol) at −15° C. The reaction mixture was stirred at −15° C. overnight, then methanol was added. The mixture was stirred again for 2 more hours at 22° C. The reaction was then poured into water and diluted with ethyl acetate (150 mL). The organic layer was washed with water (5x) and brine, dried over anhydrous magnesium sulfate, filtered and concentrated. The residue was purified by silica gel chromatography and afforded the title compound.

$^1$H NMR 400 MHz (CDCl$_3$) δ(ppm): 0.01 and 0.03 (2 x 3H, 2s, —Si(CH$_3$)$_2$), 0.86 (9H, s overlapping —CH$_3$, —C(CH$_3$)$_3$), 0.86–0.90 (6H, m, 2 x —CH$_2$—CH$_3$), 1.10–1.26 (46H, m, —(CH$_2$)$_{10}$— and —(CH$_2$)$_{13}$—), 1.64 (2H, m, —CH$_2$—), 1.78 (2H, t, J=7.6 Hz, =CH—CH$_2$—), 1.98 (2H, m, —CH$_2$CONH—), 3 48 (1 H, t, H-5'), 3.60 (1H, dd, J=9.4 and 3.4 Hz, H-1), 3.66 (1H, dd, J=10.5 and 4.3 Hz, H- 6'), 3.75–3.81 (2H, m, H-6' and H-3'), 4.07 (1 H, d, J=3.1 Hz, H-4'), 4.13 (1H, d, H-1), 4.42 (1 H, m. H-2), 4.48 (1 H, d, J=7.8 Hz, H-1'), 5.25 (1 H, dd, J=8.8 and 8.8 Hz, H-2'), 5.44 (1 H, dd, J=15.3 and 7.6 Hz, H-4), 5.53 (1 H, dd, J=7.4 and 7.4 Hz, H-3), 5.77 (1 H, d, J=9.2 Hz, —NH—), 5.84 (1 H, dt, J=15.3 and 6.7 Hz H-5), 7.43–8.06 (10H, 3m, 2 x —C$_6$H$_5$).

F.
(2S,3R,4E)-3-Benzoyloxy-2-hexadecanoylamino-1-
(2-O-benzoyl-4-O-acetyl- 6-O-tert-butyldimethylsilyl-
β-D-galactopyranosyloxy)-4-octadecene

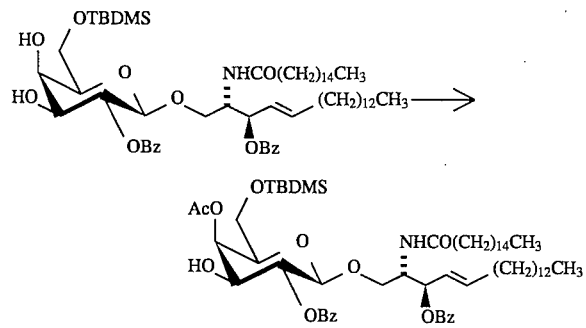

The title compound was prepared using the general procedure described by R. U. Lemieux, et al., *J.A.C.S*, 97, 4069–4075 (1975).

$^1$H NMR 400 MHz (DMSO-d$_6$) δ(ppm): −0.03 and −0.01 (2 x 3H, 2s, —Si(CH$_3$)$_2$), 0.82 (9H, s overlapping —CH$_3$, —C(CH$_3$)$_3$), 0.82–0.85 (6H, m, 2 x —CH$_2$—CH$_3$), 1.13–1.35 (48H, m, —(CH$_2$)$_{11}$— and —(CH$_2$)$_{13}$—), 1.76–1.94 (4H, m, =CH—CH$_2$— and —CH$_2$CONH—), 2.07 (3H, s, CH$_3$CO—), 3.47–3.56 (3H, m, H-6' and H-1), 3.72 (1 H, dd, J=10.0 and 6.5 Hz, H-1), 3.81 (1 H, t, H- 5'), 3.94–3.99 (1 H, m, H-3'), 4.29 (1 H, m, H-2), 4.62 (1 H, d, J=8.0 Hz, H-1'), 5.01 (1 H, dd, J=9.9 and 8.0 Hz, H-2'), 5.24 (1 H, d, J=3.4 Hz, H-4'), 5.30 (1 H, dd, J=7.2 and 4.7 Hz, H-3), 5.37–5.43 (2H, m, H-4 and —NH—), 5.48 (1 H, dt, J=15.2 and 6.3 Hz, H-5), 7.44–7.95 (10H, 4m, 2 x —C$_6$H$_5$).

G.
(2S,3R,4E)-3-Benzoyloxy-2-hexadecanoylamino-1-
(2-O-benzoyl-
4-O-acetyl-β-D-galactopyranosyloxy)-4-octadecene

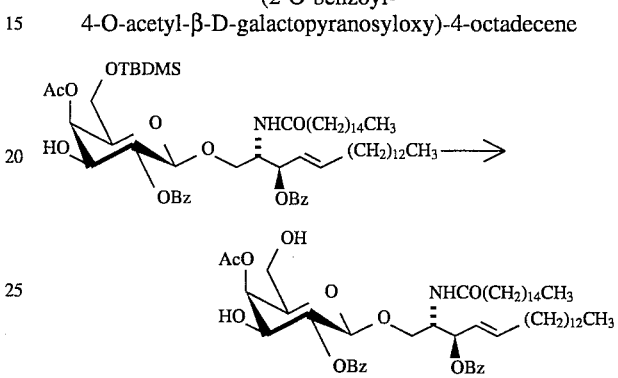

A solution of (2S,3R,4E)-3-benzoyloxy-2-hexadecanoylamino-1-(2-O-benzoyl- 4-O-acetyl-6-O-tert-butyldimethylsilyl-β-D-galactopyranosyloxy)-4-octadecene (430 mg, 0.484 mmol) in tetrahydrofuran (40 mL) was treated with tetrabutylammonium fluoride (1M solution in tetrahydrofuran, 5 mL, 0.5 mmol) at −15° C. The reaction was stirred for 36 hours at 0° C., then diluted with ethyl acetate and washed with water (4x), 10% aqueous sodium bicarbonate solution (3x) and water with solid sodium bicarbonate (3x). The organic layer was dried over anhydrous magnesium sulfate, filtered and concentrated. The resulting white solid was used for the next reaction without further purification.

$^1$H NMR 400 MHz (CDCl$_3$) δ(ppm): 0.89 (6H, m, 2 x —CH$_3$), 1.19–1.41 (48H, m, —(CH$_2$)$_{11}$— and —(CH$_2$)$_{13}$—), 1.44 (2H, br s, 2 x —OH), 1.90 (2H, t, J=7.7 Hz, —CH$_2$CONH—), 2.00 (2H, m, =CH—CH$_2$—), 2.26 (3H, s, CH$_3$CO—), 3.41 (1 H, dd, J=11.9 and 5.8 Hz, H-6'), 3.58 (1H, dd, J=11.9 and 6.6 Hz, H-6'), 3.64–3.70 (2H, m, H-5' and H-3'), 3.99 (1 H, dd, J=10.0 and 3.6 Hz, H-1), 4.03 (1 H, dd, J=10.0 and 2.8 Hz, H-1), 4.47 (1 H, m, H-2), 4.55 (1 H, d, J=7.9 Hz, H-1'), 5.26 (1H, dd, J=10.0 and 7.9 Hz, H-2'), 5.29 (1H, d, J=3.8 Hz, H-4'), 5.48 (1 H, dd, J=15.3 and 7.7 Hz, H-4), 5.60 (1 H, dd, J=7.7 and 7.7 Hz, H-3), 5.71 (1H, d, J=9.3 Hz, —NH—), 5.87 (1H, dt, J=15.3 and 6.8 Hz, H-5), 7.43–8.06 (10H, 3m, 2 x —C$_6$H$_5$).

H.
(2S,3R,4E)-3-Benzoyloxy-2-hexadecanoylamino-1-
[2-O-benzoyl- 4-O-acetyl-3,6-di-O-(sodium
oxysulfonyl)-β-D-galactopyranosyloxy]-4-octadecene

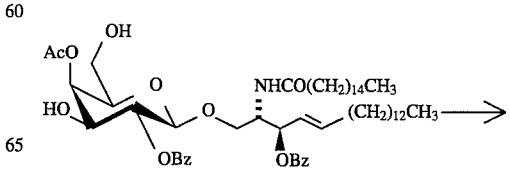

-continued

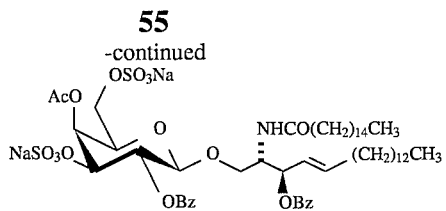

Pyridine sulfur trioxide complex (234 mg, 1.47 mmol) was added to a stirred solution of (2S,3R,4E)-3-benzoyloxy-2-hexadecanoylamino-1-(2-O-benzoyl- 4-O-acetyl-β-D-galactopyranosyloxy)-4-octadecene (100 mg, 0.105 mmol) in pyridine (5 mL) under argon and at 22° C. The mixture was stirred for 36 hours then cooled down to 5° C. and treated with an aqueous sodium bicarbonate solution (1M, 4 mL). This resulting mixture was stirred for ~1 hour at 5° C. and evaporated. The residue was dissolved in dichloromethane/methanol (8:2) and filtered. The filtrate was evaporated and the residue was purified by silica gel chromatography (15 g, 0% to 20% methanol/chloroform) to afford the title compound (94 mg, 77%) as a white solid.

IR (nujol) $\upsilon_{max}$ (cm$^{-1}$): 3700–3150 (N—H), 2730, 2860 (C—H), 1725 (C=O ester), 1645 (C=O amide).

$^1$H NMR 400 MHz (DMSO-d$_6$) δ(ppm): 0.85 (6H, m, 2 x —CH$_3$), 1.10–1.40 (48H, m, —(CH$_2$)$_{11}$— and —(CH$_2$)$_{13}$—), 1.74 (2H, m, =CH—C$\underline{H}_2$—), 1.94 (2H, m, —C$\underline{H}_2$CONH—), 2.08 (3H, s, CH$_3$CO—), 3.47 (1 H, dd, J=9.3 and 7.8 Hz, H-1), 3.61 (1 H, dd, J=11.1 and 7.7 Hz, H-6'), 3.74–3.78 (2H, m, H-1 and H-6'), 4.07 (1H, dd, J=7.7 and 3.7 Hz, H-5'), 4.27 (1 H, m, H-2), 4.57 (1H, dd, J=10.3 and 3.3 Hz, H-3'), 4.72 (1H, d, J=8.0 Hz, H-1'), 5.09 (1H, dd, J=10.3 and 8.0 Hz, H-2'), 5.29 (1 H, dd, J=6.9 and 4.3 Hz, H-3), 5.34–5.43 (2H, m, H-4 and H-5), 5.46 (1 H, d, J=3.3 Hz, H-4'), 7.41–7.99 (10H, 4m, 2 x —C$_6$H$_5$), 7.67 (1H, d, J=9.0 Hz, —NH—).

EXAMPLE 9

(2S,3R,4E)-3-Hydroxy-2-hexadecanoylamino-1-[3,6-di-O-(sodium oxysulfonyl)-β-D-galactopyranosyloxy]-4-octadecene

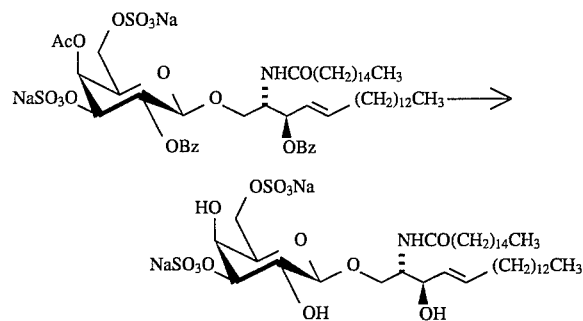

To a freshly prepared solution of sodium methoxide (0.87M, 2 mL, 1.374 mmol) in methanol at 5° C. was added a solution of (2S,3R,4E)-3-benzoyloxy- 2-hexadecanoylamino-1-[2-O-benzoyl-4-O-acetyl-3,6-di-O-(sodium oxysulfonyl)-β-D-galactopyranosyloxy]-4-octadecene (100 mg, 0.087 mmol) in methanol/dichloromethane (1:1, 3 mL). The mixture was stirred at 22° C. and under argon for 1.5 hours, then neutralized with Dowex 50W8 (H$^+$) resin and diluted with methanol/chloroform (1:1, 10 mL) and water (1 mL). The resin was filtered and washed with methanol/chloroform (1:1, 20 mL) and water (2 mL). The flitrate was then treated with Amberlite IRP-64 100–300 mesh (Na$^+$) resin for ≈15 minutes at 22° C. and filtered. The resin was washed with methanol/chloroform (1:1, 20 mL) and water (2 mL) and the filtrate was concentrated under vacuum. The residue was purified by silica gel chromatography (20 g, 0% to 16% methanol/chloroform then 20:100:0.5 to 28:100:1.5 methanol/chloroform/water) and afforded the title compound (43 mg, 55%) as a white solid.

IR (nujol) $\upsilon_{max}$ (cm$^{-1}$): 3700–3100 (O—H and N—H), 2730, 2860 (C—H), 1640 (C=O amide).

$^1$H NMR (DMSO-d$_6$) δ(ppm): 0.84 (6H, t, J=6.7 Hz, 2 x —CH$_3$), 1.22–1.43 (48H, m, —(CH$_2$)$_{11}$— and —(CH$_2$)$_{13}$—), 1.91 (2H, m, =CH—C$\underline{H}_2$—), 2.01 (2H, t, J=7.3 Hz, —C$\underline{H}_2$CONH—), 3.41–3.50 (2H, m, H-1 and H-6'), 3.58 (1 H, ap t, J=5.9 Hz, H-5'), 3.73–3.87 (5H, m, H-1, H-6', H-2', H-4' and H-3), 3.94 (1 H, dd overlapping H-2, J=9.8 and 3.3 Hz, H-3'), 3.93–3.96 (1 H, m, H-2), 4.15 (1 H, d, J=7.7 Hz, H-1'), 4.56, 4.86, 5.09 (3H, 3s, 3 x —OH), 5.34 (1H, dd, J=15.3 and 6.9 Hz, H-4), 5.51 (1H, dt, J=15.3 and 6.6 Hz, H-5), 7.48 (1H, d, J=8.9 Hz, —NH—).

EXAMPLE 10

(2S,3R,4E)-3-Benzoyloxy-2-hexadecanoylamino-1-[2,3-di-O-(sodium oxysulfonyl)-4,6-O-benzylidene-β-D-galactopyranosyloxy)-4-octadecene A.
(2S,3R,4E-3-Benzoyloxy-2-hexadecanoylamino-1-[4,6-O-benzylidene-β-D-galactopyranosyloxy)-4-octadecene

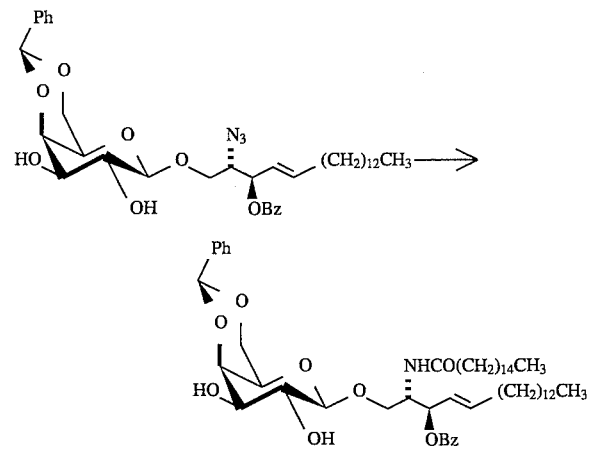

A solution of (2S,3R,4E)-2-azido-3-benzoyloxy-1-( 4,6-O-benzylidene-β-D-galactopyranosyloxy)- 4-octadecene prepared in Example 1-C (235 mg, 0.34 mmol) in pyridine (10 mL) and water (2.5 mL) was saturated with hydrogen sulfide for ≈15 minutes at 22° C. The reaction mixture was then tightly closed and stirred for 8 hours. The solution was saturated again with hydrogen sulfide and stirred overnight. The same procedure was repeated the next day. The solvents were evaporated under vacuum and the residue was co-evaporated with toluene.

This residue was then dissolved in tetrahydrofuran (14 mL) and an aqueous solution of sodium acetate (50%, 1.8 mL) was added to this solution followed by a solution of hexadecanoyl chloride (0.1 mL, 0.34 mmol) in tetrahydrofuran (0.1 mL). The resulting mixture was stirred for one hour at 22° C., then dissolved with ethyl acetate (40 mL) and washed with a 1M aqueous solution of sodium bicarbonate (2×20 mL), water (2×20 mL) and brine (20 mL). The organic layer was dried over anhydrous magnesium sulfate, filtered and concentrated. The residue was purified by silica gel chromatography (20 g, 0% to 90% ethyl acetate/hexane) and afforded the title compound (230 mg, 76%) as a white solid.

IR (CH$_2$Cl$_2$) $\upsilon_{max}$ (cm$^{-1}$): 3055, 2930, 2860 (C—H), 1720 (C=O ester), 1640 (C=O amide), 1265 (C—O).

$^1$H NMR 400 MHz (CDCl$_3$) δ(ppm): 0.88 (6H, t, J=6.3 Hz, 2 x —CH$_3$), 1.24 (44H, br s, —(CH$_2$)$_{10}$— and —(CH$_2$)$_{12}$—), 1.60 (4H, br s, 2 x —CH$_2$—), 2.03 (2H, m, =CH—CH$_2$—), 2.19 (2H, t, J=7.5 Hz, —CH$_2$CONH—), 3.48–4.34 (9H, m, H-1, H-1', H-2', H-3', H-4', H-5' and H-6'), 4.52 (1 H, m, H-2), 5.44–5.63 (3H, m, H- 3, H-4 and —O—CH—O—), 5.88 (1H, dt, J=14.8 and 6.7 Hz, H-5), 6.21 (1 H, d, J=9.2 Hz, —NH—), 7.34–8.05 (10H, 2m, 2 x —C$_6$H$_5$).

B.
(2S,3R,4E)-3-Benzoyloxy-2-hexadecanoylamino-1-[2,3-di-O-(sodium oxysulfonyl)-4,6-O-benzylidene-β-D-galacto-pyranosyloxy)-4-octadecene

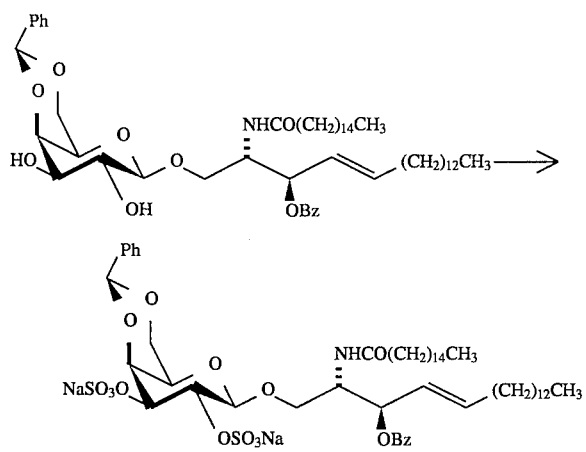

Trimethylamine sulfur trioxide complex (103 mg, 0.74 mmol) was added to a stirred solution of (2S,3R,4E)-3-benzoyloxy-2-hexadecanoylamino-1-( 4,6-O-benzylidene-β-D-galactopyranosyloxy)-4-octadecene (66 mg, 0.074 mmol) in dry dimethylformamide (6 mL) at 22° C. and under argon. The mixture was stirred at 85° C. for 1 hour and then cooled down to 5° C. and treated with a 1M aqueous solution of sodium bicarbonate until the pH reached 8–9. The resulting mixture was stirred for 0.75 hour. The solvents were evaporated under vacuum and the residue was dissolved in a mixture of methanol/chloroform (2:8). This solution was filtered on Celite and the filtrate was evaporated under vacuum. The residue was purified on silica gel plate (chloroform/methanol 8:2) and afforded the title compound (70 mg, 86%) as a white solid.

IR (CH$_2$Cl$_2$) $\upsilon_{max}$ (cm$^{-1}$): 3700–3150 (N—H), 2925, 2860 (C—H), 1725 (C=O ester), 1650 (C=O amide), 1265 (C—O, S=O).

$^1$H NMR 400 MHz (DMSO-d$_6$) δ(ppm): 0.84 (6H, t, J=6.9 Hz, 2 x —CH$_3$), 1.18–1.27 (46H, br s, —(CH$_2$)$_{11}$— and —(CH$_2$)$_{12}$—), 1.42 (2H, m, —CH$_2$—), 1.93 (2H, m, =CH—CH$_2$—), 2.00–2.19 (2H, m, —CH$_2$CONH—), 3.40 (1 H, dd, J=10.0 and 3.5 Hz, H-1), 3.50 (1 H, s, H-5'), 3.86 (1 H, d, J$_{AB}$=11.1 Hz, H-6'), 3.96 (1H, d, J$_{AB}$=11.1 Hz, H-6'), 4.09–4.14 (1H, m overlapping H-1, H-3'), 4.13 (1 H, dd, J=10.0 and 3.3 Hz, H-1), 4.25 (1 H, m, H-2), 4.31 (1 H, dd, J=9.9 and 7.8 Hz, H-2'), 4.37 (1H, d, J=7.8 Hz, H-1'), 4.57 (1H, d, J=3.3 Hz, H-4'), 5.38–5.48 (3H, m, —O—CH—O—, H-3 and H-4), 5.71 (1H, dt, J=14.5 and 7.7 Hz, H-5), 7.30–7.99 (10H, 4m, 2 x —C$_6$H$_5$), 8.30 (1 H, d, J=9.0 Hz, —NH—).

EXAMPLE 11

(2S,3R,4E)-3-Benzoyloxy-2-hexadecanoylamino-1-[2,3-di-O-(sodium oxysulfonyl)-β-D-galactopyranosyloxy)-4-octadecene

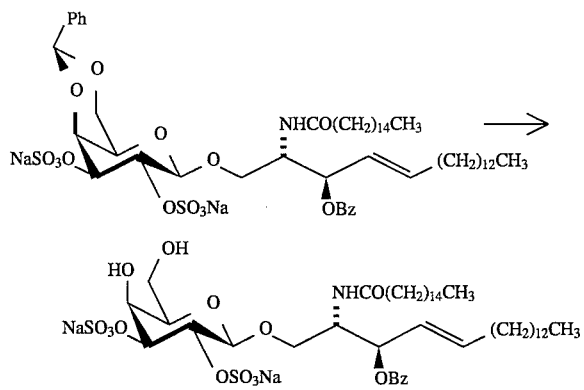

(2S,3R,4E)-3-Benzoyloxy-2-hexadecanoylamino-1-[2,3-di-O-(sodium oxysulfonyl)-4,6-O-benzylidene-β-D-galactopyranosyloxy)-4-octadecene (140 mg, 0.128 mmol) was treated with trifluoroacetic acid (90%, 1 mL) at 5° C. and this solution was stirred for =10 minutes at 5° C. and for 30 minutes at 22° C. The solvents were evaporated under vacuum and the residue was co-evaporated with toluene. After purification of the residue on silica gel plate (chloroform/methanol/water, 7:3:1), the resulting product was dissolved in dichloromethane/methanol (1:1) and treated with Amberlite IRP-64 100–300 mesh (Na$^+$) resin. The solution was filtered and evaporated. The residue was purified on silica gel plates (chloroform/methanol/water 6:3.5:0.5) and afforded the title compound (70.5 mg, 55%) as a white solid.

IR (nujol) $\upsilon_{max}$ (cm$^{-1}$): 3700–3150 (O—H and N—H), 2920, 2855 (C—H), 1720 (C=O ester), 1650 (C=O amide), 1265 (C—O, S=O).

$^1$H NMR 400 MHz (DMSO-d$_6$) δ(ppm): 0.82 (6H, t, J=6.9 Hz, 2 x —CH$_3$), 1.18–1.24 (46H, m, —(CH$_2$)$_{11}$— and —(CH$_2$)$_{12}$—), 1.41 (2H, m, —CH$_2$—), 1.92 (2H, m, =CH—CH$_2$—), 1.98–2.16 (2H, m, —CH$_2$CONH—), 3.27–3.33 (3H, m, H-1, H-5' and H-6'), 3.41 (1H, dd, J=8.3 and 4.4 Hz, H-6'), 3.90 (1H, m, H-2), 4.06 (1H, d, J=8.3 Hz, H-1), 4.19–4.22 (4H, m, H-1', H-2', H-3' and H-4'), 4.51 (2H, br s, 2 x —OH), 5.33 (1H, t, J=7.6 Hz, H-3), 5.38 (1H, dd, J=14.6 and 7.6 Hz, H-4), 5.69 (1H, dt, J=14.6 and 7.0 Hz, H-5), 7.48–7.97 (5H, 3m, —C$_6$H$_5$), 8.37 (1 H, d, J=9.2 Hz, —NH—).

EXAMPLE 12

(2S,3R,4E)-3-Hydroxy-2-hexadecanoylamino-1-[2,3di-O-(sodium oxysulfonyl)-β-D-galactopyranosyloxy)-4-octadecene

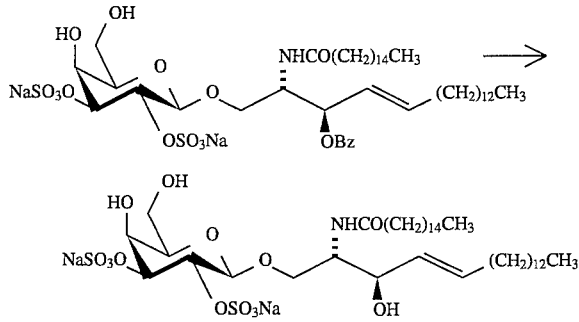

A solution of (2S,3R,4E)-3-benzoyloxy-2-hexadecanoylamino-1-[2,3-di-O-(sodium oxysulfonyl)-β-D-galactopyranosyloxy)-4-octadecene (46 mg, 0.045 mmol) in dichloromethane/methanol (1:1, 3 mL) was added slowly to a stirred solution of sodium methoxide in methanol (0.45M, 2 mL, 0.9 mmol) at 22° C. and under argon. This mixture was stirred for 2.5 hours, then sodium methoxide in methanol solution was added again (0.45M, 0.3 mL, 0.15 mmol). The mixture was stirred for one more hour and neutralized with Dowex 50W8 (H⁺) resin. The resin was filtered and washed with dichloromethane-methanol (1:1). The filtrate was treated with Amberlite IRP- 64 100–300 mesh (Na⁺) resin for 1 hour. The solution was filtered and evaporated under vacuum. The residue was purified on silica gel plates (chloroform/methanol/water 6:3.5:0.5) and afforded the title compound (26 mg, 64%) as a white solid.

IR (nujol) $\upsilon_{max}$ (cm$^{-1}$): 3700–3150 (O—H and N—H), 2925, 2855 (C—H), 1650 (C=O amide).

$^1$H NMR 400 MHz (DMSO-d$_6$) δ(ppm): 0.84 (6H, t, J=6.8 Hz, 2 x —CH$_3$), 1.22–1.46 (48H, m, —(CH$_2$)$_{11}$— and —(CH$_2$)$_{13}$—), 1.88 (2H, m, =CH—C$\underline{H}_2$—), 1.93–2.11 (2H, m, —C$\underline{H}_2$CONH—), 3.09 (1 H, dd, J=9.2 and 2.7 Hz, H-1), 3.35 (1H, dd, t, J=6.2 Hz, H-5'), 3.45 (1H, dd, J=10.8 and 6.2 Hz, H-6'), 3.51 (1H dd, J=10.8 and 6.2 Hz, H-6'), 3.67 (1 H, br t, H-3), 3.84–3.92 (2H, m, H-2 and H-1), 4.11 (1H, d, J=3.9 Hz, —OH), 4.18–4.25 (4H, m, H-1', H-2', H-3' and H- 4'), 4.62 (1 H, t, J=5.7 Hz, —OH-6'), 4.77 (1 H, d, J=5.8 Hz, —OH), 5.29 (1 H, dd, J=15.4 and 7.1 Hz, H-4), 5.45 (1 H, dt, J=15.4 and 6.6 Hz, H-5), 8.06 (1 H, d, J=9.4 Hz, —NH—).

EXAMPLE 13

(2S,3R,4E)-3-Benzoyloxy-2-hexanoylamino-1-[3,4-O-isopropylidene- 2,6-di-O-(sodium oxysulfonyl)-β-D-galactopyranosyloxy]-4-octadecene.

A. (2S,3R,4E)-3-Benzoyloxy-2-hexanoylamino-1-(β-D-galactopyranosyloxy)- 4-octadecene

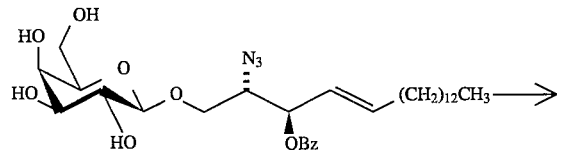

Hydrogen sulfide was bubbled in a stirred solution of (2S,3R,4E)-2-azido-3-benzoyloxy- 1-(β-D-galactopyranosyloxy)-4-octadecene prepared as described in Example 1-B (0.52 g, 0.879 mmol) in pyridine (10 mL) and water (10 mL) at room temperature and for ≈30 minutes until saturation of the solution. This mixture was stirred at room temperature for 18 hours. The solvents were evaporated under vacuum. The residue was then dissolved in tetrahydrofuran (20 mL) and a solution of sodium acetate (50%, 20 mL) was added to this solution, followed by hexanoyl chloride (0.14 mL, 1.00 mmol). This reaction mixture was then stirred at room temperature for 45 minutes. The aqueous phase was separated and extracted with tetrahydrofuran (2×40 mL). The combined organic phases were then washed with brine (4 mL) and concentrated. The residue obtained was purified by silica gel chromatography (28 g, 0% to 20% methanol/ethyl acetate) and afforded the title compound (0.35 g, 60%) as a white amorphous solid.

[α]$_D^{22}$: +3.8° (c=1.0, MeOH).

IR (KBr) $\upsilon_{max}$ (cm$^{-1}$): 3700–3100 (N—H and O—H), 2925, 2860 (C—H), 1720 (C=O ester), 1645 (C=O amide), 1270 (C—O).

$^1$H NMR 400 MHz (DMSO-d$_6$) δ(ppm): 0.82 (3H, t, J=6.7 Hz, —CH$_3$), 0.85 (3H, t, J=6.5 Hz, —CH$_3$), 1.21–1.32 (26H, m, —(CH$_2$)$_{11}$— and —(CH$_2$)$_2$—), 1.42–1.49 (2H, m, —CH$_2$—), 2.00 (2H, m, =CH—C$\underline{H}_2$—), 2.04–2.14 (2H, m, —NHCOC$\underline{H}_2$—), 3.24–3.35 and 3.46–3.52 (3H and 2H, 2m, H-1, H-6', H-2', H- 3' and H-5'), 3.41 (1 H, dd, J=10.8 and 5.5 Hz, H-6'), 3.62 (1 H, dd, J=3.9 and 3.9 Hz, H-4'), 3.87 (1H, dd, J=10.1 and 5.3 Hz, H-1), 4.05 (1 H, d, J=7.4 Hz, H-1'), 4.31–4.35 (1 H, m overlapping —OH, H-2), 4.35 (1 H, d, J=4.4 Hz, —OH), 4.49 (1 H, t, J=5.5 Hz, —OH-6'), 4.70 (1 H, d, J=5.4 Hz, —OH), 4.92 (1 H, d, J=3.9 Hz, —OH-4'), 5.45–5.56 (2H, m, H-3 and H-4), 5.80 (1 H, dt, J=14.4 and 7.2 Hz, H-5), 7.49–7.96 (5H, 3m, —C$_6$H$_5$), 7.78 (1H, d, J=9.0 Hz, —NH—).

B. (2S,3R, 4E)-3-Benzoyloxy-2-hexanoylamino-1-(3,4-O-isopropylidene-β-D-galactopyranosyloxy)-4-octadecene

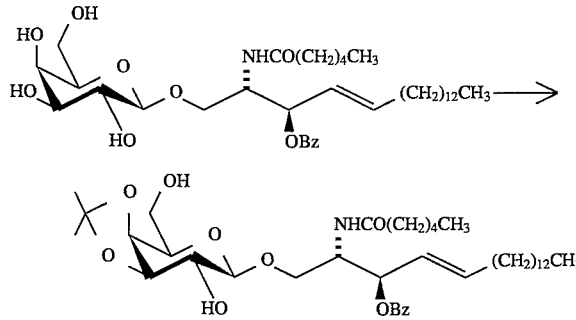

(2S,3R,4E)-3-Benzoyloxy-2-hexanoylamino-1-(β-D-galacto-pyranosyloxy)- 4-octadecene (0.52 g, 0.783 mmol) was reacted by the general procedure as described in Example 5-C and afforded the title compound (0.48 g, 87%).

IR (CH$_2$Cl$_2$) $\upsilon_{max}$ (cm$^{-1}$): 3700–3100 (O—H and N—H), 2915, 2855 (C—H), 1720 (C=O ester), 1645 (C=O amide), 1270 (C—O).

¹H NMR 400 MHz (DMSO-d₆) δ(ppm): 0.82 (3H, t, J=6.9 Hz, —CH₃), 0.85 (3H, t, J=6.9 Hz, —CH₃), 1.21–1.32 (26H, m, —(CH₂)₁₁— and —(CH₂)₂—), 1.25 and 1.38 (2 X 3H, 2s, —C(CH₃)₂), 1.44–1.51 (2H, m, —CH₂—), 2.00 (2H, m, =CH—CH₂—), 2.06–2.12 (2H, m, —NHCOCH₂—), 3.22 (1 H, ddd, J=7.5, 7.5 and 4.4 Hz, H-2'), 3.44–3.54 (3H, m, H-1 and H-6'), 3.71 (1 H, td, J=6.4 and 1.8 Hz, H-5'), 3.88 (1 H, dd, J=10.1 and 5.4 Hz, H-1), 3.92 (1 H, dd, J=6.9 and 5.7 Hz, H-3'), 4.08–4.11 (1H, m overlapping H-1', H-4'), 4.10 (1H, d, J=8.1 Hz, H-1'), 4.34 (1H, m, H-2), 4.70 (1H, t, J=5.6 Hz, —OH-6'), 5.22 (1H, d, J=4.4 Hz, —OH-2'), 5.47 (1H, dd, J=7.6 and 5.7 Hz, H-3), 5.53 (1H, dd, J=14.8 and 7.6 Hz, H-4), 5.79 (1 H, dt, J=14.7 and 6.7 Hz, H-5), 7.48–7.96 (5H, 3m, —C₆H₅), 7.78 (1 H, d, J=9.1 Hz, —NH—).

C.
(2S,3R,4E)-3-Benzoyloxy-2-hexanoylamino-1-[3,4-O-isopropylidene- 2,6-di-O-(sodium oxysulfonyl)-β-D-galactopyranosyloxy]-4-octadecene

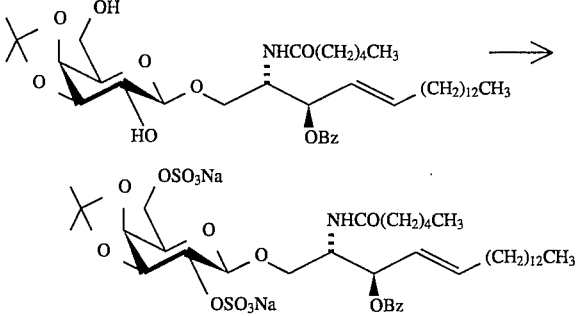

(2S,3R,4E)-3-Benzoyloxy-2-hexanoylamino-1-(3,4-O-isopropylidene-β-D-galactopyranosyloxy)- 4-octadecene (0.20 g, 0.284 mmol) was reacted by the general procedure as described in Example 5-D and afforded the title compound (0.25 g, 97%) as a white amorphous solid.

[α]$_D^{22}$:+8.8° (c=1.0, MeOH).

IR (KBr) υ$_{max}$ (cm⁻¹): 3700–3150 (N—H), 2930, 2860 (C—H), 1725 (C=O ester), 1635 (C=O amide), 1265 (C—O), 1225 and 1005 (S=O).

¹H NMR 400 MHz (DMSO-d₆) δ(ppm): 0.82 (3H, t, J=7.2 Hz, —CH₃), 0.85 (3H, t, J=6.7 Hz, —CH₃), 1.17–1.48 (31H, m, —(CH₂)₁₁—, —(CH₂)₃— and —C(CH₃)₂), 1.36 (3H, s, —C(CH₃)₂), 1.97 (2H, m, =CH—CH₂—), 2.08 (2H, m, —NHCOCH₂—), 3.40 (1 H, dd, J=10.2 and 4.6 Hz, H-1), 3.75–3.82 (2H, m, H- 6'), 3.86 (1H, td, J=6.2 and 1.7 Hz, H-5'), 3.96 (1H, dd, J=10.2 and 3.6 Hz, H-1), 4.11–4.14 (2H, m, H-3' and H-4'), 4.25 (1 H, dd overlapping H-2, J=6.3 and 5.3 Hz, H-2'), 4.22–4.28 (1H, m, H-2), 4.48 (1H, d, J=5.3 Hz, H-1'), 5.39 (1H, dd, J=7.2 and 7.2 Hz, H-3), 5.46 (1H, dd, J=15.1 and 7.6 Hz, H-4), 5.73 (1 H, dt, J=15.1 and 6.8 Hz, H-5), 7.48–7.98 (5H, 3m, —C₆H₅), 8.08 (1 H, d, J=9.1 Hz, —NH—).

EXAMPLE 14

(2S,3R,4E)-3-Benzoyloxy-2-hexanoylamino-1-[2,6-di-O-(sodium oxysulfonyl)-β-D-galactopyranosyloxy]-4-octadecene

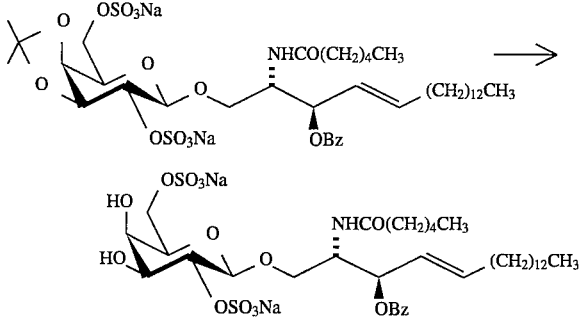

(2S,3R,4E)-3-Benzoyloxy-2-hexanoylamino-1-[3,4-O-isopropylidene- 2,6-di-O-(sodium oxysulfonyl)-β-D-galactopyranosyloxy]-4-octadecene (0.23 g, 0.253 mmol) was treated by the general procedure as described in Example 5-E and afforded the title compound (0.22 g, 100%) as a white amorphous solid.

[α]$_D^{22}$: –6.5° (c=1.0, MeOH).

IR (KBr) υ$_{max}$ (cm⁻¹): 3700–3100 (N—H and O—H), 2930, 2860 (C—H), 1685 (C=O amide and ester), 1210 (C—O and S=O).

¹H NMR 400 MHz(DMSO-d₆) δ(ppm): 0.80 (3H, t, J=7.0 Hz, —CH₃), 0.85 (3H, t, J=6.9 Hz, —CH₃), 1.20–1.28 (26H, m, —(CH₂)₁₁— and —(CH₂)₂—), 1.40–1.49 (2H, m, —CH₂—), 1.97 (2H, ap qa, J=6.9 Hz, =CH—CH₂—), 2.04–2.20 (2H, m, —NHCOCH₂—), 3.46–3.51 (2H, dd, m, H-1 and H-3'), 3.59 (1 H, br t, H-5'), 3.63 (1 H, dd, J=4.1 and 4.1 Hz, H-4'), 3.76 (1 H, dd, J=10.6 and 6.4 Hz, H-6'), 3.83 (1H, dd, J=10.6 and 5.7 Hz, H-6'), 3.97 (1H, dd, J=9.8 and 4.6 Hz, H-1), 4.16 (1H, dd, J=9.4 and 7.8 Hz, H-2'), 4.16 (1H, d overlapping H-2, J=7.8 Hz, H-1'), 4.23–4.29 (1 H, m, H-2), 4.70 (1H, d, J=4.1 Hz, OH-4'), 5.12 (1H, s, —OH-3'), 5.41 (1 H, dd, J=7.4 and 7.4 Hz, H-3), 5.47 (1 H, dd, J=14.8 and 7.4 Hz, H-4), 5.76 (1H, dt, J=14.8 and 6.8 Hz, H-5), 7.49–7.98 (5H, 3m —C₆H₅), 7.75 (1 H, d, J=8.8 Hz, —NH—).

EXAMPLE 15

(2S,3R,4E)-3-Hydroxy-2-hexanoylamino-1-[2,6-di-O-(sodium oxysulfonyl)-β-D-galactopyranosyloxy]-4-octadecene

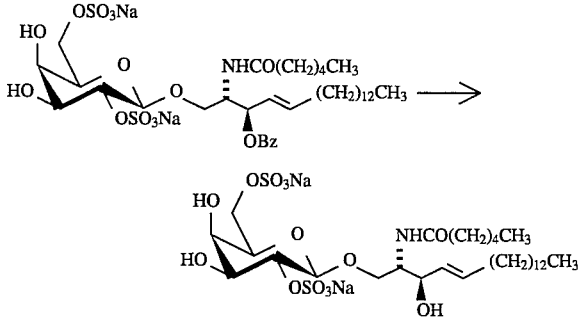

(2S,3R,4E)-3-Benzoyloxy-2-hexanoylamino-1-[2,6-di-O-(sodium oxysulfonyl)-β-D-galactopyranosyloxy]-4-octadecene (0.16 g, 0.184 mmol) was treated by the general procedure as described in Example 6-A and afforded the title compound (0.12 g, 86%) as a white amorphous solid.

$[\alpha]_D^{22}$: −1.1° (c=1.0, MeOH).

IR (KBr) $\upsilon_{max}$ (cm$^{-1}$): 3700–3050 (N—H and O—H), 2930, 2860 (C—H), 1680 (C=O amide), 1210 (C—O and S=O).

$^1$H NMR 400 MHz (DMSO-d$_6$) δ(ppm): 0.82–0.87 (6H, m, 2 X —CH$_3$), 1.18–1.29 (28H, m, —(CH$_2$)$_{11}$— and —(CH$_2$)$_3$—), 1.40–1.49 (2H, m, =CH—CH$_2$—), 2.03–2.14 (2H, m, —NHCOCH$_2$—), 3.25–3.31 (1 H, m, H-1), 3.48 (1 H, dd, J=9.6 and 3.3 Hz, H-3'), 3.58 (1 H, t, J=6.2 Hz, H-5'), 3.62 (1 H, br s, H-4'), 3.67–3.87 (4H, m, H-3, H-6' and H-1), 4.10 (1 H, dd overlapping H-2, J=9.6 and 7.6 Hz, H-2'), 4.08–4.15 (1H, m, H-2), 4.24 (1H, d, J=7.6 Hz, H-1'), 4.69 (1H, br s, —OH), 4.86 (1 H, d, J=5.3 Hz, —OH), 4.96 (1 H, br s, —OH), 5.31 (1H, dd, J=15.4 and 7.1 Hz, H-4), 5.49 (1 H, dt, J=15.4 and 6.7 Hz, H-5), 7.41 (1 H, d, J=9.2 Hz, —NH—).

EXAMPLE 16

(2S,3R,4E)-3-Benzoyloxy-1-[2,3-di-O-benzoyl-4,6-di-O-(sodium oxysulfonyl)-β-D-glucopyranosyloxy]-2-(cis-15-tetracosanoylamino)-4-octadecene

A.
(2S,3R,4E)-3-Benzoyloxy-1-(2,3-di-O-benzoyl-4,6-O-benzylidene-β-D-glucopyranosyloxy)-2-(cis-15-tetracosenoylamino)-4-octadecene

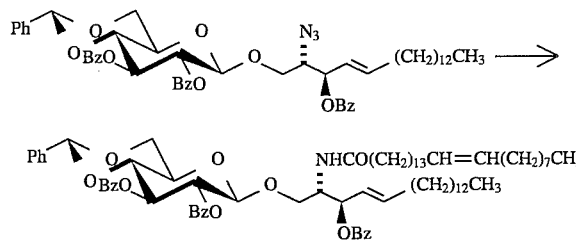

(2S,3R,4E)-2-Azido-3-benzoyloxy-1-(2,3-di-O-benzoyl-4,6-O-benzylidene-β-D-glucopyranosyloxy)- 4-octadecene prepared in Example 3-D (120 mg, 0.135 mmol) was reacted by the general procedure as described in Example 5-A and afforded the title compound (132 mg, 81%) as an off-white gum.

IR (CH$_2$Cl$_2$) $\upsilon_{max}$ (cm$^{-1}$): 3440 (N—H), 1735, 1675 (C=O).

$^1$H NMR 400 MHz (CDCl$_3$) δ(ppm): 0.89 (6H, t, J=6.8 Hz, 2 x —CH$_3$), 1.1–1.5 (56H, m, 2x —(CH$_2$)$_{11}$— and —(CH$_2$)$_6$—), 1.84 (2H, t, J=7.6 Hz, —CH$_2$CONH—), 2.02–2.15 (6H, m, 3 x =CH—CH$_2$—), 3.57 (1 H, dd, J=9.9 and 4.1 Hz, H-6'), 3.62 (1 H, dd, J=10.0 and 7.1 Hz, H-1), 3.55–3.60 (1 H, m H-5'), 3.90 (1 H, t, J=9.3 Hz, H-4'), 4.04 (1 H, dd, J=9.6 and 3.8 Hz, H-1), 4.18 (1 H, dd, J=9.4 and 2.2 Hz, H-6'), 4.43–4.48 (1H, m, H-2), 4.72 (1H, d, J=7.6 Hz, H-1'), 5.37 (2H, br t, J=4.7 Hz, —CH=CH-cis), 5.43 (1 H, dd, J=9.2 and 7.6 Hz, H-2'), 5.49 (1 H, s, —O—CH—O—), 5.4–5.5 (2H, m overlapping H-2', H-4 and H-3), 5.65 (1 H, d, J=9.5 Hz, —NH—), 5.77 (1 H, t, J=9.4 Hz, H-3'), 5.89 (1 H, dt, J=14.6 and 6.7 Hz, H-5) 7.29–7.60 and 7.95–8.07 (15H, m, 3 x —C$_6$H$_5$).

B.
(2S,3R,4E)-3-Benzoyloxy-1-(2,3-di-O-benzoyl-β-D-glucopyranosyloxy)-2-cis-15-tetracosenoyl-amino-4-octadecene

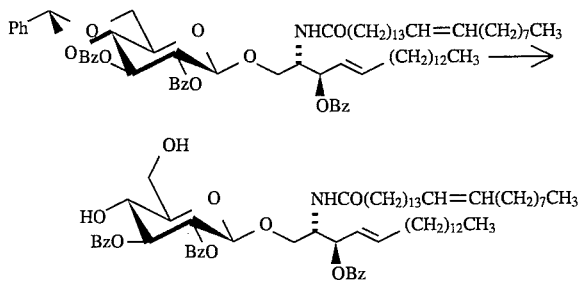

(2S,3R,4E)-3-Benzoyloxy-1-(2,3-di-O-benzoyl-4,6-O-benzylidene-β-D-glucopyranosyloxy)- 2-(cis-15-tetracosenoylamino)-4-octadecene (129 mg, 0.1 mmol) was reacted by the general procedure as described in Example 1-F and afforded the title compound (105 mg, 88%) as a white solid.

IR (CH$_2$Cl$_2$) $\upsilon_{max}$ (cm$^{-1}$): 3600, 3440 (O—H and N—H), 3060, 2930, 2860 (C—H), 1730, 1675 cm$^1$ (C=O).

$^1$H NMR 400 MHz (CDCl$_3$) δ(ppm): 0.89 (6H, t, J=6.8 Hz, 2 x —CH$_3$), 1.21–1.60 (56H, m, 2 x —(CH$_2$)$_{11}$— and (CH$_2$)$_6$—), 1.90–2.04 (8H, m, 3 x =CH—CH$_2$—) and —C H$_2$CONH—), 2.86 (1 H, br s, —OH), 3.39 (1 H, dt, J=9.5 and 3.0 Hz, H-5'), 3.59 (1H, dd, J=12.5 and 2.6 Hz, H-6'), 3.63 (1H, dd, J=9.5 and 3.8 Hz, H-1), 3.75 (1 H, dd, J=12.5 and 3.5 Hz, H-6'), 4.01 (1 H, dd, J=9.5 and 1.7 Hz, H-1), 4.09 (1H, br t, J=8.7 Hz, H-4'), 4.45–4.50 (1H, m, H-2), 4.65 (1H, d, J=7.5 Hz, H-1'), 5.36 (2H, br t, J=4.6 Hz, —HC=CH-cis), 5.39 (1 H, dd, J=9.7 and 7.3 Hz, H-2'). 5.45 (1 H, dd, J=9.9 and 8.8 Hz, H-3), 5.50 (1 H, dd, J=15.3 and 8.3 Hz, H-4), 5.67 (1 H, t, J=8.5 Hz, H-3'), 5.77 (1 H, d, J=9.6 Hz, —NH—), 5.92 (1 H, dt, J=15.3 and 6.7 Hz, H-5), 7.37–7.62, 7.95–7.99 and 8.05–8.08 (15 H, 3 sets of m, 3 x —C$_6$H$_5$).

C.
(2S,3R,4E)-3-Benzoyloxy-1-[2,3-di-O-benzoyl-4,6-di-O-(sodium oxysulfonyl)-β-D-glucopyranosyloxy]-2-(cis-15-tetracosanoylamino)- 4-octadecene

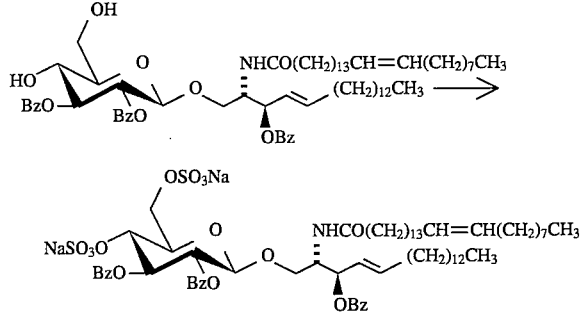

(2S,3R,4E)-3-Benzoyloxy-1-(2,3-di-O-benzoyl-β-D-glucopyranosyloxy)-2-(cis- 15-tetracosenoylamino)-4-octadecene (100 mg, 0.09 mmol) was reacted by the general procedure as described in Example 1-G and afforded the title compound (98 mg, 83%) as a white solid.

IR (Nujol) $\upsilon_{max}$ (cm$^{-1}$): 3600–3300, 3440 (N—H), 1730 and 1660 (C=O).

$^1$H NMR 400 MHz (DMSO-d$_6$) δ(ppm): 0.827 (3H, t, J=6.7 Hz, —CH$_3$), 0.833 (3H, t, J=6.7 Hz, —CH$_3$), 1.15–1.38 (56H, m, 2 x —(CH$_2$)$_{11}$— and —(CH$_2$)$_6$—), 1.75–1.86, 1.88–2.03 (8H, 2 sets of m, 3 x =CH—CH$_2$— and —CH$_2$CONH—), 3.57 (1 H, dd, J=9.6 and 7.1 Hz, H-1), 3.66 (1 H, dd, J=10.4 and 9.4 Hz, H-6'), 3.82 (2H, br dd, H-1 and H-5'), 4.14 (1 H, t, J=9.5 Hz, H-4'), 4.24–4.29 (1 H, m, H-2), 4.36 (1H, br d, J=10.4 Hz, H-6'), 4.88 (1H, d, J=7.9 Hz, H-1'), 5.05 (1H, dd, J=9.7 and 8.1 Hz, H-2'), 5.25–5.34 (3H, m, —CH=CH-cis and H-3), 5.39 (1H, dd, J=15.4 and 7.2 Hz, H-4), 5.47 (1H, dd, J=15.4 and 6.3 Hz, H-5), 5.54 (1 H, t, J=9.4 Hz, H-3'), 7.34–7.61, 7.74–7.87 (15H, 2 sets of m, 3 x —C$_6$H$_5$).

EXAMPLE 17

(2S,3R,4E)-3-Hydroxy-1-[4,6-di-O-(sodium oxysulfonyl)-β-D-glucopyranosyloxy]- 2-(cis-15-tetracosanoylamino)-4-octadecene

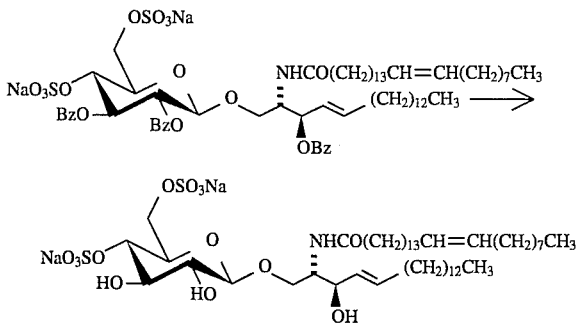

(2S,3R,4E)-3-Benzoyloxy-1-[2,3-di-O-benzoyl-4,6-di-O-(sodium oxysulfonyl)-β-D-glucopyranosyloxy]-2-(cis-15-tetracosanoylamino)-4-octadecene is reacted by the general procedure as described in Example 2-A and the title compound is thereby produced.

EXAMPLE 18

(2S,3R,4E)-2-Hexadecanoylamino-3-benzoyloxy-1-[2,3-di-O-benzyl-4,6-di-O-(sodium oxysulfonyl)-β-D-galactopyranosyloxy]-4-octadecene

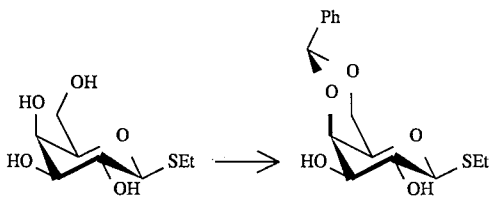

A. Ethyl 4,6-O-benzylidene-1-thio-β-D-galactopyranoside

Benzaldehyde dimethylacetal (2.0 mL, 13.3 mmol) followed by paratoluenesulfonic acid (15 mg) were added to a stirred solution of ethyl 1-thio-β-D-galactopyranoside (1.3 g, 5.80 mmol) in acetonitrile (20 mL) at 22° C. The mixture was stirred for 1 hour, then triethylamine (≈3 mL) was added and the mixture was evaporated under vaccum. The residue was dissolved in ethyl acetate and washed with water and a 1M aqueous solution of sodium bicarbonate. The organic layer was dried over anhydrous magnesium sulfate, filtered and concentrated. The residue was precipitated from ethyl acetate/hexane and afforded the title compound (1.3 g, 72%) as a white solid.

$^1$H NMR 400 MHz (CDCl$_3$) δ(ppm): 1.35 (3H, t=J=7.4 Hz, —CH$_3$), 2.57 (1 H, s, —OH), 2.59 (1 H, d, J=10.1 Hz, —OH), 2.70–2.90 (2H, m, —SCH$_2$—), 3.54 (1 H, d, J=1.3 Hz, H-5), 3.69 (1H, ddd, J=12.3, 9.1 and 3.5 Hz, H-3), 3.82 (1 H, ddd, J=10.5, 9.2 and 1.4 Hz, H-2), 4.04 (1H, dd, J=12.5 and 1.8 Hz, H-6), 4.27 (1 H, dd, J=3.6 and 1.0 Hz, H-4), 4.36 (1 H, dd, J=12.3 and 1.8 Hz, H-6), 4.35 (1H, d, J=9.5 Hz, H-1), 3.55 (1H, s, —O—CH—O—), 7.34–7.52 (5H, m, —C$_6$H$_5$).

B. Ethyl 2,3-di-O-benzyl-4,6-O-benzylidene-1-thio-β-D-galactopyranoside

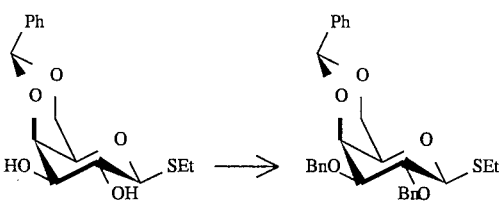

A solution of ethyl 4,6-O-benzylidene-1-thio-β-D-galactopyranoside (1.3 g, 4.17 mmol) in tetrahydrofuran (20 mL) was added to sodium hydride (980 mg, 60% suspension in oil, 24.5 mmol, washed with hexane) at 22° C. and this solution was stirred for 30 minutes. The solution was cooled down to 0° C. and a solution of benzyl bromide (≈2 mL, ≈17 mmol) in dimethylformamide (12 mL) was added. The resulting mixture was stirred at 22° C. for ≈1 hour, then poured in a cold 1M aqueous solution of sodium bicarbonate and extracted with ethyl acetate. The organic layers were washed with a 1M aqueous solution of sodium bicarbonate and water, dried over anhydrous magnesium sulfate, filtered and evaporated. The residue was purified by trituration with ethyl acetate (≈5 mL) and hexane (≈150 mL) and afforded the title compound (1.24 g, 60%) as a white solid.

$^1$H NMR 200 MHz (CDCl$_3$) δ(ppm): 1.33 (1H, t, J=6.4 Hz, —CH$_3$), 2.69–2.88 (2H, m, —CH$_2$S—), 3.36 (1 H, br s, H-5), 3.59 (1 H, dd, J=9.1 and 3.4 Hz, H-3), 3.89 (1H, t, J=9.4 Hz, H-2), 3.96 (1H, dd, J=12.3 and 1.8 Hz, H-6), 4.16 (1H, d, J=3.4 Hz, H-4), 4.31 (1H, dd, J=12.3 and 1.4 Hz, H-6), 4.44 (1H, d, J=9.6 Hz, H-1), 4.76 (2H, br s, CH$_2$-benzyl), 4.83 (1 H, d, J$_{AB}$=10.2 Hz, CH$_2$-benzyl), 4.87 (1 H, d, J$_{AB}$=10.2 Hz, CH$_2$-benzyl), 5.48 (1H, s, —O—CH—O—), 7.28–7.57 (5H, m, —C$_6$H$_5$).

C.
(2S,3R,4E)-2-Azido-3-benzoyloxy-1-(2,3-di-O-benzyl-4,6-O-benzylidene-β-D-galactopyranosyloxy)-4-octadecene
and
(2S,3R,4E)-2-azido-3-benzoyloxy-1-(2,3-di-O-benzyl-4,6-O-benzylidene-α-D-galactopyranosyloxy)-4-octadecene

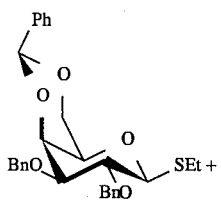

67
-continued

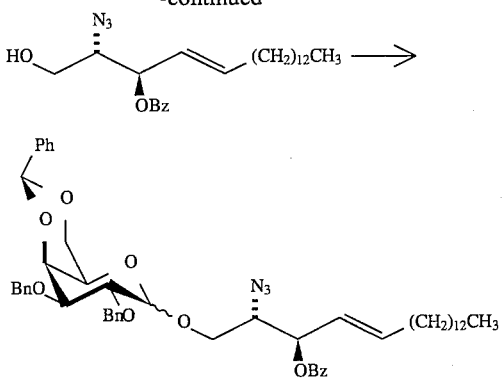

A solution of (2S,3R,4E)-2-azido-3-benzoyloxy-4-octadecen-1-ol (0.60 g, 1.40 mmol), ethyl 2,3-di-O-benzyl-4,6-O-benzylidene-1-thio-β-D-galactopyranoside (1.4 g, 2.85 mmol) and 2,6-di-tert-butyl-4-methylpyridine (0.2 g, 0.974 mmol) in a mixture of toluene (30 mL) and dichloromethane (30 mL) was stirred for 1 hour at 22° C. with powdered 4 Å molecular sieves. Then dimethyl(methylthio)sulfonium triflate (0.6 g, 2.33 mmol) was added and the resulting mixture was stirred for 1 hour. Triethylamine (2 mL) was then added and the reaction mixture was stirred for another 30 minutes. The reaction mixture was then filtered through Celite, diluted with ethyl acetate, washed with an aqueous solution of sodium bicarbonate and brine, dried over anhydrous magnesium sulfate and concentrated. Chromatography of the residue on a silica gel pad gave the α-anomer (942 mg, 78%) and the β-anomer (257 mg, 21%) of the title compound.

IR ($CH_2Cl_2$) $\upsilon_{max}$ ($cm^{-1}$) α-anomer: 3060, 2930, 2860 (C—H), 2110 (—$N_3$) and 1720 (C=O).

$^1$H NMR 400 MHz ($CDCl_3$) δ(ppm) α-anomer: 0.89 (3H, t, J=6.8 Hz, —$CH_3$), 1.25–1.38 (22H, m, —($CH_2$)$_{11}$—), 2.04–2.09 (2H, m, =CH—$CH_2$), 3.58 (1 H, dd, J=10.9 and 7.5 Hz, H-1), 3.67 (1 H, br s, H-5'), 3.73 (1 H, dd, J=10.9 and 4.7 Hz, H-1), 3.92–3.97 (1H, m, H-2), 4.00 (1H, dd, J=10.1 and 3.4 Hz, H-3'), 4.01 (1H, dd, J=12.5 and 1.5 Hz, H-6'), 4.09 (1H, dd, J=10.1 and 3.4 Hz, H- 2'), 4.19 (1 H, d, J=3.4, H-4'), 4.21 (1H, dd, J=12.5 Hz and 1.3 Hz, H-6'), 4.68 (1H, d, $J_{AB}$=12.0 Hz, $CH_2$-benzyl), 4.74 (1H, d, $J_{AB}$=12.2 Hz, $CH_2$-benzyl), 4.83 (1H, d, $J_{AB}$=12.2 Hz, $CH_2$-benzyl), 4.85 (1H, d, $J_{AB}$=12.0 Hz, $CH_2$-benzyl), 4.93 (1 H, d, J=3.4 Hz, H-1'), 5.49 (1 H, s, —O—CH—O—), 5.58 (1 H, dd, J=14.7 and 8.1 Hz, H-4), 5.63 (1 H, dd, J=8.1 and 4.1 Hz, H-3), 5.90 (1 H, dt, J=14.7 and 6.7 Hz, H-5), 7.22–7.61 and 8.06–8.08 (20 H, 2 sets of m, 4 x —$C_6H_5$).

$^1$H NMR 400 MHz ($CDCl_3$) δ(ppm) β-anomer: 0.89 (3H, t, J=6.8 Hz, —$CH_3$), 1.24–1.33 (22H, m, —($CH_2$)$_{11}$—), 1.99–2.04 (2H, m, =CH—$CH_2$—), 3.33 (1 H, br s, H-5'), 3.57 (1 H, dd, J=9.6 and 3.6 Hz, H-3'), 3.61 (1 H, d, J=4.7 Hz, H-1), 3.89 (1 H, dd, J=9.6 and 7.8 Hz, H-2'), 3.98–4.05 (3H, m, H-6', H-2 and H-1), 4.12 (1H, d, J=3.5 Hz, H-4'), 4.30 (1H, d, J=12.5 Hz, H-6'), 4.41 (1H, d, J=7.8 Hz, H-1'), 4.76 (1H, d, $J_{AB}$=12.4 Hz, $CH_2$ of benzyl), 4.78 (1H, d, $J_{AB}$=12.4 Hz, $CH_2$ of benzyl), 4.84 (1H, d, $J_{AB}$=10.8 Hz, $CH_2$ of benzyl), 4.94 (1 H, d, $J_{AB}$=10.8 Hz, $CH_2$ of benzyl), 5.50 (2H, s, —O—CH—O—), 5.57 (1 H, dd, J=15.4 and 7.9 Hz, H-4), 5.68 (1H, dd, J=7.9 and 3.2 Hz, H-3), 5.88 (1H, dd, J=15.3 and 6.7 Hz, H-5), 7.28–7.59 and 8.06–8.09 (20H, 3 sets of m, 4 x —$C_6H_5$).

68

D. (2S,3R,4E)-2-Hexadecanoylamino-3-benzoyloxy-1-(2,3-di-O-benzyl- 4,6-O-benzylidene-β-D-galactopyranosyloxy)-4-octadecene

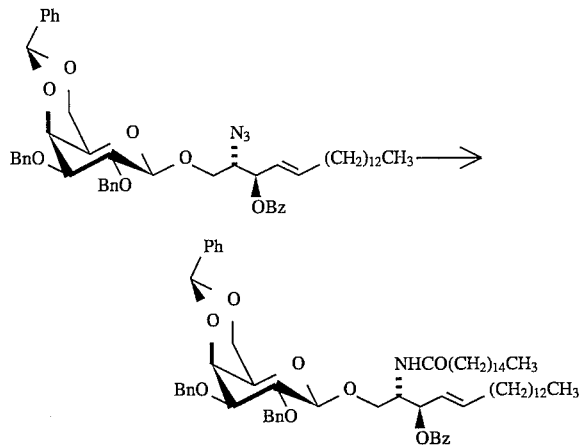

(2S,3R,4E)-2-Azido-3-benzoyloxy-1-(2,3-di-O-benzyl- 4,6-O-benzylidene-β-D-galactopyranosyloxy)- 4-octadecene (254 mg, 0.30 mmol) was reacted by the general procedure as described in Example 1-E and afforded the title compound (265 mg, 84%) as a white solid.

IR ($CH_2Cl_2$) $\upsilon_{max}$ ($cm^{-1}$): 3440, 3400–3300 (N—H), 3060, 2860 (C—H), 1720 and 1672 (C=O).

$^1$H NMR 400 MHz ($CDCl_3$) δ(ppm): 0.89 (3H, t, J=6.9 Hz, —$CH_3$), 0.89 (3H, t, J=7.1, —$CH_3$), 1.14–1.48 (48H, m, —($CH_2$)$_{11}$—), 1.75–1.90 (2H, m, —$CH_2$CONH—), 1.96–2.01 (2H, m, =CH—$CH_2$), 3.32 (1 H, br s, H-5'), 3.58 (1H, dd, J=9.6 and 3.6 Hz, H-3'), 3.70 (1H, dd, J=11.2 and 3.9 Hz, H-1), 3.87 (1H dd, J=9.6 and 7.9 Hz, H-2'), 4.00 (1H, dd, J=12.4 and 1.4 Hz, H-6'), 4.14 (1 H, d, J=3.5 Hz, H-4'), 4.23 (1 H, dd, J=11.2 and 3.4 Hz, H-1), 4.25 (1H dd, J=12.1 and 1.1 Hz, H-6'), 4.34 (1H, d, J=7.8 Hz, H-1'), 4.41–4.47 (1H, m, H-2), 4.77 (2H, s, $CH_2$ of benzyl), 4.78 (1 H, d, $J_{AB}$=10.9 Hz, $CH_2$ of benzyl), 4.89 (1H, d, $J_{AB}$=10.9 Hz, $CH_2$ of benzyl), 5.46 (1H, dd, J=15.3 and 7.3 Hz, H-4), 5.49 (1 H, s, —OH), 5.59 (1 H, t, J=7.3 Hz, H-3), 5.80 (1H, dt, J=15.3 and 6.7 Hz, H-5), 6.10 (1 H, d, J=9.1 Hz, —NH—), 7.29–7.44 (15H, m, 3 x —$C_6H_5$), 7.52–7.56 and 8.04–8.06 (5H, m, —$C_6H_5$).

E. (2S,3R,4E)-2-Hexadecanoylamino-3-benzoyloxy-1-( 2,3-di-O-benzyl-β-D-galactopyranosyloxy)-4-octadecene

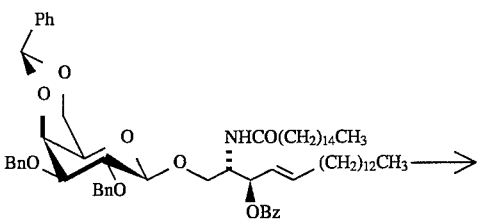

-continued

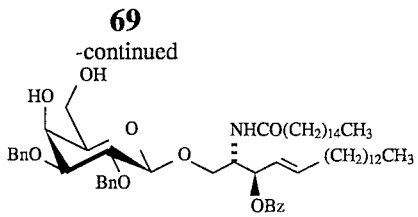

(2S,3R,4E)-2-Hexadecanoylamino-3-benzoyloxy-1-(2,3-di-O-benzyl- 4,6-O-benzylidene-β-D-galactopyranosyloxy)-4-octadecene (260 mg, 0.24 mmol) was reacted by the general procedure as described in Example 1-F and afforded the title compound (206 mg, 86%) as white solid.

IR (CH$_2$Cl$_2$) $\upsilon_{max}$ (cm$^{-1}$): 3600–3400 (O—H, N—H), 3060, 2860 (C—H), 1720 and 1675 (C=O).

$^1$H NMR 400 MHz (CDCl$_3$) δ(ppm): 0.89 (6H, t, –J=6.5 Hz, 2 x —CH$_3$), 1.23–1.32 (47H, m, —(CH$_2$)$_{11}$— and —(CH$_2$)$_{12}$—), 1.50–1.54 (2H, m, —CH$_2$—), 1.91–2.05 (4H, m, =CH—CH$_2$ and —CH$_2$CONH—), 3.36–3.39 (1 H, m, H-5), 3.48 (1 H, dd, J=9.3 and 3.3 Hz, H-3'), 3.70 (1H, dd, J=9.5 and 7.8 Hz, H-2'), 3.69–3.73 (1 H, m, H-6'), 3.76 (1 H, dd, J=10.9 and 4.6 Hz, H-1), 3.90 (1 H, dd, J=12.1 and 6.1 Hz, H-6'), 4.01 (1 H, d, J=3.0 Hz, H-4'), 4.06 (1 H, dd, J=10.8 and 2.9 Hz, H-1), 4.33, (1 H, d, J=7.8 Hz, H-1'), 4.50–4.55 (1 H, m, H-2), 4.73 (1 H, d J$_{AB}$=11.9 Hz, CH$_2$ of benzyl), 4.74 (1 H, d, J$_{AB}$=11.9 Hz, CH$_2$ of benzyl), 4.82 (2H, t, J=11.4 Hz, CH$_2$ of benzyl), 5.49 (1 H, dd, J=15.3 and 7.7 Hz, H-4), 5.67 (1 H, t, J=7.7 Hz, H-3), 5.87 (1 H, dt, J=15.3 and 6.6 Hz, H-5), 5.84 (1H, d, J=9.2 Hz, —NH—), 7.28–8.06 (15H, m, 3 x —C$_6$H$_5$).

F.
(2S,3R,4E)-2-Hexadecanoylamino-3-benzoyloxy-1-[2,3-di-O-benzyl- 4,6-di-O-(sodium oxysulfonyl)-β-D-galactopyranosyloxy]-4-octadecene

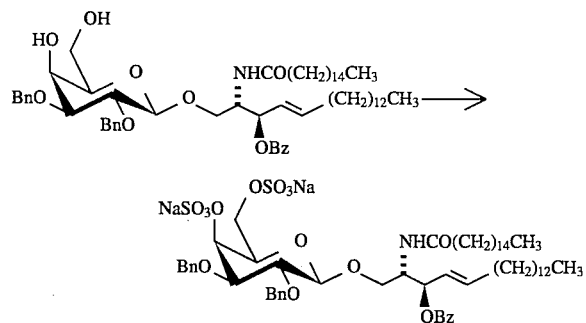

(2S,3R,4E) 2-Hexadecanoylamino-3-benzoyloxy-1-(2,3-di-O-benzyl-β-D-galactopyranosyloxy)- 4-octadecene (250 mg, 0.25 mmol) was reacted by the general procedure as described in Example 1-G and afforded the title compound (273 mg, 92%).

IR (Nujol) $\upsilon_{max}$ (cm$^{-1}$): 3600–3250 (N—H), 1710 and 1650 (C=O).

$^1$H NMR 400 MHz (DMSO-d$_6$) δ(ppm): 0.83 (6H, t, J=6.8 Hz, 2 x —CH$_3$), 1.17–1.30, 1.30–1.45 (50H, m, —(CH$_2$)$_{13}$— and —(CH$_2$)$_{11}$—), 1.94–2.11 (4H, m, =CH—CH$_2$— and —CH$_2$CONH—), 3.32 (1 H, dd, J=9.4 and 7.5 Hz, H-2'), 3.52 (1 H, dd, J=9.5 and 2.9 Hz, H-3'), 3.54–3.57 (1 H, m, H-5'), 3.66 (1 H, dd, J=8.1 and 1.9 Hz, H-1), 3.87 (1H, dd, J=11.8 and 8.3 Hz, H-6'), 3.871, 3.893, 3.914 (1 H, dd, J=8.4 Hz, H-1), 4.10 (dd, J=11.8 and 2.4 Hz, H-6'), 4.30 (1 H, d, J=7.4 Hz, H-1'), 4.38–4.46 (1H, m, H-2), 4.33 (1H, d, J$_{AB}$=11.6 Hz, CH$_2$ of benzyl), 4.59 (1 H, d, J$_{AB}$=11.4 Hz, CH$_2$ of benzyl), 4.61 (1H, d, J=2.9 Hz, H- 4'), 4.72 (1 H, d, J$_{AB}$=11.4 Hz, CH$_2$ of benzyl), 4.88 (1 H, d, J$_{AB}$=11.6 Hz, CH$_2$ of benzyl), 5.49 (1H, dd, J=7.6 and 4.4 Hz, H-3), 5.54 (1H, dd, J=14.7 and 7.6 Hz, H-4), 5.71 (1H, dt, J=14.7 and 6.6 Hz, H-5), 7.19–7.94 (15H, 5 sets of m, 3 x —C$_6$H$_5$) and 7.89 (1 H, d, J=8.9 Hz, —NH—).

EXAMPLE 19

(2S,3R)-3-Benzoyloxy-1-(2,3-di-O-benzoyl-4,6-di-O-(sodium oxysulfonyl)-β-D-galactopyranosyloxy)-2-tetracosanoyl-aminooctadecane A.
(2R,3R)-1,3-O-Benzylidene-octadecane-1,2,3-triol

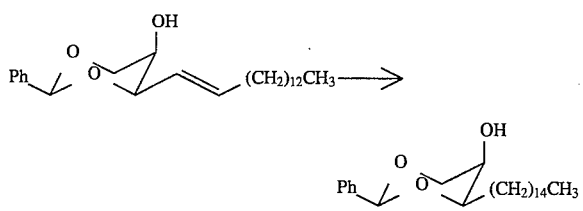

A solution of (2R,3R,4E)-1,3-O-benzylidene-4-octadecen-1,2,3-triol (3.00 g, 7.72 mmol) in a mixture of ethyl acetate (100 mL) and 0.02M sodium methoxide in methanol (100 mL) was hydrogenated over 0.35 g of 10% Pd on activated carbon at 22° C. and under 1 atm of hydrogen for 1 hour. Acetic acid (0.2 mL) was added and the catalyst was filtered. The filtrate was evaporated under vacuum and the residue was filtered on a silica gel pad using a mixture of ethyl acetate and toluene (5:95) as eluent to give 2.88 g (95%) of the title material as a white solid.

m.p. 64°–65° C. (hexane); [α]$_D^{22}$: +6.0° (c=1.0, CHCl$_3$).
IR (KBr) $\upsilon_{max}$ (cm$^{-1}$): 3450 (OH).
$^1$H NMR 400 MHz (CDCl$_3$) δ(ppm): 0.89 (3H, t, J=7.0 Hz, —CH$_3$), 1.2–1.8 (28H, m, —(CH$_2$)$_{14}$—) 3.48 (1 H, broad s, H-2), 3.87 (1 H, broad t, J=7 Hz, H-3), 4.06 (1H, dd, J=1.06and 11.8 Hz, H-1), 4.24 (1H, dd, J=1.85 and 11.8 Hz, H-1), 5.58 (1H, s, —O—CH—O—), 7.3–7.5 (5H, m, —C$_6$H$_5$).

Anal. Calcd. for C$_{25}$H$_{42}$O$_3$: C 76.87; H 10.84. Found: C 75.93; H 10.58.

B.
(2S,3R)-2-Azido-1,3-O-benzylidene-octadecane-1,3-diol

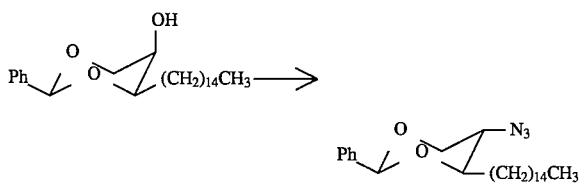

A solution of (2R,3R)-1,3-O-benzylidene-octadecane-1,2,3-triol (2.780 g, 7.11 mmol) in dichloromethane (25 mL) was cooled to −15° C. and treated successively with pyridine (1.16 mL, 14.3 mmol) and triflic anhydride (1.5 mL, 8.9 mmol). After 15 minutes at −15° C., a suspension of powdered sodium azide (2.12 g, 32.7 mmol) in N,N-dimethylformamide (80 mL) was added and the resulting mixture was stirred at 22° C. for 4 hours. The reaction mixture was then diluted with hexane (300 mL) and cold water (200 mL). The aqueous phase was extracted with hexane (2×100 mL) and the combined organic extracts were washed with brine and dried over anhydrous magnesium sulfate. Evaporation of the solvent gave an oil which was diluted with chloroform (50 mL) and methanol (50 mL), treated with p-toluenesulfonic acid (0.080 g) and stirred at 22° C. for 45 minutes. Solid sodium bicarbonate (500 mg) was added and after 15 minutes, the solution was filtered and concentrated under vacuum. Chromatography of the residual oil on silica gel (3×9 cm) using a mixture of hexane and toluene (6:4) gave 2.20 g (74%) of the title material as white needles.

m.p. 53°–53.5° C. (hexane); $[\alpha]_D^{22}$: +32.5° (c=1.0, $CHCl_3$).

IR (KBr) $\upsilon_{max}$ (cm$^{-1}$): 2118.

$^1$H NMR 400 MHz (CDCl$_3$) δ(ppm): 0.9 (3H, t, J=6.9 Hz, —CH$_3$), 1.2–1.9 (28H, m, —(CH$_2$)$_{14}$—), 3.41 (1H, ddd, J=5.2, 11.0 and 11.0 Hz, H-2), 3.58 (1H, ddd, J=2.6, 11.0 and 11.0 Hz, H-3), 3.68 (1 H, dd, J=11.0 Hz, H-1ax), 4.38 (1 H, dd, J=5.2 and 11.0 Hz, H-1 eq), 5.47 (1 H, s, —O—CH—O—), 7.3–7.5 (5H, m, —C$_6$H$_5$).

Anal. Calcd. for $C_{25}H_{41}N_3O_2$: C 72.25; H 9.94; N 10.11. Found: C 72.17; H 9.93; N 10.28.

C. (2S,3R)-2-Azido-octadecane-1,3-diol

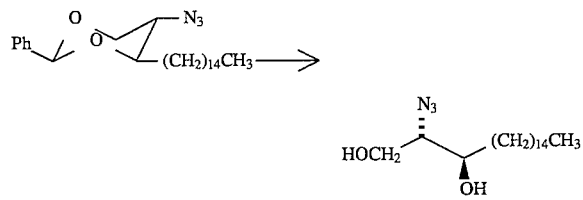

A solution of (2S,3R)-2-azido-1,3-O-benzylidene-octadecane-1,3-diol (2.15 g, 5.17 mmol) in a mixture of chloroform (70 mL) and methanol (70 mL) was treated with p-toluenesulfonic acid (0.080 g) and the resulting mixture was stirred at 22° C. for 70 hours. The resulting mixture was then stirred with sodium bicarbonate (0.5 g) filtered and evaporated. Chromatography of the residue on silica gel using a gradient of methanol in dichloromethane gave 1.38 g (81%) of the title material as a white solid.

m.p. 75°–75.5° C. (hexane); $[\alpha]_D^{22}$: +9.00° (c=1.0, $CHCl_3$).

IR (KBr) $\upsilon_{max}$ (cm$^{-1}$): 3340 (OH), 2150 (N$_3$).

$^1$H NMR 200 MHz (CDCl$_3$) δ(ppm): 0.87 (3H, t, J=6.4 Hz, —CH$_3$), 1.15–1.7 (28 H, m, —(CH$_2$)$_{14}$—), 2.0 (1H, broad, —OH), 3.43 (1H, dt, J=5.0 and 5.0 Hz, H-2), 3.77 (1 H, m, H-3), 3.89 (2H, d, J=5.0 Hz, CH$_2$-1).

Anal. Calcd. for $C_{18}H_{37}N_3O_2$: C 66.01; H 11.39; N 12.83. Found: C 65.84; H 11.44; N 12.92.

D.
(2S,3R)-2-Azido-1-t-butyldimethylsilyl-octadecane-1,3-diol

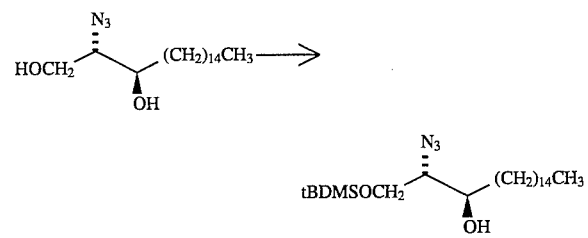

A solution of (2S,3R)-2-azido-octadecane-1,3-diol (1.332 g, 4.06 mmol) in pyridine (15 mL) was treated with tert-butyldimethylsilyl chloride (0.736 g, 4.88 mmol) and the resulting mixture was stirred at 22° C. for 18 hours. Methanol (1 mL) was added and the solvent was evaporated under vacuum. The residue was purified by silica gel chromatography (2×12 cm) using a mixture of ethyl acetate and toluene (2:98) and gave 1.63 g (90%) of the title material as an oil.

$[\alpha]_D^{22}$: +15° (c=1.0, CHCl$_3$).

IR (NaCl, film) $\upsilon_{max}$ (cm$^{-1}$): 3450 (OH), 2100 (N$_3$).

$^1$H NMR 200 MHz (CDCl$_3$) δ(ppm): 0.11 (6H, s, SiCH$_3$), 0.88 (3H, t, J=6.7 Hz, —CH$_3$), 0.91 (9H, s, Si—t—Bu), 1.1–1.8 (29H, m, —(CH$_2$)$_{14}$— and —OH), 3.35 (1 H, dt, J=5.4 and J=5.4 Hz, H-2), 3.7 (1 H, m, H-3), 3.89 (2H, d, J=5.4 Hz, CH$_2$-1).

Anal. Calcd. for $C_{24}H_{51}N_3O_2Si$: C 65.25; H 11.64; N 9.51. Found: C 65.22; H 11.44; N 9.65.

E. (2S,3R)-2-Azido-3-benzoyl-octadecane-1,3-diol

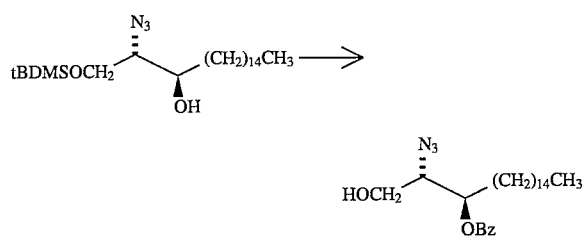

A solution of (2S,3R)-2-azido-1-t-butyldimethylsilyl-octadecane-1,3-diol (1.63 g, 3.69 mmol) in a mixture of toluene (12 mL) and pyridine (12 mL) was treated at 0°–5° C. with benzoyl chloride (1.037 g, 7.38 mmol) and a crystal of 4-dimethylaminopyridine and the resulting mixture was stirred at 0°–5° C. for 48 hours. Methanol (2 mL) was added and the solvent was evaporated under vacuum. The residue was diluted with ethyl acetate (200 mL), washed with cold 0.1N hydrochloric acid, saturated sodium bicarbonate, brine and dried over magnesium sulfate. Evaporation of the solvent gave an oil (2.4 g) which was dissolved in tetrahydrofuran (50 mL) cooled to 0°–5° C. and treated successively with acetic acid (1.38 g) and a 1M solution of tetrabutylammonium fluoride (11 mL, 11.0 mmol) in tetrahydrofuran. After 18 hours at 15° C., the reaction mixture was diluted with ethyl acetate (200 mL) washed with a saturated solution of sodium bicarbonate, brine and dried over anhydrous magnesium sulfate. Evaporation of the solvent under vacuum gave an oil which was purified by silica gel chromatography (3×12 cm). Elution with a mixture of ethyl acetate in toluene (2:98) gave 1.525 (95%) of the title material as an oil.

$[\alpha]_D^{22}$: -16° (c=1.0, CHCl$_3$).

IR (NaCl, film) $\upsilon_{max}$ (cm$^{-1}$): 3450 (OH), 2110 (N$_3$) and 1722 (C=O of benzoate).

$^1$H NMR 400 MHz (CDCl$_3$) δ(ppm): 0.89 (3H, t, J=6.8 Hz, —CH$_3$), 1.15–1.5 and 1.7–1.9 (28H, 2m, —(CH$_2$)$_{14}$—), 2.2 (broad, OH exchanged D$_2$O), 3.65–3.75 and 3.8–3.85 (2H and 1 H, 2m, CH$_2$-1 and H-2), 5.28 (1 H, m, H-3), 7.47, 7.6 and 8.07 (2H, 1H and 2H, 3m, —C$_6$H$_5$).

Anal. Calcd. for $C_{25}H_{41}N_3O_3$: C 69.57; H 9.57; N 9.74. Found: C 69.37; H 9.53; N 9.64.

F. (2S,3R)-2-Azido-3-benzoyloxy-1-(2,3,4,6-tetra-O-acetyl-β-D-galactopyranosyloxy)-octadecane

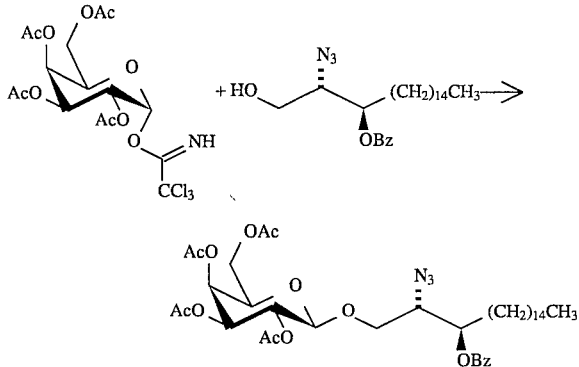

A solution of O-(2,3,4,6-tetra-O-acetyl-α-D-galactopyranosyl)trichloroacetimidate (2.43 g, 4.93 mmol), (2S,3R)-2-azido-3-benzoyl-4-octadecane- 1,3-diol (1.525 g, 3.53 mmol) in a mixture of dichloromethane (30 mL) and hexane (60 mL) was stirred with powdered 4 Å molecular sieves (2 g) for 30 minutes. Then a 0.1M tin (IV) chloride solution in dichloromethane (7 mL) was added dropwise over 1 hour and the resulting mixture was stirred for another 45 minutes. The reaction mixture was then filtered on celite, and the filtrate was diluted with ethyl acetate (200 mL). The organic phase was washed with a saturated solution of sodium bicarbonate and brine, dried over magnesium sulfate and concentrated. Chromatography of the residue on silica gel (4×12 cm) using a mixture of ethyl acetate and toluene (1:9) gave 2.33 g (62%) of the title material as a clear oil.

$[\alpha]_D^{22}$: −22° (c=1.0, $CHCl_3$).

IR (NaCl) $\upsilon_{max}$ ($cm^{-1}$): 2100 ($N_3$), 1750 and 1720 (C=O).

$^1H$ NMR 400 MHz ($CDCl_3$) δ(ppm): 0.88 (3H, s, —$CH_3$), 1.2–1.45 (26H, m —($CH_2)_{13}$—), 1.6–1.9 (2H, m, $CH_2$-4), 1.99, 2.02, 2.07 and 2.16 (4 x 3H, 4 x —$OCOCH_3$), 3.75 (1 H, dd, J=4.3 and J=10.3 Hz, H-1), 3.86–3.92 (2H, m, H- 2 and H-5' overlapping), 3.97 (1H, dd, J=7.1 and 10.3 Hz, H-1), 4.11 (2H, ABX system, H-6'), 4.54 (1H, d, J=7.98 Hz, H-1'), 5.02 (1 H, dd, J=3.43 and 10.5 Hz, H-3'), 5.24 (1 H, dd, J=7.98 and 10.5 Hz, H-2'), 5.26 (1 H, m, H-3), 5.38 (1H, broad d, H-4'), 7.46, 7.60 and 8.06 (2H, 1H and 2H, 3m, —$C_6H_5$).

Anal. Calcd. for $C_{39}H_{59}N_3O_{12}.H_2O$: C 60.06; H 7.88; N 5.39. Found: C 60.15; H 7.63; N 5.32.

G. (2S,3R)-2-Azido-3-benzoyloxy-1-(β-D-galactopyranosyloxy)-octadecane

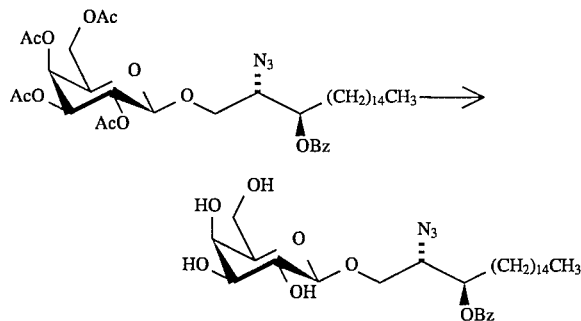

(2S,3R)-2-Azido-3-benzoyloxy-1-(2,3,4,6-tetra-O-acetyl-β-D-galactopyranosyloxy)-octadecane (2.30 g, 3.01 mmol) was reacted by the general procedure as described in Example 1-B and gave 1.340 g (74%) of the title material as a thick syrup.

$[\alpha]_D^{22}$: −21° (c=2.0, MeOH).

IR (NaCl) $\upsilon_{max}$ ($cm^{-1}$): 2100 ($N_3$), 1715 (C=O).

$^1H$ NMR 400 MHz (DMSO-$d_6$) δ(ppm): 4.36 (1 H, d, J=4.5 Hz, —OH), 4.54 (1H, t, J=5.6 Hz, —OH), 4.69 (1H, d, J=5.3 Hz, —OH) and 4.83 (1H, d, J=4.5 Hz, —OH); exchanged $D_2O$ d (ppm): 0.84 (3H, t, J=6.8 Hz, —$CH_3$), 1.1–1.3 (26H, broad, —($CH_2)_{13}$—), 1.55–1.8 (2H, m, $CH_2$-4), 3.26 (1 H, dd, J=3.0, 9.45 Hz, H-3'), 3.30 (1H, dd, J=7.1, 9.45 Hz, H-2'), 3.35 (1H, broad t, H-5'), 3.4–3.55 (2H, m, H-6'), 3.63 (1 H, broad d, J=3 Hz, H-4'), 3.72 (1 H, dd, J=4.25 and 10.6 Hz, H-1), 3.84 (1 H, dd, J=8.4 and 10.6 Hz, H-1), 4.10 (1 H, m, H-2), 4.17 (1 H, d, J=7.1 Hz, H-1'), 5.24 (1 H, m, H-3), 7.54, 7.67 and 7.97 (2H, 1H and 2H, 3m, —$C_6H_5$).

Anal. Calcd. for $C_{31}H_{51}N_3O_8.0.5 H_2O$: C 61.77; H 8.70; N 6.97. Found: C 61.91; H 8.53; N 6.98.

H. (2S,3R)-3-Benzoyloxy-2-tetracosanoylamino-1-(β-D-galactopyranosyloxy)-octadecane

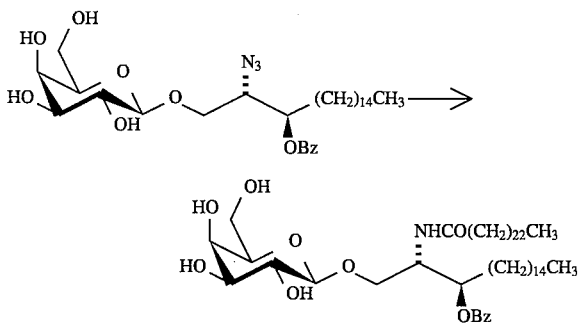

(2S,3R)-2-Azido-3-benzoyloxy-1-(β-D-galactopyranosyloxy)-octadecane (0.972 g, 1.64 mmol) was reacted by the general procedure as described in Example 13-A except that tetracosanoyl chloride was used in place of hexanoyl chloride and gave after chromatography 1.160 g (77%) of the title material as a white amorphous solid.

$[\alpha]_D^{22}$: +5.4° (c=1.1, $CHCl_3$/MeOH 9:1).

IR (KBr) $\upsilon_{max}$ ($cm^{-1}$): 1710 (C=O of ester) and 1642 (C=O of amide).

$^1H$ NMR 400 MHz (DMSO-$d_6$-$CDCl_3$~1%+1 drop $D_2O$) δ(ppm): 0.81 (6H, t, J=7 Hz, 2 x —$CH_3$ overlapping), 1.0–1.8 (70 H, m, —($CH_2)_{14}$— and —($CH_2)_{21}$—), 2.05 (2H, m, —NHCO$CH_2$—), 3.25 (1 H, dd, J=3.1 and 9.5 Hz, H-3'), 3.31 (1 H, dd, J=7.3 and 9.5 Hz, H-2'), 3.27 (1 H, m overlapping with H-2' and H- 3', H-5'), 3.36 (1H, dd, , J=6.05 and 10.5 Hz, H-1), 3.45–3.52 (2H, m, H-6'), 3.61 (1 H, broad d, J~3Hz, H-4'), 3.87 (1 H, dd, J=5.1 and 10.5 Hz, H-1), 4.02 (1 H, d, J=7.3 Hz, H-1'), 4.29 (1 H, m, H-2), 5.1 (1 H, m, H-3), 7.81 (1 H, d, J=9.1 Hz, —NH—), 7.44, 7.58 and 7.91 (2H, 1H and 2H, 3m, —$C_6H_5$).

Anal. Calcd. for $C_{55}H_{99}NO_9$: C 71.93; H 10.86; N 1.53. Found: C 71.96; H 10.72; N 1.74.

I. (2S,3R)-3-Benzoyloxy-1-(4,6-O-benzylidene-β-D-galactopyranosyloxy)-2-tetracosanoylamino-octadecane

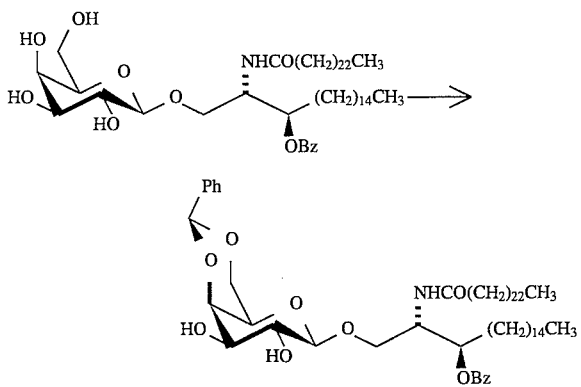

(2S,3R)-3-Benzoyloxy-1-(β-D-galactopyranosyloxy)-2-tetracosanoylaminooctadecane (0.460 g, 0.5 mmol) was treated by the general procedure as described in Example 1-C and gave after chromatography (chloroform-methanol 95:5) 0.500 g (99%) of the title material as a glassy solid.

$[\alpha]_D^{22}$: −13° (c=1.0, CHCl$_3$).

IR (KBr) $\upsilon_{max}$ (cm$^{-1}$): 1722 (C=O ester) and 1648 (C=O amide).

$^1$H NMR 400 MHz (DMSO-d$_6$+CDCl$_3$~5%) δ(ppm): 0.83 (6H, t, J=7 Hz, 2 x —CH$_3$), 1.1–1.7 (70H, m, —(CH$_2$)$_{14}$— and —(CH$_2$)$_{21}$—), 2.07 (2H, m, —NHCOCH$_2$—), 3.3–3.4 (2H, m, H-2' overlapping with —OH), 3.42 (1 H, br s, H- 5'), 3.46 (1 H, dd, J=3.3 and 9.7 Hz, H-3'), 3.56 (1 H, dd, J=4.23 and 10.5 Hz, H-1), 3.92 (1 H, dd, J=5.5 and 10.5 Hz, H-1), 3.95 (1 H, d, J$_{AB}$=11 Hz, H-6'), 3.97 (1 H, d, J$_{AB}$=11 Hz, H-6'), 4.04 (1 H, d, J=3.3 Hz, H-4'), 4.18 (1 H, d, J=7.3 Hz, H-1'), 4.32 (1 H, m, H-2), 5.13 (1H, m, H-3), 5.50 (1 H, s, —O—CH—O—), 7.31, 7.43, 7.56 and 7.95 (3H, 4H, 1H and 2H, 4m, 2 x —C$_6$H$_5$), 7.82 (1 H, d, J=9 Hz, —NH—).

Anal. Calcd. for C$_{62}$H$_{103}$NO$_9$.0.5 H$_2$O: C 73.40; H 10.23; N 1.38. Found: C 73.45; H 10.17; N 1.53.

J. (2S,3R)-3-Benzoyloxy-1-(2,3-di-O-benzoyl-4,6-O-benzylidene-β-D-galactopyranosyloxy)-2-tetracosanoylaminooctadecane

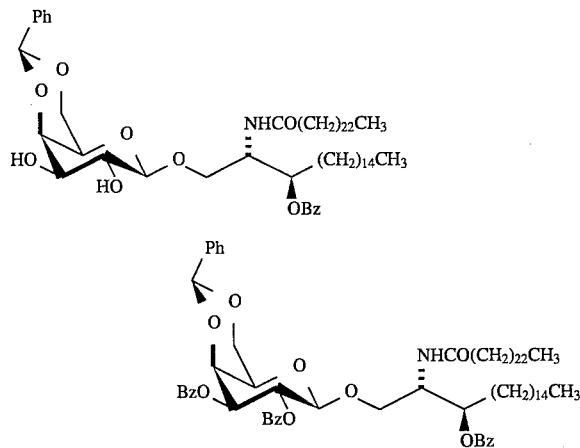

(2S,3R)-3-Benzoyloxy-1-(4,6-O-benzylidene-β-D-galactopyranosyloxy)- 2-tetracosanoylamino-octadecane (0.450 g, 0.45 mmol) was reacted by the general procedure as described in Example 1-D and gave 0.502 g (92%) of the title material as a glassy solid.

m.p. 95°–97° C. (CH$_2$Cl$_2$—MeOH); $[\alpha]_D^{22}$: +49° (c=1.0, CHCl$_3$).

IR (KBr) $\upsilon_{max}$ (cm$^{-1}$): 1726 and 1718 (C=O ester), 1650 (C=O amide).

$^1$H NMR 400 MHz (CDCl$_3$) δ(ppm): 0.89 (6H, t, J=7 Hz, 2 x —CH$_3$), 1.1–1.4 (68H, m, —(CH$_2$)$_{13}$— and —(CH$_2$)$_{21}$—), 1.70 (2H, m, —CH$_2$—), 1.85 (2H, m, —NHCOCH$_2$—), 3.68 (1 H, br s, H-5'), 3.80 (1 H, dd, J=4.5 and 10.4 Hz, H-1), 4.1 (2H, m, H-1 and H-6' overlapping), 4.28 (1 H, dd, J=0.9 and 12.0 Hz, H- 6'), 4.43 (1H, m, H-2), 4.58 (1H, d, J=3.7 Hz, H-4'), 4.74 (1H, d, J=7.9 Hz, H- 1'), 5.25 (1H, m, H-3), 5.38 (1H, dd, J=3.7 and 10.4 Hz, H-3'), 5.55 (1H, s, —O—CH—O—), 5.82 (1 H, dd, J=7.9 and 10.4 Hz, H-2'), 5.94 (1 H, d, J=8.7 Hz, —NH—), 7.38, 7.51 and 7.95 (11 H, 3H and 6H, 3m, 4 x —C$_6$H$_5$).

Anal. Calcd. for C$_{76}$H$_{111}$NO$_{11}$: C 75.15; H 9.21; N 1.15. Found: C 75.17; H 9.14; N 1.33.

K. (2S,3R)-3-Benzoyloxy-1-(2,3-di-O-benzoyl-β-D-galactopyranosyloxy)-2-tetracosanoylaminooctadecane

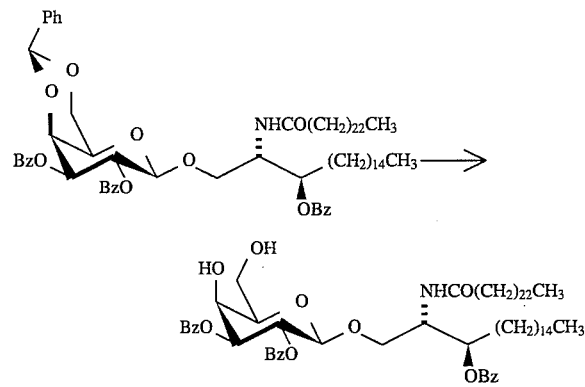

(2S,3R)-3-Benzoyloxy-1-(2,3-di-O-benzoyl-4,6-O-benzylidene-β-D-galactopyranosyloxy)- 2-tetracosanoylaminooctadecane (0.480 g, 0.395 mmol) was reacted by the general procedure as described in Example 1-F and gave 0.430 g (96%) of the title material as a white solid.

m.p. 144°–146° C. (dichloromethane-methanol).

$[\alpha]_D^{22}$: +68.5° (c=1.0, CHCl$_3$).

IR (KBr) $\upsilon_{max}$ (cm$^{-1}$): 1728 and 1710 (C=O ester), 1660 (C=O amide).

$^1$H NMR 400 MHz (DMSO-d$_6$+5% CDCl$_3$) δ(ppm): 0.84 and 0.842 (2x 3H, 2t, J=6.0 and J=6.3 Hz, 2 x —CH$_3$), 1.0–1.6 (70H, m, —(CH$_2$)$_{14}$— and —(CH$_2$)$_{21}$—), 1.85 (2H, m, —NHCOCH$_2$—), 3.54 (1H, dd, J$_{AB}$=10.7 Hz, J$_{AX}$=6.1 Hz, H-6'), 3.60 (1 H, dd, J$_{AB}$=10.7 Hz and J$_{BX}$=6.6 Hz, H-6'), 3.69 (1 H, dd, J=6.7 and 10.0 Hz, H-1), 3.72 (1 H, br t, H-5'), 3.81 (1 H, dd, J=6.5 and 10.0 Hz, H-1), 4.17 (1H, d, J=3.1 Hz, H-4'), 4.30 (1H, m, H-2), 4.83 (1H, d, J=7.95 Hz, H-1'), 5.01 (1 H, m, H-3), 5.18 (1 H, dd, J=3.1 and 10.3 Hz, H-3'), 5.53 (1 H, dd, J=7.95 and 10.3 Hz, H-2'), 7.3–7.65 and 7.85–7.93 (10H and 6H, 2m, 3 x —C$_6$H$_5$ and —NH—).

Anal. Calcd. for C$_{69}$H$_{107}$NO$_{11}$: C 73.56; H 9.57; N 1.24. Found: C 73.56; H 9.46; N 1.41.

L.
(2S,3R)-3-Benzoyloxy-1-[2,3-di-O-benzoyl-4,6-di-O-(sodium oxysulfonyl)-β-D-galactopyranosyl-oxy]-2-tetracosanoylaminooctadecane

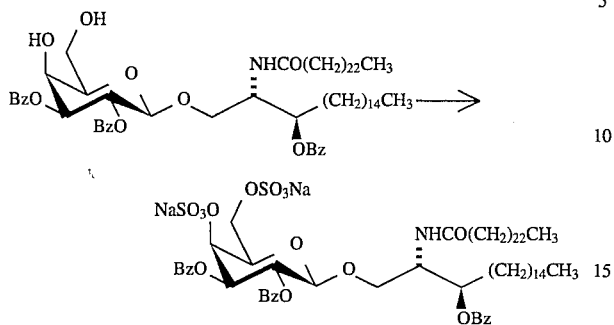

(2S,3R)-3-Benzoyloxy-1-(2,3-di-O-benzoyl-β-D-galactopyranosyloxy)-2tetracosanoylaminooctadecane (0.382 g, 0.339 mmol) was reacted by the general procedure as described in Example 1-G and gave after chromatography and lyophilization from dioxane 0.417 g (92%) of the title material as a white amorphous powder.

$[\alpha]_D^{22}$: +26° (c=1.0, CHCl$_3$-MeOH 9:1).

IR (KBr) $\upsilon_{max}$ (cm$^{-1}$): 1725 (C=O ester) and 1640 (C—O amide).

$^1$H NMR 400 MHz (DMSO-d$_6$) δ(ppm): 0.83 (6H, t, J=7 Hz, 2 x —CH$_3$), 0.9–1.5 (70H, m, —(CH$_2$)$_{14}$— and —(CH$_2$)$_{21}$—), 1.89 (2H, m, —NHCOC$\underline{H}_2$—), 3.66 (1 H, dd, J=7.52 and 9.5 Hz, H-1), 3.83 (1 H, dd, J=6.5 and 9.5 Hz, H-1 ), 3.89 (1 H, dd, J=7.2 and 11.0 Hz, H-5'), 4.12 (2H, m, H-6'), 4.23 (1H, m, H-2), 4.69 (1 H, d, J=3.1 Hz, H-4'), 4.87 (1 H, d, J=7.6 Hz, H-1'), 4.98 (1 H, m, H-3), 5.30 (1 H, dd, J=3.1 and J=10.3 Hz, H-3'), 5.37 (1 H, dd, J=7.6 and J=10.3 Hz, H- 2'), 7.3–7.6 and 7.8–7.9 (9H and 7H, 2m, 3 x —C$_6$H$_5$ and —NH—).

Anal. Calcd. for C$_{69}$H$_{105}$NO$_{17}$S$_2$Na$_2$.2 H$_2$O: C 60.64; H 8.05; N 1.02. Found: C 60.52; H 7.76; N 1.12.

EXAMPLE 20

(2S,3R)-3-Hydroxy-[4,6-di-O-(sodium oxysulfonyl)-β-D-galactopyranosyloxy]-2-tetracosanoylaminoctadecane

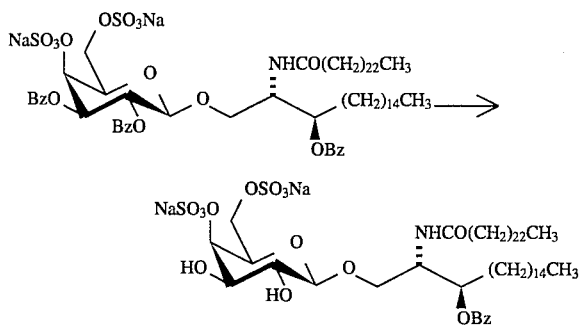

(2S,3R)-3-Benzoyloxy-1-[2,3-di-O-benzoyl-4,6-di-O-(sodium oxysulfonyl)-β-D-galactopyranosyl-oxy]-2-tetracosanoylamino-octadecane (0.277 g, 0.208 g) was reacted as described in Example 2-A and gave 0.184 g (86%) of the title material as a white solid after crystallization from methanol.

m.p. dec. >200° C.

IR (KBr) $\upsilon_{max}$ (cm$^{-1}$): 1650 (C=O amide).

$^1$H NMR 400 MHz (DMSO-d$_6$) δ(ppm): 4.66 (1H, d, J=6.3 Hz, —OH), 4.92 (1 H, d, J=3.7 Hz, —OH) and 4.99 (1 H, d, J=6.9 Hz, —OH); exchanged D$_2$O d (ppm): 0.84 (6H, t, J=6.7 Hz, 2 x —CH$_3$), 1.1–1.6 (70H, m, —(CH$_2$)$_{14}$— and —(CH$_2$)$_{21}$—), 2.06 (2H, m, —NHCOC$\underline{H}_2$—) 3.2 (1H, dd, J=7.6 and 9.6 Hz, H-2'), 3.34–3.42 (3H, m, H-3, H-3' and H-5'), 3.68–3.75 (3H, m, H-1, H-2 and H-6' overlapping), 3.89 (1H, br d, J=9.8 Hz, H-6'), 3.99 (1H, dd, J=5.3 and J=10.0 Hz, H-1), 4.03 (1 H, d, J=7.6 Hz, H-1'), 4.30 (1 H, d, J=4.3 Hz, H-4'), 7.63 (1 H, d, J=9.3 Hz, —NH—).

Anal. Calcd. for C$_{48}$H$_{93}$NO$_{14}$S$_2$Na$_2$.H$_2$O: C 55.63; H 9.24; N 1.35. Found: C 55.76; H 9.04; N 1.44.

EXAMPLE 21

(2S,3R,4E)-2-Hexadecanoylamino-3-benzoyloxy-1-[2,6-di-O-(sodium oxysulfonyl)-β-D-galactopyranosyloxy]-4-octadecene

A.
(2S,3R,4E)-2-Hexadecanoylamino-3-benzoyloxy-1-(β-D-galactopyranosyloxy)- 4-octadecene

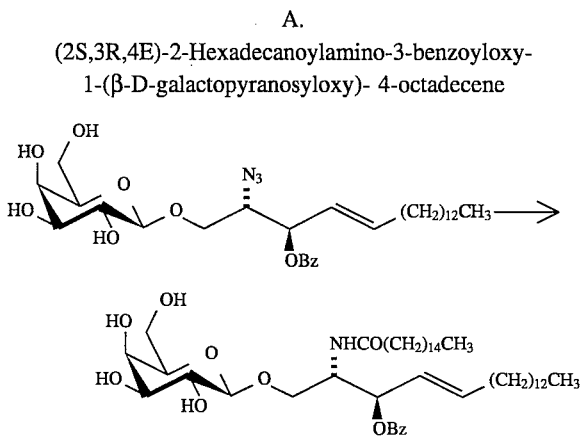

(2S,3R,4E)-2-Azido-3-benzoyloxy-1-(β-D-galactopyranosyloxy)-4-octadecene prepared in Example 1-B (250 mg, 0.42 mmol) was reacted by the general procedure as described in Example 13-A except that palmitoyl chloride was used instead of hexanoyl chloride and afforded the title compound (260 mg, 77%) as a white solid.

IR (CH$_2$Cl$_2$) $\upsilon_{max}$ (cm$^{-1}$): 3700–3100 (O—H and N—H), 3050, 2930, 2860 (C—H), 1720 (C=O ester), 1670 (C=O amide).

$^1$H NMR 400 MHz (CDCl$_3$) δ(ppm): 0.87–0.90 (6H, ~t, 2 x —CH$_3$), 1.24–1.63 (48H, br m, —(CH$_2$)$_{13}$— and —(CH$_2$)$_{11}$—), 2.04 (2H, m, =CH—C$\underline{H}_2$—), 2.17–2.22 (2H, m, —NHCOC$\underline{H}_2$—), 3.43 (1 H, br t, H-5'), 3.53 (1 H, dd, J=9.5 and 3.3 Hz, H-3'), 3.66 (1 H, dd, J=9.5 and 7.7 Hz, H-2'), 3.71 (1 H, dd, J=12.3 and 3.9 Hz, H-1), 3.78–3.85 (2H, m, H-6'), 3.99–4.03 (2H, m, H-4' and H-1), 4.29 (1H, d, J=7.7 Hz, H-1'), 4.57–4.60 (1H, m, H-2), 5.50 (1H, dd, J=15.3 and 7.4 Hz, H-4), 5.65 (1 H, t, J=7.4 Hz, H-3), 5.92 (1 H, dt, J=15.3 and 6.9 Hz, H-5), 6.16 (1H, d, J=6.16 Hz, —NH—), 7.45–8.04 (5H, 3m, —C$_6$H$_5$).

B.
(2S,3R,4E)-2-Hexadecanoylamino-3-benzoyloxy-1-(3,4-O-isopropylidene-β-D-galactopyranosyloxy)-4-octadecene

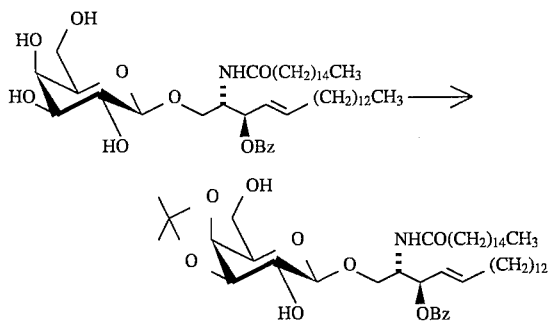

(2S,3R,4E)-2-Hexadecanoylamino-3-benzoyloxy-1-(β-D-galactopyranosyloxy)-4-octadecene (950 mg, 1.18 mmol) was reacted by the general procedure as described in Example 5-C and afforded the title compound (790 mg, 79%) as a white solid.

$^1$H NMR 200 MHz (CDCl$_3$) δ(ppm): 0.88 (6H, t, J=6.4 Hz, 2 x —CH$_3$), 1.24–1.60 (48H, br m, —(CH$_2$)$_{13}$— and —(CH$_2$)$_{11}$—), 1.34 and 1.50 (2 x 3H, 2s, —C(CH$_3$)$_2$—), 2.05 (2H, m, =CH—CH$_2$—), 2.18 (2H, m, —NHCOCH$_2$—), 3.49 (1 H, dd, J=8.2 and 6.6 Hz, H-2'), 3.74–4.14 (7H, m, H-1, H-6', H-3', H-4' and H-5'), 4.20 (1 H, d, J=8.2 Hz, H-1'), 4.54 (1H, m, H-2), 5.50 (1H, dd, J=15.0 and 7.3 Hz, H-4), 5.61 (1 H, t, J=7.3 Hz, H-3), 5.89 (1 H, dt, J=15.0 and 6.7 Hz, H-5), 5.97 (1 H, d, J=9.1 Hz, —NH—), 7.41–8.05 (5H, 3m, —C$_6$H$_5$).

C.
(2S,3R,4E)-2-Hexadecanoylamino-3-benzoyloxy-1-[2,6-di-O-(sodium oxysulfonyl)-β-D-galactopyranosyloxy]-4-octadecene

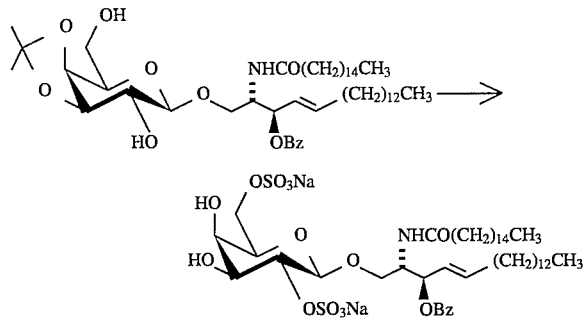

Sulfur trioxide trimethylamine complex (530 mg, 3.8 mmol) was added to a stirred solution of (2S,3R,4E)-2-hexadecanoylamino-3-benzoyloxy-1-( 3,4-O-isopropylidene-β-D-galactopyranosyloxy)-4-octadecene (160 mg, 0.19 mmol) in dry dimethylformamide (10 mL) at 22° C. and under argon. The resulting mixture was heated at 80°–85° C. for 45 minutes, then cooled down to 5° C. and treated with a 1M solution of sodium bicarbonate (≈0.5 mL) for ≈20 minutes. The mixture was evaporated and the residue was dissolved in a mixture dichloromethane/methanol (1:1) and filtered. The filtrate was evaporated and afforded a residue which was dried under vacuum and dissolved in trifluoroacetic acid (90%, 5 mL). After stirring for about 5 minutes at 22° C., this mixture was evaporated and the residue was co-evaporated with toluene, dissolved in a mixture dichloromethane/methanol (4:1) and neutralized with sodium bicarbonate. The excess of sodium bicarbonate was filtered and the filtrate was purified on silica gel plates (chloroform/methanol 7:3) to give the title compound (115 mg, 60%) as a white solid.

IR (Nujol) υ$_{max}$ (cm$^{-1}$): 3700–3100 (O—H and N—H), 2930, 2860 (C—H), 1715 (C=O ester), 1650 (C=O amide), 1270, 1010 (S=O).

$^1$H NMR 400 MHz (DMSO-d$_6$) δ(ppm): 0.85 (6H, t, J=6.8 Hz, 2 x —CH$_3$), 1.21–1.44 (48H, br m, —(CH$_2$)$_{13}$— and —(CH$_2$)$_{11}$—), 1.97 (2H, m, =CH—CH$_2$—), 2.02–2.21 (2H, m, —NHCOCH$_2$—), 3.45–3.51 (2H, m, H-1 and H-3'), 3.58 (1H, br t, J=6.1 Hz, H-5'), 3.62 (1H, t, J=3.9 Hz, H-4'), 3.74 (1H, dd, J=10.6 and 6.3 Hz, H-6'), 3.82 (1H, dd, J=10.6 and 5.7 Hz, H-6'), 3.97 (1H, dd, J=9.8 and 4.5Hz, H-1), 4.15 (1H, dd, J=9.4 and 7.8 Hz, H-2'), 4.24–4.28 (1H, m, H-2), 4.27 (1H, d, J=7.6 Hz, H-1'), 4.69 (1H, d, J=3.9 Hz, —OH), 5.09 (1H, d, J=1.4 Hz, —OH), 5.39 (1H, t, J=7.6 Hz, H-3), 5.45 (1H, dd, J=15.0 and 7.6 Hz, H-4), 5.76 (1H, dt, J=15.0 and 6.8 Hz, H-5), 7.73 (1H, d, J=8.9 Hz, —NH—), 7.48–7.98 (5H, 3m, —C$_6$H$_5$).

EXAMPLE 22

(2S,3R,4E)-2-Hexadecanoylamino-3-hydroxy-1-[2,6-di-O-(sodium oxysulfonyl)-β-D-galactopyranosyloxy]-4-octadecene

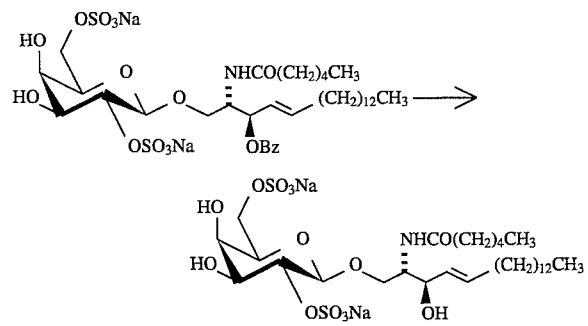

(2S,3R,4E)-2-Hexadecanoylamino-3-benzoyloxy-1-[2,6-di-O-(sodium oxysulfonyl)-β-D-galactopyranosyloxy]-4-octadecene (243 mg, 0.24 mmol) was reacted by the general procedure as described in Example 6-A and afforded the title compound (170 mg, 78%) as a pale beige solid.

IR (Nujol) υ$_{max}$ (cm$^{-1}$): 3700–3100 (O—H and N—H), 2920, 2860 (C—H), 1650 (C=O amide).

$^1$H NMR 400 MHz (DMSO-d$_6$) δ(ppm): 0.85 (6H, t, J=6.8 Hz, 2 x —CH$_3$), 1.23–1.43 (48H, br m, —(CH$_2$)$_{13}$— and —(CH$_2$)$_{11}$—), 1.89 (2H, m, =CH—CH$_2$—), 2.00–2.16 (2H, m, —NHCOCH$_2$—), 3.27 (1H, dd, J=9.3 and 3.3 Hz, H-1), 3.47 (1H, dd, J=9.6 and 3.1 Hz, H-3'), 3.58 (1H, br t, H-5'), 3.63 (1H, d, J=3.1 Hz H-4'), 3.70 (1H, m, H-3), 3.76–3.86 (1H, m overlapping H-6', H-2), 3.79 (1H, dd, J=10.6 and 6.5 Hz, H-6'), 3.84 (1H, dd, J=10.6 and 5.6 Hz, H-6'), 4.09 (1H, dd, 9.6 and 7.7 Hz, H-2'), 4.15 (1H, dd, J=9.3 and 2.7 Hz, H-1), 4.24 (1H, d, J=7.7 Hz, H-1'), 4.68 (1H, br s, —OH), 4.87 (1H, d, J=3.8 Hz, —OH), 4.95 (1H, br s, —OH), 5.30 (1H, dd, J=15.4 and 7.2 Hz, H-4), 5.48 (1H, dt, J=15.4 and 6.6 Hz, H-5), 7.41 (1H, d, J=9.2 Hz, —NH—).

EXAMPLE 23

(2S,3R)-3-Benzoyloxy-1-[2,6-di-O-(sodium oxysulfonyl-β-D-galactopyranosyloxy]-2-tetracosanoylaminooctadecane

A. (2S,3R)-3-Benzoyloxy-1-(3,4-O-isopropylidene-β-D-galactopyranosyloxy)-2-tetracosanoylaminooctadecane

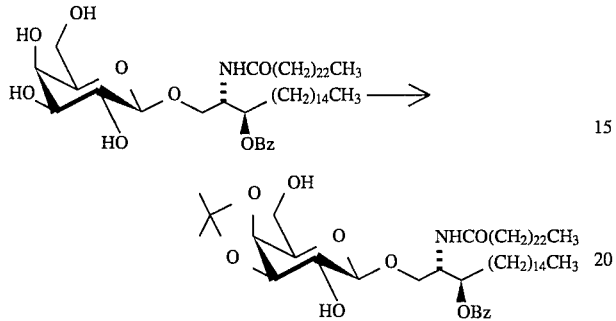

(2S,3R)-3-Benzoyloxy-2-tetracosanoylamino- 1-(β-D-galactopyranosyloxy)-octadecane prepared in Example 19-H (0.667 g, 0.726 mmol) was reacted by the general procedure as described in Example 5-C and gave after chromatography 0.630 g (90%) of the title material as a glassy solid.

$[\alpha]_D^{22}$: +13° (c=0.9, CHCl$_3$/MeOH 8:2).

IR (KBr) $\upsilon_{max}$ (cm$^{-1}$): 1720 (C=O of ester) and 1650 (C=O of amide).

$^1$H NMR 200 MHz (CDCl$_3$) δ(ppm): 0.88 (6H, ~t, 2 x —CH$_3$ overlapping), 1.1–1.9 (70H, broad, —(CH$_2$)$_{14}$— and —(CH$_2$)$_{21}$—), 1.33 and 1.47 (2 x 3H, 2s, —C(CH$_3$)$_2$), 2.20 (2H, t, J=7.5 Hz, —NHCOCH$_2$—), 3.42 (1H, m, H-5'), 3.65–3.95 (5H, broad, H-1,H-4' and H-6'), 4.0–4.1 (2H, m, H-2' and H-3' overlapping), 4.18 (1H, d, J=8.16 Hz, H-1'), 4.5 (1H, m, H-2), 5.2 (1H, m, H-3), 6.35 (1H, d, J=9 Hz, —NH—), 7.47, 7.58 and 8.05 (2H, 1H and 2H, 3m, —C$_6$H$_5$).

Anal. Calcd. for C$_{58}$H$_{103}$NO$_9$: C 72.68;H 10.83; N 1.46. Found: C 72.68;H 10.73; N 1.69.

B. (2S,3R)-3-Benzoyloxy-1-[3,4-O-isopropylidene-2,6-di-O-(sodium oxysulfonyl)-β-D-galactopyranosyloxy]-2-tetracosanoylaminooctadecane

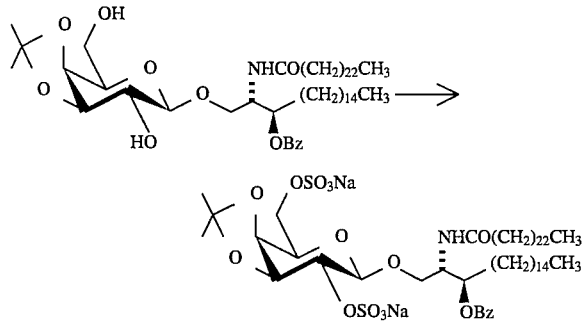

(2S,3R)-3-Benzoyloxy-1-(3,4-O-isopropylidene-β-D-galactopyranosyloxy)- 2-tetracosanoylaminooctadecane (0.328 g, 0.342 mmol) was reacted by the general procedure as described in Example 5-D and gave after chromatography 0.344 g (86%) of the title material as a glassy solid.

$[\alpha]_D^{22}$:–12° (c=1.0, CHCl$_3$).

IR (film) $\upsilon_{max}$ (cm$^{-1}$): 1725 and 1705 (C=O of ester) and 1640 (C=O of amide).

$^1$H NMR 400 MHz (DMSO-d$_6$) δ(ppm): 0.84 (6H, t, J=6.8 Hz, 2 x —CH$_3$), 1.1–1.8 (70H, broad m, —(CH$_2$)$_{14}$— and —(CH$_2$)$_{21}$—), 1.24 and 1.36 (2 x 3H, 2s, —C(CH$_3$)$_2$), 2.02 and 2.2 (2 x 1H, 2m, —NHCOCH$_2$—), 3.39 (1H, dd, J=4.2 and J=10.1 Hz, H-1), 3.78 (2H, m, H-6'), 3.86 (1H, m, H-5'), 3.93 (1H, dd, J=3.3 and J=10.1 Hz, H-1), 4.11 (2H, m, H-3' and H-4' overlapping), 4.24 (1H, dd, J=5.6 and 6.0 Hz, H-2'), 4.25 (1H, m, overlapping with H-2', H-2), 4.46 (1H, d, J=5.6 Hz, H-1'), 5.07 (1H, m, H- 3), 7.49, 7.62 and 7.95 (2H, 1H and 3H, 3m, —C$_6$H$_5$), 8.14 (1H, d, J=9.1 Hz, —NH—).

C. (2S,3R)-3-Benzoyloxy-1-[2,6-di-O-(sodium oxysulfonyl)-β-D-galactopyranosyloxy]-2-tetracosanoylaminooctadecane

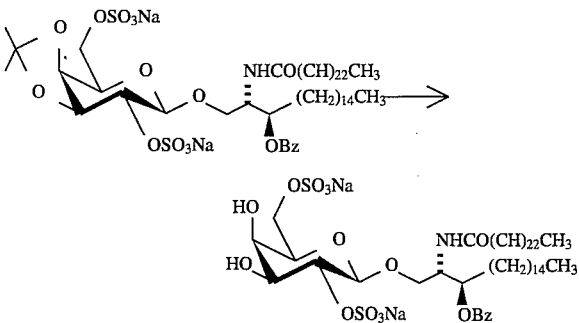

A solution of (2S,3R)-3-benzoyloxy-1-[3,4-O-isopropylidene-2,6-di-O-(sodium oxysulfonyl)-β-D-galactopyranosyloxy]-2-tetracosanoylaminooctadecane (0.250 g, 0.215 mmol) in a mixture of tetrahydrofuran (20 mL) and 80% aqueous acetic acid (10 mL) was stirred at 22° C. for 9 hours. Evaporation of the solvent under vacuum and chromatography of the residue on silica gel (2×8 cm, elution CHCl$_3$/MeOH; 7:3) gave 0.210 g (87%) of the title material as a glassy solid.

$[\alpha]_D^{22}$: +1° (c=1.0, CHCl$_3$/MeOH 9:1).

IR (KBr) $\upsilon_{max}$ (cm$^{-1}$): 1720 (C=O of ester) and 1635 (C=O of amide).

$^1$H NMR 400 MHz δ(ppm): 0.84 (6H, t, J=8 Hz, 2 x —CH$_3$), 1.1–1.7 (70H, m, —(CH$_2$)$_{14}$— and —(CH$_2$)$_{21}$—), 2.03 and 2.26 (2 x 1H, 2m, —NHCOCH$_2$—), 3.49 (2H, m, H-1 and H-3' overlapping), 3.59 (1H, broad t, J=6 Hz, H-5'), 3.63 (1H, m, H-4'), 3.77 (1H, dd, J$_{AB}$=10.57 Hz and J$_{AX}$=6.35 Hz, H-6'), 3.83 (1H, dd, J$_{AB}$=10.57 Hz and J$_{BX}$=5.79 Hz, H-6'), 3.94 (1H, dd, J=4.25 and 9.81 Hz, H-1), 4.15 (1H, dd, J=7.7 and 9.36 Hz, H-2'), 4.27 (1H, m overlapping with H-1', H-2), 4.28 (d, J=7.7 Hz, H-1'), 4.70 (1H, d, J=4.2 Hz, —OH exchanged with D$_2$O), 5.06 (2H, m, —OH and H-3 overlapping), 7.49, 7.62 and 7.94 (2H, 1H and 2H, 3m, —C$_6$H$_5$) and 7.77 (1H, d, J=9 Hz, —NH—).

EXAMPLE 24

(2S,3R)-3-Hydroxy-1-[2,6-di-O-(sodium oxysulfonyl)-β-D-galactopyranosyloxy]-2-tetracosanoylaminooctadecane

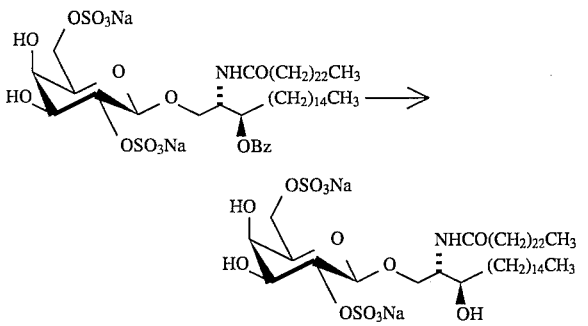

(2S,3R)-3-Benzoyloxy-1-[2,6-di-O-(sodium oxysulfonyl)-β-D-galactopyranosyloxy]- 2-tetracosanoylaminooctadecane (0.111 g, 0.098 mmol) was reacted by the general procedure as described in Example 6-A and gave 0.066 g (67%) of title material as a white amorphous powder after trituration with methanol.

[α]$_D^{22}$: +4° (c=0.5, CHCl$_3$/MeOH/H$_2$O; 5:4:1).

IR (KBr) $υ_{max}$ (cm$^{-1}$): 1655 (C=O of amide).

$^1$H NMR 400 MHz (DMSO-d$_6$) δ(ppm): 4.59 (1H, d, J=6.6 Hz, —OH), 4.66 (1H, d, J=4.1 Hz, —OH) and 4.98 (1H, broad s, —OH); exchanged D$_2$O δ(ppm): 0.84 (6H, d, J=6.6 Hz, 2 x —CH$_3$), 1.1–1.5 (70H, m, —(CH$_2$)$_{14}$— and —(CH$_2$)$_{21}$—), 2.0 and 2.26 (2 x 1H, 2m, —NHCOCH$_2$—), 3.24 (1H, dd, J=2.98 and 9.06 Hz, H-1), 3.36 (1H, m, H-3), 3.47 (1H, dd, J=3.2 and 9.58 Hz, H-3'), 3.58 (1H, broad t, H-5'), 3.62 (1H, broad d, J=3.2 Hz, H- 4'), 3.67 (1H, m, H-2), 3.80 (1H, dd, J$_{AB}$=10.6 Hz, J$_{AX}$=5.53 Hz, H-6') 3.84 (1H, dd, J$_{AB}$=10.6 Hz, J$_{BX}$=6.53 Hz, H-6'), 4.08 (1H, dd, J=7.7 and 9.58 Hz, H-2'), 4.17 (1H, dd, J=2.38 and 9.06 Hz, H-1), 4.24 (1H, d, J=7.7 Hz, H-1') and 7.55 (1H, d, J=9.3 Hz, —NH—).

EXAMPLE 25

(2S,3R,4E)-3-Benzoyloxy-2-hexadecanoylamino-1-[2,6-di-O-(sodium oxysulfonyl)-β-D-galactopyranosyloxy]-4-undecene

A.
(2S,3R,4E)-1,3-O-Benzylidene-4-undecene-1,2,3-triol

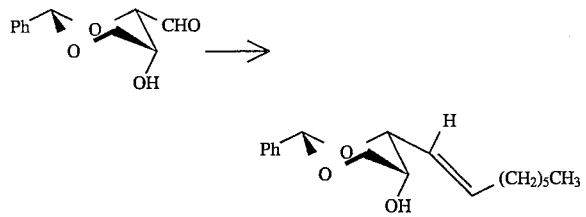

Reaction of 2,4-O-benzylidene-D-threose [as described by P. Zimmermann and R. R. Schmidt. *Liebigs Ann. Chem.* 1988, 663–667] (23.5 g, 0.112 mol) with n-heptyltriphenylphosphonium bromide [as described by C. F. Hauser, T. W. Brooks, M. L. Miles, M. A. Raymond and G. B. Butler, *J. Org. Chem.*, 28, 372 (1963).] (64 g, 0.145 mol) and phenyllithium (0.393 mol) using the methodology described by P. Zimmermann and R. R. Schmidt gave 15.14 g (46%) of the title material as a white solid after chromatography.

m.p. 50°–52° C.; [α]$_D^{22}$: −2° (c=0.5, CHCl$_3$).

IR (KBr) $υ_{max}$ (cm$^{-1}$): 3380 (OH).

$^1$H NMR 400 MHz (CDCl$_3$) δ(ppm): 0.89 (3H, t, J=6.9 Hz, —CH$_3$), 1.2–1.45 (8H, m, —(CH$_2$)$_4$—), 2.09 (2H, m, =CHCH$_2$—), 2.64 (1H, d, J=10.4 Hz, —OH), 3.54 (1H, m, H-2), 4.09 (1H, dd, J=1.3 and 11.8 Hz, H-1), 4.25 (1H, dd, J=1.9 and 11.8 Hz, H-1), 4.42 (1H, br d, J=6 Hz, H-3), 5.63 (1H, s, —O—CH—O—), 5.67 (1H, m, J=15.6 Hz, H-4), 5.88 (1H, m, J=15.6 Hz, H-5), 7.38 and 7.53 (3H and 2H, 2m, —C$_6$H$_5$).

Anal. Calcd. for C$_{18}$H$_{26}$O$_3$: C 74.45; H 9.02. Found: C 74.47; H 8.87.

B.
(2S,3R,4E)-2-Azido-1,3-O-Benzylidene-4-undecene-1,3-diol

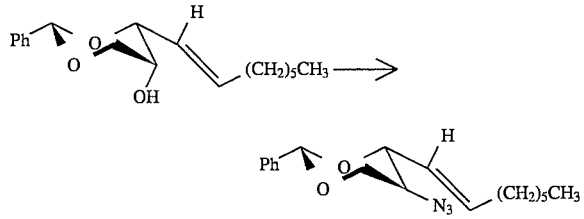

(2S,3R,4E)-1,3-O-Benzylidene-4-undecene-1,2,3-triol (9.20 g, 31.7 mmol) was reacted by the general procedure as described in Example 19-B and gave 5.32 g (53%) of the title material as an oil.

[α]$_D^{22}$: −17° (c=1.0, CHCl$_3$).

IR (NaCl, film) $υ_{max}$ (cm$^{-1}$): 2105 (N$_3$).

$^1$H NMR 200 MHz (CDCl$_3$) δ(ppm): 0.89 (3H, t, J=6.5 Hz, —CH$_3$), 1.2–1.5 (8H, m, —(CH$_2$)$_4$—), 2.11 (2H, m, =CHCH$_2$—) 3.46 (1H, ddd, J=4.7 Hz, 9.0 and 10.7 Hz, H-2), 3.62 (1H, dd, J=10.7 and 10.7 Hz, H-1), 4.05 (1H, dd, J=7.4 and 9.0 Hz, H-3), 4.34 (1H, dd, J=4.7 and 10.7 Hz, H-1), 5.49 (1H, s, —O—CH—O—), 5.59 (1H, ddt, J=7.4, 15.5 and 1.3 Hz, H-4), 6.00 (1H, dt, J=6.8 and 15.5 Hz, H-5), 7.3–7.5 (5H, m, —C$_6$H$_5$).

Anal. Calcd. for C$_{18}$H$_{25}$N$_3$O$_2$: C 68.54; H 7.99; N 13.32. Found: C 68.59; H 7.49; N 13.41.

C. (2S,3R,4E)-2-Azido-4-undecene-1,3-diol

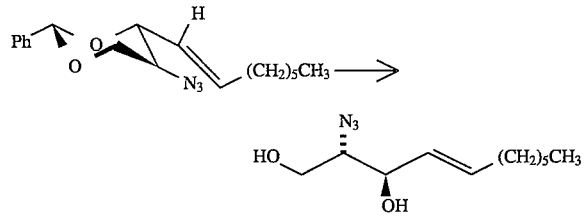

(2S,3R,4E)-2-Azido-1,3-O-benzylidene-4-undecene-1,3-diol (5.32 g, 11.9 mmol) was reacted by the general procedure as described in Example 19-C and gave 3.48 g (91%) of the title material as a white solid.

m.p. 29°–30° C. (hexane); [α]$_D^{22}$: −51° (c=1.0, CHCl$_3$).

IR (NaCl, film) $υ_{max}$ (cm$^{-1}$): 3350 (OH), 2100 (N$_3$).

$^1$H NMR 200 MHz (CDCl$_3$) δ(ppm): 0.88 (3H, t, J=6.5Hz, —CH$_3$), 1.2–1.7 (8H, m, —(CH$_2$)$_4$—), 2.1 (4H, m, =CHCH$_2$— and 2 x —OH), 3.51 (1H, dt, J=5.3 and 5.3 Hz, H-2), 3.78 (2H, br d, CH$_2$-1), 4.25 (1H, br t, H-3), 5.53 (1H, ddt, J=15.4, 7.2 and 1.3 Hz, H-4), 5.82 (1H, dt, J=15.4 and 6.6 Hz, H-5).

Anal. Calcd. for: $C_{11}H_{21}N_3O_2$: C 58.12; H 9.31; N 18.49. Found: C 58.21; H 9.22; N 18.27.

D. (2S,3R,4E)-2-Azido-1-O-t-butyldimethylsilyl-4-undecene-1,3-diol

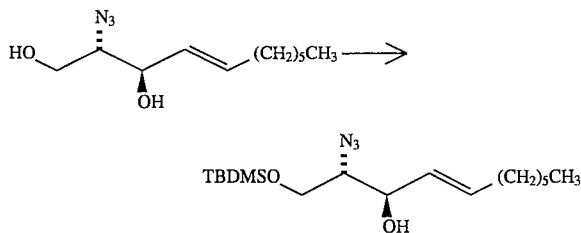

(2S,3R,4E)-2-Azido-4-undecene-1,3-diol (2.74 g, 12.06 mmol) was reacted by the general procedure as described in Example 19-D and gave 3.96 g (96%) of the title material as an oil.

$[\alpha]_D^{22}$: −3.5° (c=1.0, CHCl$_3$).

IR (NaCl, film) $\upsilon_{max}$ (cm$^{-1}$): 3440 (OH), 2100 (N$_3$).

$^1$H NMR 200 MHz (CDCl$_3$) δ(ppm): 0.09 (6H, s, —SiCH$_3$), 0.9 (12H, br s, —Si—t—Bu and —CH$_3$), 1.2–1.5 (8H, m, —(CH$_2$)$_4$—), 2.06 (2H, m, =CHC$\underline{H}_2$—), 2.32 (1H, d, J=5.0 Hz, —OH), 3.42 (1H, m, H-2), 3.80 (2H, m, CH$_2$-1), 4.21 (1H, m H-3), 5.49 (1H, ddt, J=15.4, 7.0 and 1.3 Hz, H-4), 5.78 (1H, m, H-5).

Anal. Calcd. for $C_{17}H_{35}N_3O_2Si$: C 59.78, H 10.33; N 12.30. Found: C 59.71; H 10.24; N 12.16.

E. (2S,3R,4E)-2-Azido-3-benzoyloxy-1-O-t-butyl-dimethylsilyl- 4-undecene-1-ol

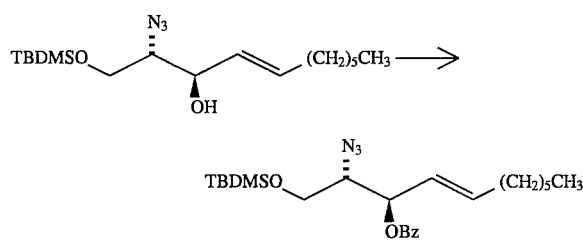

(2S,3R,4E)-2-Azido-1-O-t-butyldimethylsilyl-4-undecene-1,3 diol (3.96 g, 11.6 mmol) was reacted by the general procedure as described in Example 19-E and gave 5.2 g (100%) of the crude title material which was used as such in the next step.

IR (NaCl, film) $\upsilon_{max}$ (cm$^{-1}$): 2100 (N$_3$), 1725 (C=O ester).

$^1$H NMR 200 MHz (CDCl$_2$) δ(ppm): 0.07 (6H, s, —SiCH$_3$), 0.86 (3H, t, J=6.7 Hz, —CH$_3$), 0.91 (9H, s, —Si—t—Bu), 1.2–1.5 (8H, m, —(CH$_2$)$_4$—), 2.08 (2H, m, =CHC$\underline{H}_2$—), 3.6–3.9 (3H, m, CH$_2$-1 and H-2), 5.5–5.7 (2H, m, H-3 and H-4), 5.92 (1H, dt, J=6.7 and 14.4 Hz, H-5), 7.45, 7.56 and 8.06 (2H, 1H and 2H, 3 m, —C$_6$H$_5$).

F. (2S,3R,4E)-2-Azido-3-benzoyloxy-4-undecene-1-ol

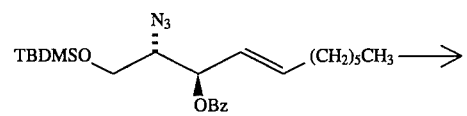

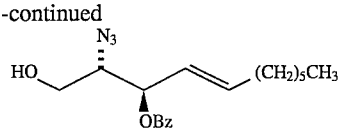

(2S,3R,4E)-2-azido-3-benzoyloxy-1-O-t-butyldimethylsilyl-4-undecene-1-ol (5.20 g, 11.6 mol) was treated by the general procedure as described in Example 19-E and gave 3.26 g (85%) of the title material as an oil.

$[\alpha]_D^{22}$: −65° (c=1.0, CHCl$_3$).

IR (NaCl, film) $\upsilon_{max}$ (cm$^{-1}$): 2105 (N$_3$), 1720 (C=O of ester).

$^1$H NMR 400 MHz (CDCl$_3$) δ(ppm): 0.87 (3H, t, J=6.8 Hz, —CH$_3$), 1.2–1.4 (8H, m, —(CH$_2$)$_4$—), 2.09 (2H, m, =CHC$\underline{H}_2$—), 3.63 (1H, dd, J=11.7 and 7.1 Hz, H-1), 3.76 (1H, dd, J=11.7 and 4.0 Hz, H-1), 3.81 (1H, m, H-2), 5.58–5.65 (2H, m, H-3 and H-4), 5.95 (1H, m, H-5), 7.44, 7.59 and 8.06 (2H, 1H and 2H, 3 m, —C$_6$H$_5$).

Anal. Calcd. for $C_{18}H_{25}N_3O_3 \cdot 0.5\ H_2O$: C 63.51; H 7.70; N 12.34. Found: C 63.45; H 7.45; N 12.29.

G. (2S,3R,4E)-2-Azido-3-benzoyloxy-1-(2,3,4,6-tetra-O-acetyl-α-D-galactopyranosyloxy)- 4-undecene and (2S,3R,4E)-2-azido-3-benzoyloxy-1-(2,3,4,6,tetra-O-acetyl-β-D-galactopyranosyloxy)-4-undecene

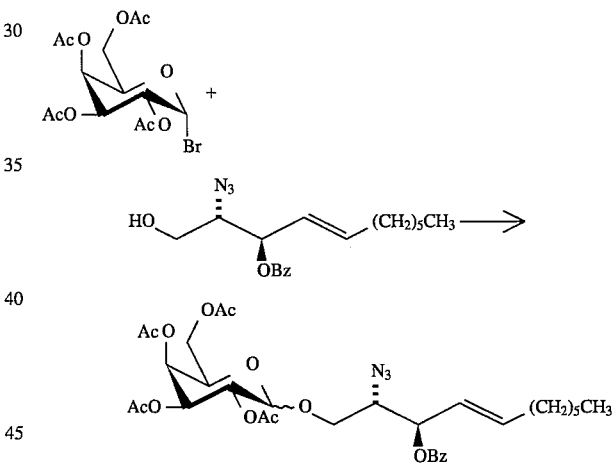

(2S,3R,4E)-2-Azido-3-benzoyloxy-4-undecene-1-ol (4.17 g, 12.58 mmol) and 2,3,4,6-tetra-O-acetyl-α-D-galactopyranosyl bromide [as described by P. Zimmermann and R. R. Schmidt. *Liebigs Ann. Chem.* 1988, 663–667] (8.2 g, 20.0 mmol) were reacted by the general procedure as described in Example 1-A and gave 1.11 g (13%) of the α-anomer and 5.72 g (68%) of the β-anomer.

α-anomer: Needles, m.p. 67°–68° C. (hexane).

$[\alpha]_D^{22}$: +70° (c=1.0, CHCl$_3$).

IR (KBr) $\upsilon_{max}$ (cm$^{-1}$): 2100 (N$_3$), 1752, 1745 and 1722 (C=O ester).

$^1$H NMR 400 MHz (CDCl$_3$) δ(ppm): 0.87 (3H, t, J=6.8 Hz, —CH$_3$), 1.2–1.4 (8H, m, —(CH$_2$)$_4$—), 2.0, 2.01, 2.09 and 2.15 (4 x 3H, 4s, 4 x —OCOCH$_3$), 2.08 (2H, m, =CH—C$\underline{H}_2$), 3.52 (1H, dd, J=10.7 and 7.7 Hz, H-1), 3.88 (1H, dd, J=10.7 and 3.54 Hz, H-1), 3.93 (1H, m, H-2), 4.09 (2H, m, H-6'), 4.24 (1H, m, H-5), 5.13–5.18 (2H, m, H-1' and H-2'), 5.34–5.39 (1H, m, H-3'), 5.49 (1 H, dd, J=3.3 and 1.2 Hz, H-4'), 5.53–5.61 (2H, m, H-3 and H-4), 5.9–6.0 (1H, m, H- 5), 7.47, 7.59 and 8.05 (2H, 1H and 2H, 3m, —C$_6$H$_5$).

Anal. Calcd. for $C_{32}H_{43}N_3O_{12}$: C 58.03; H 6.55; N 6.35. Found: C 58.14; H 6.38; N 6.37.

β-anomer: Clear oil.

$[\alpha]_D^{22}$: –28° (c=1.0, CHCl$_3$).

IR (NaCl, film) $\upsilon_{max}$ (cm$^{-1}$): 2108 (N$_3$), 1750 and 1725 (C=O).

$^1$H NMR 400 MHz (CDCl$_3$) δ(ppm): 0.87 (3H, t, J=6.8 Hz, —CH$_3$), 1.26–1.4 (8H, m, —(CH$_2$)$_4$—), 1.99, 2.03, 2.11 and 2.16 (4 x 3H, 4s, 4 x —OCOCH$_3$), 2.09 (2H, m, =CH—CH$_2$), 3.60 (1H, m, H-1), 3.85–3.97 (2H, m, H-1 and H-2), 4.12 (2H, ABX system, J$_{AB}$=11 Hz, J$_{AX}$=5.07 Hz and J$_{BX}$=5.1 Hz, H-6'), 4.51 (1H, d, J=7.97 Hz, H-1'), 5.02 (1H, dd, J=10.54 and 3.41 Hz, H-3'), 5.25 (1H, dd, J=10.54 and 7.97 Hz, H-2'), 5.39 (1H, dd, J=3.41 and 0.87 Hz, H- 4'), 5.53–5.62 (2H, m, H-3 and H-4), 5.94 (1H, dt, J=14.3 and 7.1 Hz, H-5), 7.27, 7.48 and 8.06 (2H, 1H and 2H, 3m, —C$_6$H$_5$).

Anal. Calcd. for $C_{32}H_{43}N_3O_{12}$: C 58.03; H 6.55; N 6.35. Found: C 57.89; H 6.29; N 6.30.

H. (2S,3R,4E)-2-Azido-3-benzoyloxy-1-(β-D-galactopyranosyloxy)-4-undecene

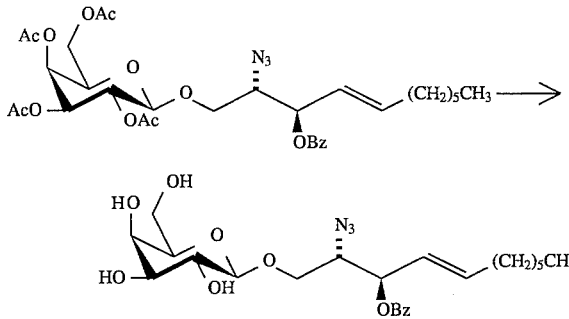

(2S,3R,4E)-2-Azido-3-benzoyloxy-1-(2,3,4,6-tetra-O-acetyl-β-D-galactopyranosyloxy)- 4-undecene (1.148 g, 1.73 mmol) was treated by the general procedure as described in Example 1-B and gave 0.761 g (89%) of the title material as a glass.

$[\alpha]_D^{22}$: –29.5° (c=1.0, CHCl$_3$).

IR (NaCl, film) $\upsilon_{max}$ (cm$^{-1}$): 2105 (N$_3$),1720 (C=O).

$^1$H NMR 200 MHz (DMSO-d$_6$) δ(ppm): 0.82 (3H, t, J=6.4 Hz, —CH$_3$), 1.1–1.4 (8H, m, —(CH$_2$)$_4$—) 2.03, (2H, m, =CH—CH$_2$—), 3.2–3.65 (7H, m, H-1, H-2', H-3', H-4', H-5 and H-6'), 3.76 (1H, dd, J=7.7 and 10.4 Hz, H-1), 4.2 (1H, d, J=6.9 Hz, H-1'), 4.16 (1H, m, H-2), 4.38 (1H, d, J=4.5 Hz, —OH), 4.54 (1H, t, J=5.5 Hz, —OH), 4.72 (1H, d, J=5.1 Hz, —OH), 4.90 (1H, d, J=4.4 Hz, —OH), 5.55 (1H, dd, J=7.6 and 14.7 Hz, H-4), 5.64 (1H, dd, J=3.45 and 7.6 Hz, H-3), 5.88 (1H, dt, J=6.7 and 14.7 Hz, H-5), 7.54, 7.67 and 7.96 (2H, 1H and 2H, 3m, —C$_6$H$_5$).

Anal. Calcd. for $C_{24}H_{35}N_3O_8$: C 58.41; H 7.15; N 8.51. Found: C 58.10; H 7.15; N 8.47.

I. (2S,3R,4E)-3-Benzoyloxy-1-(β-D-galactopyranosyloxy)-2-hexadecanoylamino- 4-undecene

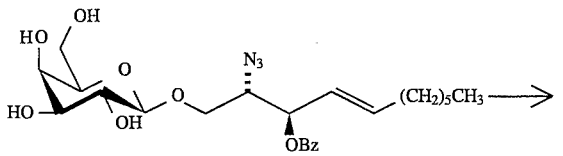

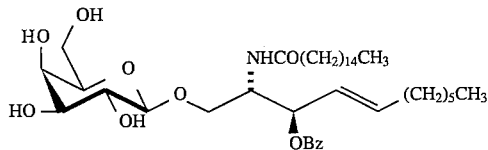

(2S,3R,4E)-2-Azido-3-benzoyloxy-1-(β-D-galactopyranosyloxy)-4-undecene (1.12 g, 3.27 mmol) was treated by the general procedure as described in Example 13-A (except that hexadecanoyl chloride was used instead of hexanoyl chloride) and gave 1.21 g (75%) of the title material as an amorphous solid.

$[\alpha]_D^{22}$: +2° (c=1.0, MeOH).

IR (KBr) $\upsilon_{max}$ (cm$^{-1}$): 1722 (C=O ester) and 1650 (C=O amide).

$^1$H NMR 400 MHz (DMSO-d$_6$) δ(ppm): 0.82 and 0.84 (2 x 3H, 2 t, J=7.07 and 6.56 Hz, 2 x —CH$_3$), 1.15–1.5 (34H, m, —(CH$_2$)$_4$— and —(CH$_2$)$_{13}$—), 1.96–2.08 (4H, m, =CH—CH$_2$— and —NHCOCH$_2$—), 3.2–3.5 (5H, m, H-2', H-3', H-5' and H-6'), 3.61 (1H, m, H-4'), 3.85 (1H, dd, J=5.35 and 10.2 Hz, H-1), 4.04 (1H, d, J=7.46 Hz, H-1'), 4.33 (1H, d, J=4.6 Hz, —OH), 4.33 (1H, m overlapping with —OH, H-2), 4.47 (1H, t, J=5.6 Hz, —OH), 4.68 (1H, dd, J=5.5 and 7.7 Hz, H-3), 5.52 (1H, dd, J=7.7 and 14.7 Hz, H-4), 5.79 (1H, dt, J=14.7 and 7.1 Hz, H-5), 7.49, 7.62 and 7.93 (2H, 1H and 2H, 3m, —C$_6$H$_5$), 7.77 (1H, d, J=9.1 Hz, —NH—).

Anal. Calcd. for $C_{40}H_{67}NO_9$: C 68.05;H 9.57; N 1.98. Found: C 68.01; H 9.54; N 2.23.

J. (2S,3R,4E)-3-Benzoyloxy-2-hexadecanoylamino-1-(3,4-O-isopropylidene-b-D-galactopyranosyloxy)-4-undecene

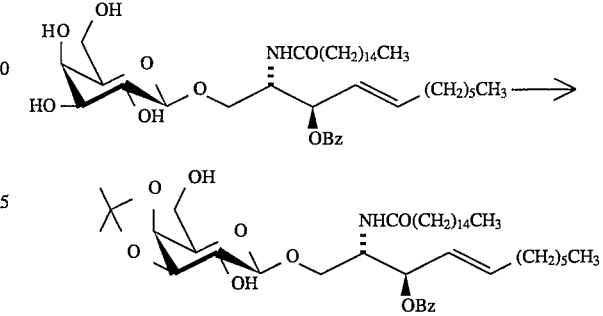

(2S,3R,4E)-3-Benzoyloxy-1-(β-D-galactopyranosyloxy)-2-hexadecanoylamino- 4-undecene (0.87 g, 1.23 mmol) was reacted by the general procedure as described in Example 5-C and gave 0.68 g (74%) of the title material as a glass.

IR (NaCl, film) $\upsilon_{max}$ (cm$^{-1}$): 1720 (C=O ester) and 1640 (C=O amide).

$^1$H NMR 400 MHz (DMSO-d$_6$) δ(ppm): 0.83 and 0.85 (2 x 3H, 2t, J=6.9 and 6.7 Hz, 2 x —CH$_3$), 1.2–1.5 (37H, m, —(CH$_2$)$_4$—, —(CH$_2$)$_{13}$— and —C(CH$_3$)$_2$—), 1.38 (3H, s, —C(CH$_3$)$_2$—), 2.0 and 2.08 (2 x 2H, 2m, —NHCOCH$_2$— and =CH—CH$_2$—), 3.22 (1H, m, H-2'), 3.42–3.55 (3H, m, H-6' and H-1), 3.70 (1H, m, H-5'), 3.83 (1H, dd, J=10.2 and 5.5 Hz, H-1), 3.92 (1H, dd, J=5.6 and 6.9 Hz, H-3'), 4.09 (1H, m overlapping with H-1', H-4'), 4.10 (1H, d, J=8.1 Hz, H-1'), 4.35 (1H, m, H-2), 4.69 (1H, br t, —OH), 5.22 (1H, d, J=4.2 Hz, —OH), 5.47 (1H, dd, J=5.7 and 7.7 Hz, H-3), 5.53 (1H, dd, J=7.7 and 14.8 Hz, H-4), 5.80 (1H, dt, J=6.7 and 14.8 Hz, H-5), 7.50, 7.64 and 7.94 (2H, 1H and 2H, 3m, —C$_6$H$_5$), 7.77 (1H, d, J=9.1 Hz, —NH—).

K. (2S,3R,4E)-3-Benzoyloxy-2-hexadecanoylamino-1-[3,4-O-isopropylidene- 2,6-di-O-(sodium oxysulfonyl)-β-D-galactopyranosyloxy]- 4-undecene

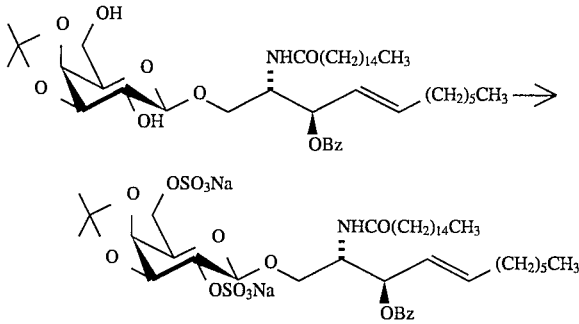

(2S,3R,4E)-3-Benzoyloxy-2-hexadecanoylamino-1-( 3,4-O-isopropylidene-β-D-galactopyranosyloxy)- 4-undecene (0.260 g, 0.349 mmol) was reacted by the general procedure as described in Example 5-D and gave 0.200 g (61%) of the title material as an amorphous solid.

IR (KBr) $\upsilon_{max}$ (cm$^{-1}$): 1725 (C=O ester) and 1645 (C=O amide).

$^1$H NMR 400 MHz (DMSO-d$_6$) δ(ppm): 0.81 and 0.84 (2 x 3H, 2 t, J=6.9 and 6.7 Hz, 2 x —CH$_3$), 1.15–1.45 (37H, m, —(CH$_2$)$_4$—, —(CH$_2$)$_{13}$— and —C(CH$_3$)$_2$—), 1.35 (3H, s, —C(CH$_3$)$_2$—), 1 96 and 2.07 (2 x 2H, 2m=CH—CH$_2$— and —NHCOCH$_2$—), 3.39 (1H, dd, J=4.65 and 10.1 Hz, H-1), 3.72–3.82 (2H, m, H-6'), 3.85 (1H, m, H-5'), 3.93 (1H, dd, J=3.7 and 10.1 Hz, H-1), 4.1–4.4 (2H, m, H-3' and H-4'), 4.25 (1H, dd, J=5.25 and 6.4 Hz, H-2'), 4.25 (1H, m overlapping with H-2', H-2), 4.49 (1H, d, J=5.25 Hz, H-1'), 5.38 (1H, dd, J=7.0 and 7.4 Hz, H-3), 5.46 (1H, dd, J=7.4 and 15.1 Hz, H-4), 5.73 (1H, dt, J=6.8 and 15.1 Hz, H-5), 7.49, 7.62 and 7.95 (2H, 1H and 2H, 3m, —C$_6$H$_5$), 8.06 (1H, d, J=9.06 Hz, —NH—).

Anal. Calcd. for C$_{43}$H$_{69}$NO$_{15}$S$_2$Na$_2$.H$_2$O: C 53.35, H 7.39; N 1.45. Found: C 53.41; H 7.38; N 1.66.

L. (2S,3R,4E)-3-Benzoyloxy-2-hexadecanoylamino-1-[2,6-di-O-(sodium oxysulfonyl)-β-D-galactopyranosyloxy]-4-undecene

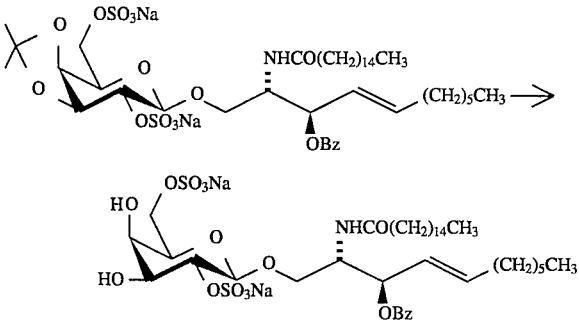

(2S,3R,4E)-3-Benzoyloxy-2-hexadecanoylamino-1-[3,4-O-isopropyl-idene- 2,6-di-O-(sodium oxysulfonyl)-β-D-galactopyranosyloxy]-4-undecene (0.390 g, 0.41 mmol) was reacted by the general procedure as described in Example 18 and gave 0.300 g (81%) of the title material as an amorphous solid.

$[\alpha]_D^{22}$: +1.5° (c=1.0, MeOH).

IR (KBr) $\upsilon_{max}$ (cm$^{-1}$): 1710 (C=O ester) and 1685 and 1660 (C=O amide).

$^1$H NMR 400 MHz δ(ppm): 0.81 and 0.84 (2 x 3H, 2 t, J=6.9 and 6.7 Hz, 2 x CH$_3$), 1.15–1.5 (34H, m, —(CH$_2$)$_{13}$— and —(CH$_2$)$_4$—), 1.9–2.0 and 2.0–2.2 (2 x 2H, 2m, —NHCOCH$_2$— and =CH—CH$_2$—), 3.45–3.51 (2H, m, H-1 and H-3' overlapping), 3.58 (1H, br t, H-5'), 3.62 (1H, m, H-4'), 3.66 (1H, dd, J$_{AB}$=10.6 Hz, J$_{AX}$=5.8 Hz, J$_{BX}$=6.4 Hz, H-6'), 3.74 (1H, dd, J$_{AB}$=10.6 Hz, J$_{AX}$=5.8 Hz, J$_{BX}$=6.4 Hz, H-6'), 3.95 (1H, dd, J=4.66 and 9.8 Hz, H-1), 4.16 (1H, dd, J=7.8 and 9.4 Hz, H-2'), 4.24 (1H, m, H-2), 4.68 (1H, d, J=4.2 Hz, —OH), 5.12 (1H, d, J=1.4 Hz, —OH), 5.40 (1H, dd, J=6.2 and 7.45 Hz, H- 3), 5.46 (1H, dd, J=7.45 and 14.9 Hz, H-4), 5.75 (1H, dt, J=6.8 and 14.9 Hz, H-5), 7.50, 7.61 and 7.95 (2H, 1H and 2H, 3m, —C$_6$H$_5$), 7.74 (1H, d, J=8.8 Hz, —NH—).

EXAMPLE 26

(2S,3R,4E)-2-Hexadecanoylamino-3-hydroxy-1-[2,6-di-O-(sodium oxysulfonyl)-β-D-galactopyranosyloxy]-4-undecene

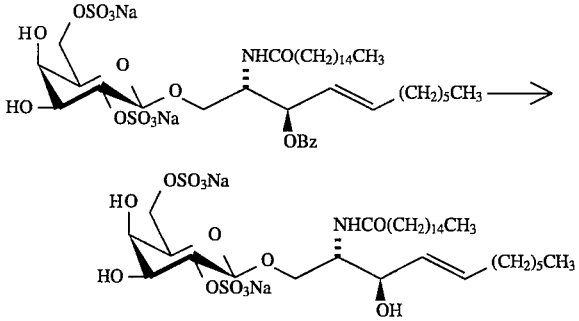

(2S,3R,4E)-3-Benzoyloxy-2-hexadecanoylamino-1-[2,6-di-O-(sodium oxysulfonyl)-β-D-galactopyranosyloxy)-4-undecene (0.200 g, 0.22 mmol) was reacted by the general procedure as described in Example 6-A and gave 0.16 g (88%) of the title material as an amorphous solid.

$[\alpha]_D^{22}$: +4.5° (c=1.0, MeOH).

IR (KBr) $\upsilon_{max}$ (cm$^{-1}$): 1680 and 1640 (C=O amide).

$^1$H NMR 400 MHz (DMSO-d$_6$) δ(ppm): 0.84 (6H, t, J=6.7 Hz, 2 x —CH$_3$), 1.2–1.5 (34H, m, —(CH$_2$)$_{13}$— and —(CH$_2$)$_4$—), 1.89 and 2.08 (2 x 2H, 2m, —NHCOCH$_2$— and =CH—CH$_2$—), 3.26 (1H, dd, J=3.6 and 9.5 Hz, H-1), 3.47 (1H, m, H-3'), 3.57 (1H, br t, H-5'), 3.62 (1H, m, H-4'), 3.7 (1H, m, H-3), 3.75–3.9 (3H, m, H-2 and H-6'), 4.09 (1H, dd, J=7.64 and 9.2 Hz, H-2'), 4.12 (1H, dd, J=2.9 and 9.5 Hz, H-1), 4.23 (1H, d, J=7.64 Hz, H-1'), 4.68 (1H, d, J=4.2 Hz, —OH), 4.85 (1H, d, J=5.6 Hz, —OH), 4.95 (1H, d, J=1.5 Hz, —OH), 5.30 (1H, dd, J=7.1 and 15.3 Hz, H-4), 3.48 (1H, dt, J=6.65 and 15.3 Hz, H-5), 7.41 (1H, d, J=9.2 Hz, —NH—).

What is claimed is:
1. A compound of the formula

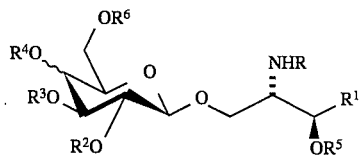

wherein

R is an acyl residue of a fatty acid;

$R^1$ is —$(CH=CH)_m$—$(CH_2)_n$—$CH_3$;

$R^2$, $R^3$, $R^4$ and $R^6$ each are independently —$SO_3H$, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or $R_4$ and $R_6$, taken together are benzylidene; or $R_3$ and $R_4$, taken together are isopropylidene; provided at least two of $R^2$, $R^3$, $R^4$ and $R^6$ are —$SO_3H$;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive;

or a non-toxic pharmaceutically acceptable salt, solvate or hydrate thereof.

2. A compound of claim 1 having the formula

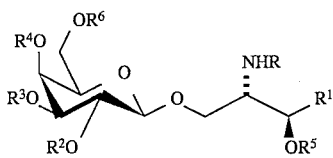

wherein

R is an acyl residue of a fatty acid;

$R^1$ is —$(CH=CH)_m$—$(CH_2)_n$—$CH_3$;

$R^2$, $R^3$, $R^4$ and $R^6$ each are independently —$SO_3H$, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or $R_4$ and $R_6$, taken together are benzylidene; or $R_3$ and $R_4$, taken together are isopropylidene; provided at least two of $R^2$, $R^3$, $R^4$ and $R^6$ are —$SO_3H$;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive;

or a non-toxic pharmaceutically acceptable salt, solvate or hydrate thereof.

3. A compound of claim 1 having the formula

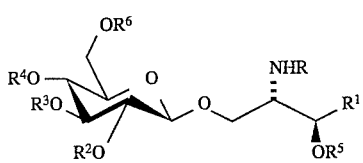

wherein

R is an acyl residue of a fatty acid;

$R^1$ is —$(CH=CH)_m$—$(CH_2)_n$—$CH_3$;

$R^2$, $R^3$, $R^4$ and $R^6$ each are independently —$SO_3H$, hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or $R_4$ and $R_6$, taken together are benzylidene; or $R_3$ and $R_4$, taken together are isopropylidene; provided at least two of $R^2$, $R^3$, $R^4$ and $R^6$ are —$SO_3H$;

$R^5$ is hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy;

m is an integer of 0 or 1;

n is an integer of from 5 to 14, inclusive;

or a non-toxic pharmaceutically acceptable salt, solvate or hydrate thereof.

4. A compound of claim 1 wherein $R^4$ and $R^6$ are —$SO_3H$ and $R^2$, $R^3$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or a non-toxic pharmaceutically acceptable salt, solvate or hydrate thereof.

5. A compound of claim 1 wherein $R^2$ and $R^6$ are —$SO_3H$ and $R^3$, $R^4$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or $R^3$ and $R^4$, taken together are isopropylidene; or a non-toxic pharmaceutically acceptable salt, solvate or hydrate thereof.

6. A compound of claim 1 wherein $R^3$ and $R^6$ are —$SO_3H$ and $R^2$, $R^4$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or a non-toxic pharmaceutically acceptable salt, solvate or hydrate thereof.

7. A compound of claim 1 wherein $R^2$ and $R^3$ are —$SO_3H$ and $R^4$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; or $R^4$ and $R^6$, taken together are benzylidene; or a non-toxic pharmaceutically acceptable salt, solvate or hydrate thereof.

8. A compound of claim 1 wherein $R^3$ and $R^4$ are —$SO_3H$ and $R^2$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

9. A compound of claim 1 wherein $R^2$ and $R^4$ are —$SO_3H$ and $R^3$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy or a non-toxic pharmaceutically acceptable salt, solvate or hydrate thereof.

10. A compound of claim 4 wherein $R^2$, $R^3$ and $R^5$ each are independently hydrogen or benzoyl; or a non-toxic pharmaceutically acceptable salt, solvate or hydrate thereof.

11. A compound of claim 5 wherein $R^3$, $R^4$ and $R^5$ each are independently hydrogen or benzoyl; or a non-toxic pharmaceutically acceptable salt, solvate or hydrate thereof.

12. A compound of claim 6 wherein $R^2$, $R^4$ and $R^5$ each are independently hydrogen or benzoyl; or a non-toxic pharmaceutically acceptable salt, solvate or hydrate thereof.

13. A compound of claim 7 wherein $R^4$, $R^5$ and $R^6$ each are independently hydrogen or benzoyl; or a non-toxic pharmaceutically acceptable salt, solvate or hydrate thereof.

14. A compound of claim 8 wherein $R^2$, $R^5$ and $R^6$ each are independently hydrogen or benzoyl; or a non-toxic pharmaceutically acceptable salt, solvate or hydrate thereof.

15. A compound of claim 9 wherein $R^3$, $R^5$ and $R^6$ each are independently hydrogen or benzoyl; or a non-toxic pharmaceutically acceptable salt, solvate or hydrate thereof.

16. A compound of claim 7 wherein $R^4$ and $R^6$, taken together are benzylidene; or a non-toxic pharmaceutically acceptable salt, solvate or hydrate thereof.

17. A compound of claim 5 wherein $R^3$ and $R^4$, taken together are isopropylidene; or a non-toxic pharmaceutically acceptable salt, solvate or hydrate thereof.

18. A compound of claim 1 wherein R is the acyl residue of palmitic acid, lignoceric acid, nervonic acid or stearic acid; or a non-toxic pharmaceutically acceptable salt, solvate or hydrate thereof.

19. A compound of claim 10 wherein R is the acyl residue of palmitic acid, lignoceric acid, nervonic acid or stearic acid; or a non-toxic pharmaceutically acceptable salt, solvate or hydrate thereof.

20. A compound of claim 11 wherein R is the acyl residue of palmitic acid, lignoceric acid, nervonic acid or stearic acid; or a non-toxic pharmaceutically acceptable salt, solvate or hydrate thereof.

21. A compound of claim 12 wherein R is the acyl residue of palmitic acid, lignoceric acid, nervonic acid or stearic acid; or a non-toxic pharmaceutically acceptable salt, solvate or hydrate thereof.

22. A compound of claim 13 wherein R is the acyl residue of palmitic acid, lignoceric acid, nervonic acid or stearic acid; or a non-toxic pharmaceutically acceptable salt, solvate or hydrate thereof.

23. A compound of claim 14 wherein R is the acyl residue of palmitic acid, lignoceric acid, nervonic acid or stearic acid; or a non-toxic pharmaceutically acceptable salt, solvate or hydrate thereof.

24. A compound of claim 15 wherein R is the acyl residue of palmitic acid, lignoceric acid, nervonic acid or stearic acid; or a non-toxic pharmaceutically acceptable salt, solvate or hydrate thereof.

25. A compound of claim 1 wherein m is 1 and n is 12; or a non-toxic pharmaceutically acceptable salt, solvate or hydrate thereof.

26. A compound of claim 1 wherein m is 0 and n is 14; or a non-toxic pharmaceutically acceptable salt, solvate or hydrate thereof.

27. A compound of claim 19 wherein R is the acyl residue of nervonic acid; or a non-toxic pharmaceutically acceptable salt, solvate or hydrate thereof.

28. A compound of claim 27 wherein m is 1 and n is 12; or a non-toxic pharmaceutically acceptable salt, solvate or hydrate thereof.

29. A compound of claim 27 wherein m is 0 and n is 14; or a non-toxic pharmaceutically acceptable salt, solvate or hydrate thereof.

30. A compound of claim 20 wherein R is the acyl residue of nervonic acid; or a non-toxic pharmaceutically acceptable salt, solvate or hydrate thereof.

31. A compound of claim 30 wherein m is 1 and n is 12; or a non-toxic pharmaceutically acceptable salt, solvate or hydrate thereof.

32. A compound of claim 30 wherein m is 0 and n is 14; or a non-toxic pharmaceutically acceptable salt, solvate or hydrate thereof.

33. A compound of claim 1 selected from the group consisting of:

(2S,3R,4E)-3-Benzoyloxy-2-hexadecanoylamino-1-[2,3-di-O-benzoyl- 4,6-di-O-(sodium oxysulfonyl)-β-D-galactopyranosyloxy]-4-octadecene;

(2S,3R,4E)-3-Hydroxy-2-hexadecanoylamino-1-[4,6-di-O-(sodium oxysulfonyl)-β-D-galactopyranosyloxy]-4-octadecene;

(2S,3R,4E)-2-Hexadecanoylamino-3-benzoyloxy-1-(2,3-di-O-benzoyl- 4,6-di-O-(sodium oxysulfonyl)-β-D-glucopyranosyloxy)-4-octadecene;

(2S,3R,4E)-2-Hexadecanoylamino-3-hydroxy-1-(4,6-di-O-(sodium oxysulfonyl)-β-D-glucopyranosyloxy)-4-octadecene;

(2S,3R,4E)-3-Benzoyloxy-1-[2,6-di-O-(sodium oxysulfonyl)-β-D-galactopyranosyloxy]-2-(cis-15-tetracosenoylamino)-4-octadecene;

(2S,3R,4E)-3-Hydroxy-1-[2,6-di-O-(sodium oxysulfonyl)-β-D-galactopyranosyloxy]-2-(cis-15-tetracosenoylamino)-4-octadecene;

(2S,3R,4E)-3-Benzoyloxy-1-[3,4-di-O-benzoyl-2,6-di-O-(sodium oxysulfonyl)-β-D-galactopyranosyloxy]-2-(cis-15-tetracosenoylamino)-4-octadecene;

(2S,3R,4E)-3-Benzoyloxy-2-hexadecanoylamino-1-[2-O-benzoyl- 4-O-acetyl-3,6-di-O-(sodium oxysulfonyl)-β-D-galactopyranosyloxy]-4-octadecene;

(2S,3R,4E)-3-Hydroxy-2-hexadecanoylamino-1-[3,6-di-O-(sodium oxysulfonyl)-β-D-galactopyranosyloxy]-4-octadecene;

(2S,3R,4E)-3-Benzoyloxy-2-hexadecanoylamino-1-[2,3-di-O-(sodium oxysulfonyl)-4,6-O-benzylidene-β-D-galactopyranosyloxy)-4-octadecene;

(2S,3R,4E)-3-Benzoyloxy-2-hexadecanoylamino-1-[2,3-di-O-(sodium oxysulfonyl)-β-D-galactopyranosyloxy)-4-octadecene;

(2S,3R,4E)-3-Hydroxy-2-hexadecanoylamino-1-[2,3-di-O-(sodium oxysulfonyl)-β-D-galactopyranosyloxy)-4-octadecene;

(2S,3R,4E)-3-Benzoyloxy-2-hexanoylamino-1-[3,4-O-isopropylidene- 2,6-di-O-(sodium oxysulfonyl)-β-D-galactopyranosyloxy]-4-octadecene;

(2S,3R, 4E)-3-Benzoyloxy-2-hexanoylamino-1-[2,6-di-O-(sodium oxysulfonyl)-β-D-galactopyranosyloxy]-4-octadecene;

(2S,3R,4E)-3-Hydroxy-2-hexanoylamino-1-[2,6-di-O-(sodium oxysulfonyl)-β-D-galactopyranosyloxy]-4-octadecene;

(2S,3R,4E)-3-Benzoyloxy-1-[2,3-di-O-benzoyl-4,6-di-O-(sodium oxysulfonyl)-β-D-glucopyranosyloxy]-2-(cis-15-tetracosanoylamino)-4-octadecene;

(2S,3R,4E)-2-Hexadecanoylamino-3-benzoyloxy-1-[2,3-di-O-benzyl- 4,6-di-O-(sodium oxysulfonyl)-β-D-galactopyranosyloxy]-4-octadecene;

(2S,3R)-3-Benzoyloxy-1-(2,3-di-O-benzoyl-4,6-di-O-(sodium oxysulfonyl)-β-D-galactopyranosyloxy)- 2-tetracosanoyl-aminooctadecane;

(2S,3R)-3-Hydroxy-1-[4,6-di-O-(sodium oxysulfonyl)-β-D-galactopyranosyloxy]- 2-tetracosanoylaminooctadecane;

(2S,3R,4E)-2-Hexadecanoylamino-3-benzoyloxy-1-[2,6-di-O-(sodium oxysulfonyl)-β-D-galactopyranosyloxy]-4-octadecene;

(2S,3R,4E)-2-Hexadecanoylamino-3-hydroxy-1-[2,6-di-O-(sodium oxysulfonyl)-β-D-galactopyranosyloxy]-4-octadecene;

(2S,3R)-3-Benzoyloxy-1-[2,6-di-O-(sodium oxysulfonyl-β-D-galactopyranosyloxy]- 2-tetracosanoylaminooctadecane;

(2S,3R)-3-Hydroxy-1-[2,6-di-O-(sodium oxysulfonyl)-β-D-galactopyranosyloxy]- 2-tetracosanoylaminooctadecane;

(2S,3R,4E)-3-Benzoyloxy-2-hexadecanoylamino-1-[2,6-di-O-(sodium oxysulfonyl)-β-D-galactopyranosyloxy]-4-undecene; and (2S,3R,4E)-2-Hexadecanoylamino-3-hydroxy-1-[2,6-di-O-(sodium oxysulfonyl)-β-D-galactopyranosyloxy]-4-undecene; or a non-toxic pharmaceutically acceptable salt, solvate or hydrate thereof.

34. A pharmaceutical composition comprising a therapeutically effective amount of a compound as defined in claim 1 in association with a pharmaceutically acceptable carrier or diluent.

35. A method for the treatment of inflammatory diseases in a mammal in need thereof, which comprises administering to said mammal a therapeutically effective amount of a compound as defined in claim 1 or a pharmaceutical composition thereof.

36. A method for the treatment of inflammatory diseases in a mammal in need thereof, which comprises administering to said mammal a therapeutically effective amount of a compound as defined in claim 2 or a pharmaceutical composition thereof.

37. A method for the treatment of inflammatory diseases in a mammal in need thereof, which comprises administering to said mammal a therapeutically effective amount of a compound as defined in claim 4 or a pharmaceutical composition thereof.

38. A method for the treatment of inflammatory diseases in a mammal in need thereof, which comprises administering to said mammal a therapeutically effective amount of a compound as defined in claim 5 or a pharmaceutical composition thereof.

* * * * *